US009777317B2

(12) United States Patent
Spoto et al.

(10) Patent No.: US 9,777,317 B2
(45) Date of Patent: Oct. 3, 2017

(54) MICROFLUIDIC PCR DEVICE

(71) Applicants: STMicroelectronics S.r.l., Agrate (IT); bioMérieux S.A., Marcy l'Etoile (FR)

(72) Inventors: Giuseppe Emanuele Spoto, Trecastagni (IT); Luigi Giuseppe Occhipinti, Ragusa (IT); Cristian Dall'Oglio, Niscemi (IT); Crocifisso Marco Antonio Renna, Gela (IT); Laurent Drazek, Grenoble (FR)

(73) Assignees: STMicroelectronics S.r.l., Agrate Brianza (IT); bioMérieux S.A., Marcy l'Etoile (FR)

( * ) Notice: Subject to any disclaimer, the term of this patent is extended or adjusted under 35 U.S.C. 154(b) by 726 days.

(21) Appl. No.: 13/956,677

(22) Filed: Aug. 1, 2013

(65) Prior Publication Data

US 2014/0038193 A1    Feb. 6, 2014

(30) Foreign Application Priority Data

Aug. 3, 2012  (IT) .............................. TO2012A0703

(51) Int. Cl.
*C12Q 1/68* (2006.01)
*B01L 3/00* (2006.01)

(52) U.S. Cl.
CPC ............ *C12Q 1/686* (2013.01); *B01L 3/5027* (2013.01); *B01L 2300/0816* (2013.01); *B01L 2300/0864* (2013.01)

(58) Field of Classification Search
None
See application file for complete search history.

(56) References Cited

U.S. PATENT DOCUMENTS 5,849,208 A * 12/1998 Hayes .................. B01J 19/0093
216/100
5,925,517 A  7/1999 Tyagi et al.
(Continued)

FOREIGN PATENT DOCUMENTS

EP     2 382 324 A1    11/2001
IT     IO 34088         4/2013

OTHER PUBLICATIONS

Sun et al. (J of Chromatography, 2006, vol. 1117, p. 228-233).*

*Primary Examiner* — Stephanie K Mummert
(74) *Attorney, Agent, or Firm* — Seed IP Law Group LLP

(57) ABSTRACT

A microfluidic device (1000-1005), comprising: a semiconductor body (2) having a first side (2a) and a second side (2b) opposite to one another, and housing, at the first side, a plurality of wells (4), having a first depth; an inlet region (30) forming an entrance point for a fluid to be supplied to the wells; a main channel (6a) fluidically connected to the inlet region, and having a second depth; and a plurality of secondary channels (6b) fluidically connecting the main channel to a respective well, and having a third depth. The first depth is higher than the second depth, which in turn is higher than the third depth. According to an aspect, the microfluidic device further comprises a cover layer (8), arranged above the first side of the semiconductor body, configured for sealing the wells and provided with at least a first valve hole (54) which extends through the cover layer and overlaps, at least partially, the secondary channels; and a flexible layer (14), arranged above the cover layer and provided with at least a protrusion (74) extending through the first valve hole towards the semiconductor body and overlapping, at least partially, the secondary channels, the flexible layer being configured such that, when a pressure is applied on it, the protrusion contacts the semiconductor (Continued)

body and enters the secondary channels thus fluidically isolating the wells from one another.

38 Claims, 35 Drawing Sheets

(56) References Cited

U.S. PATENT DOCUMENTS

| | | |
|---|---|---|
| 6,004,515 A | 12/1999 | Parce et al. |
| 6,034,130 A | 3/2000 | Wang et al. |
| 6,103,476 A | 8/2000 | Tyagi et al. |
| 6,150,097 A | 11/2000 | Tyagi et al. |
| 6,461,817 B1 | 10/2002 | Alland et al. |
| 2003/0152994 A1* | 8/2003 | Woudenberg ....... B01L 3/50273 435/6.12 |

* cited by examiner

MICROFLUIDIC PCR DEVICE

PRIOR RELATED APPLICATIONS

This application claims priority to Italian Application Number TO2012A000703, filed Aug. 3, 2012 and incorporated by reference in its entirety herein.

FEDERALLY SPONSORED RESEARCH STATEMENT

Not applicable.

FIELD OF THE DISCLOSURE

The present disclosure relates to a disposable microfluidic device, in particular to a disposable device, or platform, for multiplex parallel real time amplification such as PCR (Polymerase Chain Reaction).

BACKGROUND OF THE DISCLOSURE

Polymerase Chain Reaction, or PCR, allows an initial amount of DNA in a suitable reaction mix to be copied many times, thus increasing the amount of that DNA in the sample. PCR consists of repeated cycles of a denaturing phase wherein the DNA double helix is separated, an annealing phase wherein primers bind to the DNA target, and an extension phase wherein the primers are elongated by DNA polymerase, thus selectively amplifying the target DNA.

Real time quantitative PCR (qPCR) is a widely used technique based on monitoring the PCR reaction during its progress. This can be accomplished thanks to suitable fluorescent probes, which bind either to the target DNA or to the duplex DNA, and thus allow signal increases as the reaction proceeds and the DNA is amplified.

Multiplex PCR is the simultaneous amplification of more than one target sequence in a single reaction, and multiplex PCR can also be performed in real time PCR assay format. Known multiplex real-time PCR platforms use probe-based assays, in which each target DNA has a specific probe labeled with a unique fluorescent dye, resulting in different observed colors for each assay.

It is also possible to use two labels per probe, with a fluorescent dye at one end and a quencher at the other end. This technology is called Molecular Beacons®, commercially available from SIGMA-ALDRICH®, and described in U.S. Pat. Nos. 5,925,517, 6,034,130, 6,103,476, 6,150,097, and 6,461,817.

Molecular Beacons® are hairpin shaped molecules with an internally quenched fluorophore, whose fluorescence is restored when it binds to a target nucleic acid sequence and thus unwind the hairpin, separating the two labels, which then no longer quench each other, and resulting in a signal increase.

The TaqMan® probe is analogous to the molecular beacon probe, having two labels in close proximity that quench each other when in a hairpin loop formation. However, the TaqMan® probe hybridizes to target DNA between the pair of primers, so the 5' exonuclease activity of the DNA polymerase cleaves off the fluorophore, allowing an increase in fluorescence.

Scorpion® probes are another real time PCR probe having dual labels that quench each other when in a hairpin loop formation. Scorpions® contain a PCR primer covalently linked to a hairpin probe with dual quenched labels. During a PCR reaction, the fluorophore and quencher are separated, which leads to an increase in light output from the reaction tube. The important difference between this technology and TaqMan® is that the probe and the target in a Scorpion® reaction are in the same molecule such that signal generation is via a uni-molecular rearrangement. In contrast, a TaqMan® reaction requires a bi-molecular collision.

Ideally, a real-time multiplex PCR should be able to detect, differentiate, and provide a quantitative result for many different targets without any single target influencing the detection of one of the others (cross-talk) and without loss of sensitivity. The ideal platform would also allow both multiplexed assays and massively parallel assays, so that a great many assays can be performed at once. Further, the platform would require only small volumes and provide a reproducible result very quickly, and microfluidic platforms have been developed to fill this need.

However, known microfluidic platforms do not provide sufficient parallelism (i.e. number of reaction chambers working in parallel), combined with small volumes of reagents and sample (e.g., less than 300 nl per chamber), high versatility, ease of use and cost effectiveness, all necessary in order to improve the manufacturing scalability in large volumes of the fabricated disposable devices and also to reduce the overall cost of the envisaged solution, including the cost of both the disposable device and reagents.

Moreover, known microfluidic devices having a plurality of reaction chambers or wells formed in a same substrate, still suffer from cross contamination between the wells (fluid/reagent within one well mix with the fluid/reagent from another well). This drawback is identifiable in known microfluidic devices irrespectively of the particular use of such microfluidic devices.

BRIEF SUMMARY

The aim of the present disclosure is to provide a disposable microfluidic device that overcomes the aforementioned limitations, in particular a microfluidic device wherein cross contamination among wells is reduced or eliminated during use, while providing a high degree of parallelism, and taking advantage of small sample volumes, and speed in obtaining results.

According to the present disclosure it is provided disposable microfluidic device as defined in the attached claims.

DESCRIPTION OF DRAWINGS

For a better understanding of the disclosure, preferred embodiments thereof are now described, purely by way of non-limiting example and with reference to the annexed drawings, wherein:

FIG. 3b is an enlarged view of a portion of the body of FIG. 3a.

FIG. 4b is an enlarged view of a portion of the body of FIG. 4a.

FIG. 5a shows a perspective view of a cover layer adapted to cover the body of FIG. 3a and the body of FIG. 4a.

FIG. 5b shows a top view of the cover layer of FIG. 5a arranged on the body of FIG. 3a or the body of FIG. 4a.

FIG. 5c shows a top view of a cover layer according to a further embodiment, alternative to the embodiment of FIG. 5a.

FIG. 7a shows a perspective view of a flexible layer adapted to be arranged above the cover layer of FIG. 5a.

FIG. 7b is a cross sectional view of the flexible layer of FIG. 7a, taken along the section line VII-VII of FIG. 7a.

FIG. 8 shows a perspective view of a gas/liquid separation membrane adapted to be arranged above the flexible layer of FIG. 7a.

FIG. 10b shows an enlarged perspective view of a portion of the body of FIG. 10a.

FIG. 12a shows a perspective view of an adhesion layer according to an embodiment alternative to the adhesion layer of FIG. 6.

FIG. 12b is an enlarged view of a portion of the adhesion layer of FIG. 12a.

FIG. 22a shows an enlarged portion of the fluidic domain of FIG. 21a.

DETAILED DESCRIPTION

Figure 1A:
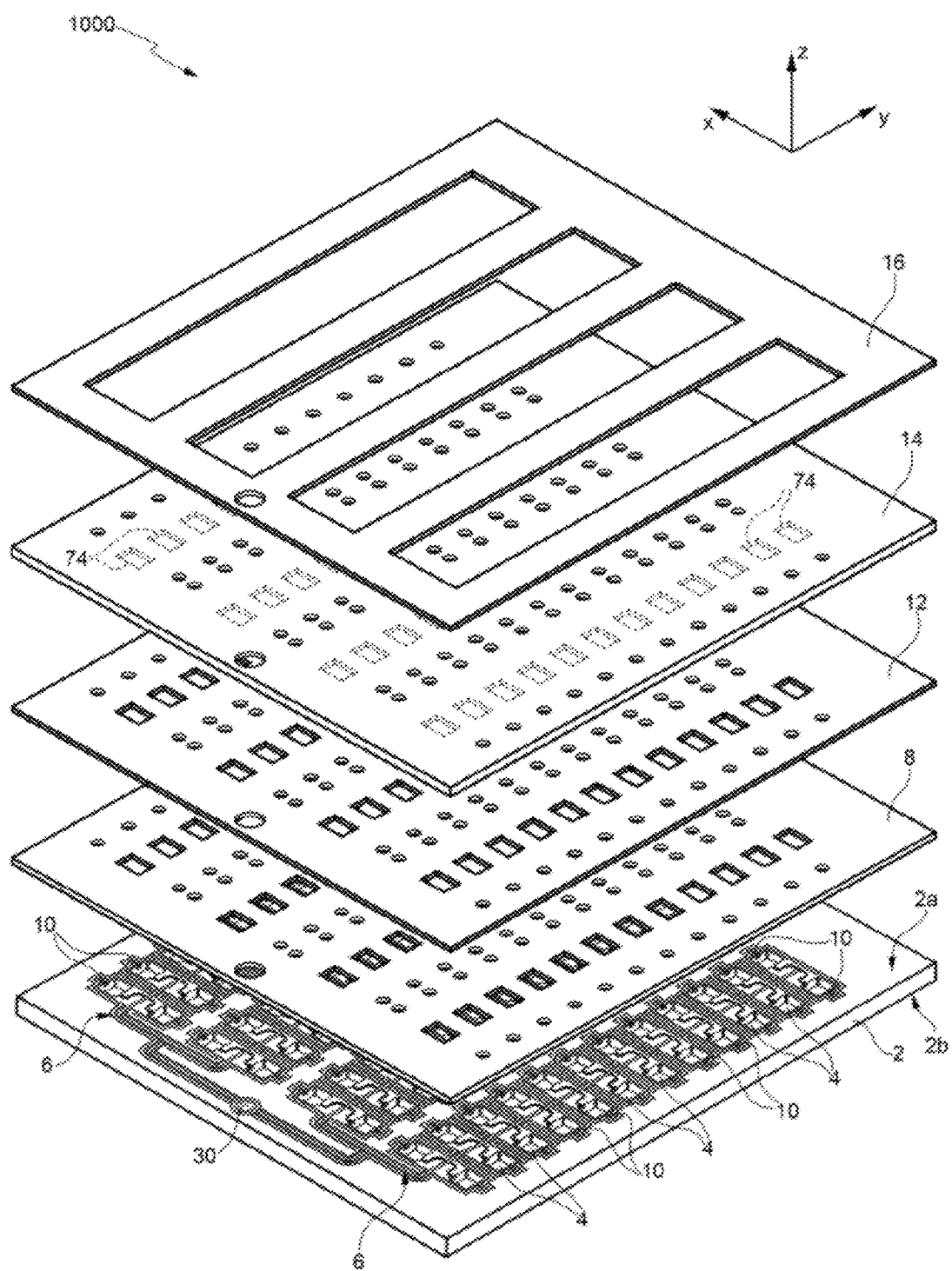
FIG. 1a is an expanded view of a microfluidic device according to one embodiment.

One embodiment herein described provides a microfluidic device comprising a body (e.g., semiconductor body that can be processed according to known MEMS manufacturing techniques) having a first side and a second side opposite to one another, and having on the first side of the body: at least a couple of wells or chambers adapted to store a fluid or a liquid; an inlet region forming an entrance point for the fluid or liquid to be supplied to the wells; a main channel fluidically connected to the inlet region; and at least a couple of secondary channels fluidically connecting the main channel to a respective well.

The wells extend within the body for a first depth, the main channel extends within the body for a second depth, the secondary channels extend within the body for a third depth, the first depth being greater than the second depth, and the second depth being greater than the third depth. The multi-level channels and chambers thus provide for a reduced contamination between wells.

According to a first aspect of the aforementioned embodiment, the secondary channels are coupled to opposite sides of the main channel and are staggered with respect to one another. This further reduces cross contamination between wells since the fluidic path from one well to an adjacent well is increased. See for example FIG. 10a, 10b and related description.

According to a second aspect of the aforementioned embodiment (in combination with the aforementioned first aspect or alternative to the first aspect), the microfluidic device further comprises a flexible layer, arranged above the first side of the body, provided with at least a protrusion extending towards the first side of the body and overlapping, at least partially, the secondary channels. During use, the flexible layer, at the protrusion level, can be moved from a first position to a second position such that, in the first position the protrusion is above the body and allows transfer of fluid within the secondary channels, and in the second position, the protrusion contacts the body and enters within at least one of the secondary channels, thus fluidically isolating at least one well from the main channel. In particular, the protrusion completely obstructs at least one secondary channel (i.e., the protrusion enters within the secondary channel for the entire depth of the secondary channel).

According to one embodiment, the protrusion is made of a moldable material that undergoes deformation so as to enter within all the secondary channels, thus fluidically isolating all of the wells from the main channel from each other. In general, the flexible layer is configured such that, when a pressure is applied on it, the protrusion contacts the first side of the body and enters within at least one of the secondary channels, thus fluidically isolating the wells from one another. In this way, the cross contamination among wells is still further reduced.

The ensuing discussion is presented to enable a person skilled in the art to implement and use the invention. Various modifications to the embodiments will be evident to persons skilled in the art, without thereby departing from the scope of the present invention as claimed. Consequently, the present invention is not to be understood as being limited to the embodiments illustrated, but it must be granted the widest scope in accordance with the principles and characteristics illustrated in the present description and defined in the annexed claims.

Figure 1B:
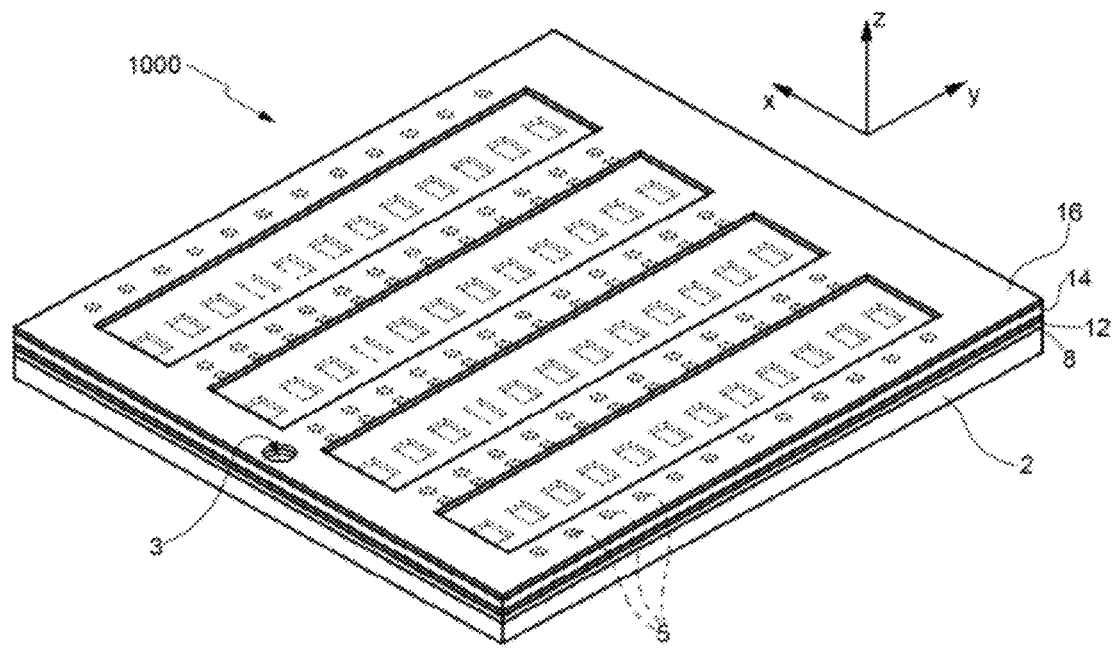
FIG. 1b shows a perspective view of the microfluidic device of FIG. 1a in an assembled form.

FIG. 1a shows an expanded view of a microfluidic device 1000 according to one embodiment. FIG. 1b shows the microfluidic device 1000 of FIG. 1a assembled. With reference to both FIGS. 1a and 1b, the microfluidic device 1000 includes a body 2, for example of semiconductor material such as silicon or monocrystalline silicon, having a first surface 2a and a second surface 2b opposite to one another. Other materials may be used for the body 2, such as plastic (e.g., biocompatible plastic), glass, ceramics, metals, or even other materials. However, semiconductor materials are preferred for cost and ease of precision manufacturing, and also because the silicon conducts heat very efficiently.

The body 2 houses, at the first surface 2a, one or more wells 4 connected to a network of channels 6. The wells 4 and the network of channels 6 are formed in the body 2 by known microfabrication techniques (MEMS technology), such as lithography and etching.

Above the first surface 2a of the body 2 is arranged a cap 8, made of rigid or semi-rigid material, for example of biocompatible, transparent and non fluorescent plastic polymers, such as, but not limited to, polycarbonate or polyacrylate. The cap 8 has a thickness from 50 μm to 150 μm, for example equal to about 100 μm. According to one embodiment, the cap 8 is secured to the first surface 2a of the body 2 by glue (not shown), such as, but not limited to, an injectable glue made of transparent and non fluorescent materials and curable at low temperature, such as cyano acrylate or epoxy-based glues.

The cap 8 is adapted to contact the first surface 2a of the body 2 in such a way to seal the network of channels 6 from the top. To allow an hermetic seal of the channels 6 by cap 8, it is expedient to provide the first surface 2a of the body 2 with one or more grooves 10 outlining the wells 4 and/or the channels 6. The grooves 10 hold and control the glue, which is placed within the grooves 10 prior to arranging the cap 8 above the body 2. In this way, the glue does not cause an undesirable spacing between the first surface 2a of the body 2 and the cap 8, which could hinder the sealing of the channels 6 by the cap 8. Moreover, since the glue is confined within the grooves 10, the glue cannot obstruct (neither completely nor partially) the channels 6.

Above the cap 8 is arranged a first bi-adhesive layer 12, having one adhesive side adhering to the cap 8 and the other adhesive side binding to the layer above 14. The first bi-adhesive layer 12 has a thickness from 10 μm to 100 μm, for example equal to about 50 μm.

In preferred embodiments, the first bi-adhesive layer 12 includes a patterned transparent film carrier having two sides. One side of the carrier is coated by a pressure sensitive adhesive (e.g., silicone), while the opposite side is coated by an acrylic-based adhesive.

Above the first bi-adhesive layer 12 is arranged a flexible layer 14 of a bio-compatible material, for example of elastomeric material. In particular, PDMS (polydimethylsiloxane), PMMA (polymethyl-methacrylate)), or silicone, and the like, can be used. The flexible layer 14 adheres to another side of the first bi-adhesive layer 12. In this way, the first bi-adhesive layer 12 is arranged between the cap 8 and the flexible layer 14, and couples the flexible layer 14 to the cap 8.

The flexible layer 14 is provided with protrusions 74 (described in detail with reference to FIG. 7a, 7b) configured to extend through the first bi-adhesive layer 12 and the cap 8. Accordingly, the first bi-adhesive layer 12 and the cap 8 are provided with apertures to allow the passage of the protrusions 74.

The flexible layer 14 has a minimum thickness (protrusions 74 excluded) in the range from 100 μm to 500 μm, for example of about 150 μm.

Above the flexible layer 14 is arranged a membrane 16, adapted to act as a gas/liquid separator. The membrane 16 is a microporous membrane, for example made of polypropylene, polyethylene, polyvinyltetrafluorethylene, polycarbonate, and other hydrophobic porous membranes, which is configured to allow the passage of a gas (for example, air), but does not allow the passage of any liquid. According to an embodiment, the membrane has a pore size from about 50 nm to about 150 nm, for example of about 100 nm, and should not interfere with the fluorescence of the active materials and detection system.

Each one of the layers 8, 12, 14 and 16 is provided with a respective inlet hole, which align and form an inlet 3 when the microfluidic device 1000 is assembled as shown in FIG. 1b. The inlet channel 3 extends from the membrane 16 to the body 2, and allows fluidic access to the network of channels 6, during use of the microfluidic device 1000.

Each of the layers 8, 12 and 14 (but not the membrane 16) are moreover provided with a respective air exhaust hole 52, 62, 72 (described in detail with reference to FIGS. 5A-C, 6 and 7A). When the microfluidic device 1000 is assembled as shown in FIG. 1b, air exhaust holes 52, 62, 72 align to form an air exhaust micro channel 5 extending from the flexible layer 14 to the body 2. The air exhaust micro channels 5 are fluidically coupled to the wells 4 and allow an air flow out of the wells 4 when, during use of the microfluidic device 1000, they are being filled with liquid. The membrane 16 covers the air exhaust micro channels 5 so as to block a liquid flow out of the wells 4 through the air outlet micro channels 5. The membrane 16 has a thickness from 50 µm to 300 µm, for example equal to about 100 µm.

Figure 2A:
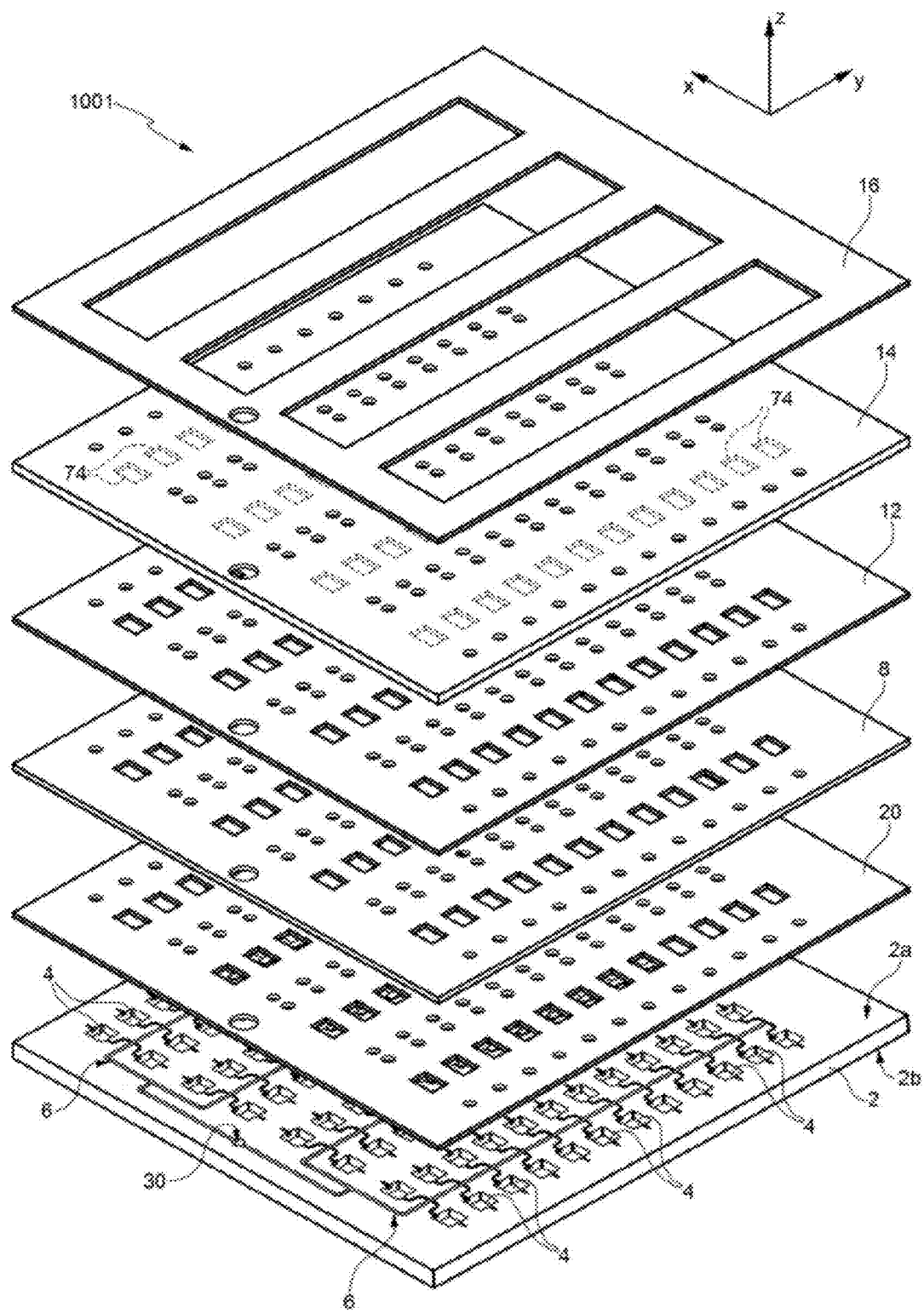
FIG. 2a is an expanded view of a microfluidic device according to a further embodiment.
Figure 2B:
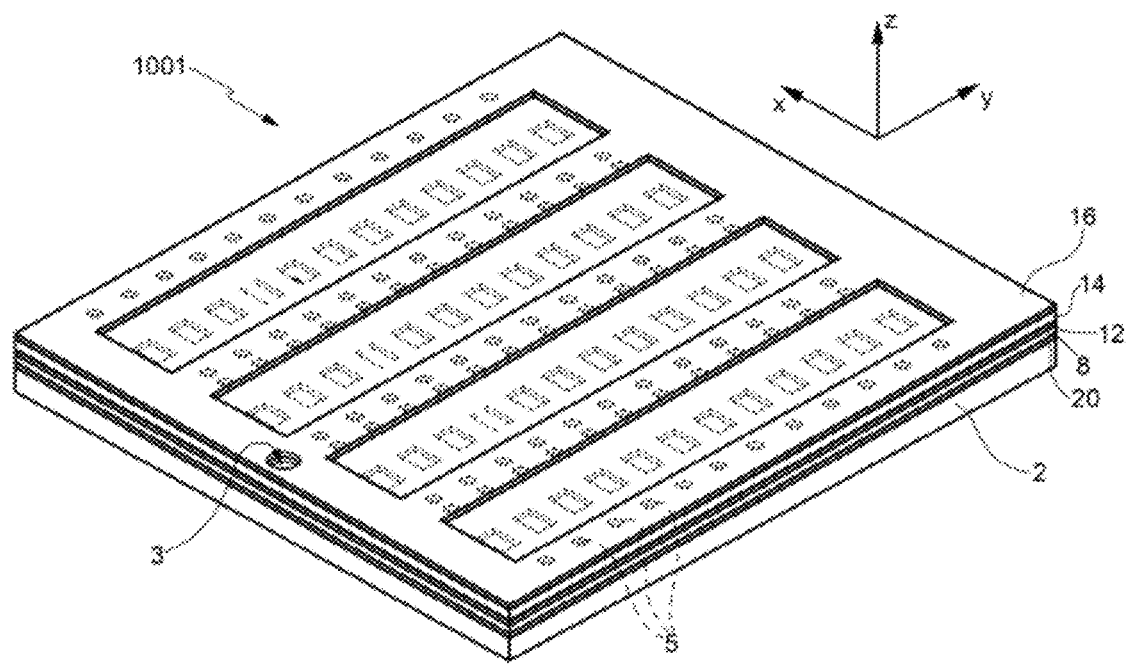
FIG. 2b shows a perspective view of the microfluidic device of FIG. 2a in an assembled form.

FIG. 2a shows an exploded view of a microfluidic device 1001 according to a further embodiment of the present invention. FIG. 2b shows the microfluidic device 1001 assembled.

According to the embodiment of the microfluidic device 1001, shown in FIGS. 2a and 2b, the cap 8 is secured to the first surface 2a of the body 2 by means of a second bi-adhesive layer 20, instead of glue as in FIG. 1. The second bi-adhesive layer 20 has an adhesive side in direct contact with the first surface 2a of the body 2, an opposite adhesive side in contact with the cap 8. In this way, the cap 8 is attached to the body 2 by means of the second bi-adhesive layer 20 that acts as a gluing layer.

In preferred embodiments, the second bi-adhesive layer 20 includes a patterned transparent film carrier having two sides. One side of the carrier is coated by a pressure sensitive adhesive (e.g., silicone), while the opposite side is coated by an acrylic-based adhesive. However, the adhesives can vary.

The glue, as described with reference to the embodiment of FIG. 1a, 1b, is not a requisite for the embodiment of FIG. 2a, 2b. Accordingly, also the grooves 10 are not required.

It is clear that, according to further embodiments (not shown), any other coupling element to secure the cap 8 to the semiconductor layer 2 may be used. For example, the layers can be glued, adhered, clamped together, heat welded, RF welded, ultrasound welded, solvent welded, laser welded, or any other means known in the art, and depending on the materials employed.

Figure 3A:
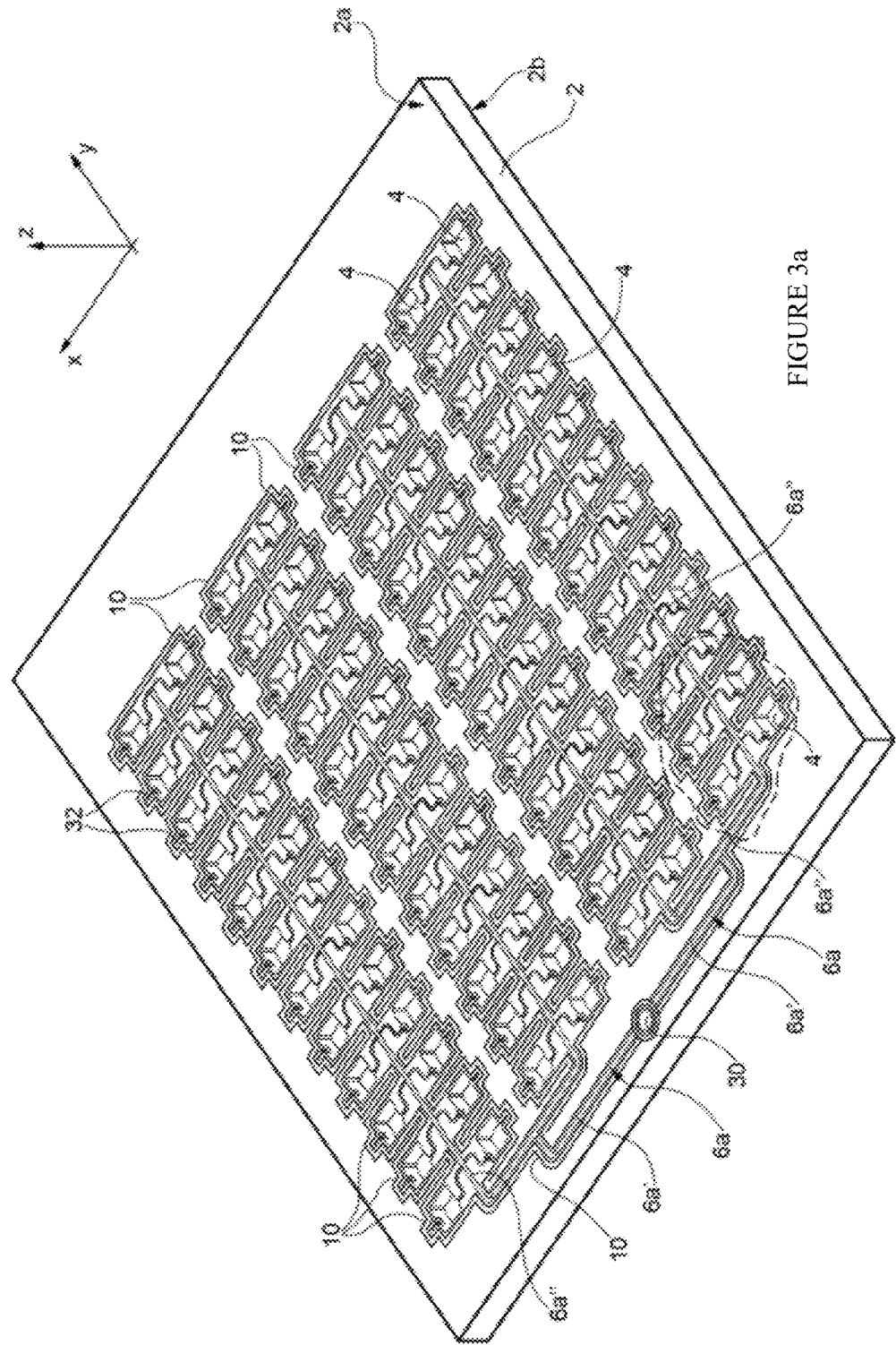
FIG. 3a shows a perspective view of a body of the microfluidic device of FIGS. 1a and 1b provided with a plurality of wells and channels.
Figure 3B:
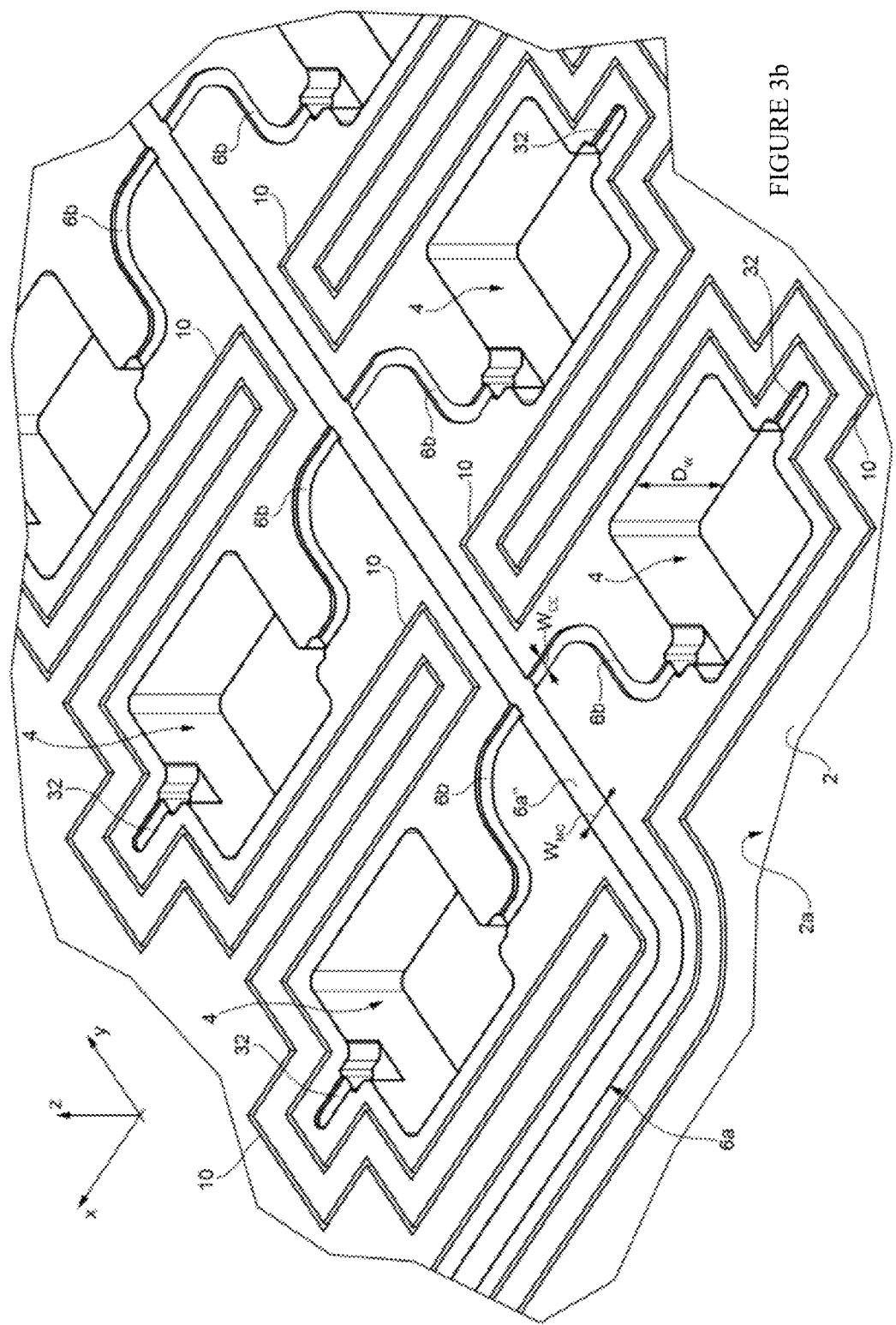

FIG. 3a shows a perspective view of the body 2 according to the embodiment of FIG. 1a. FIG. 3b shows an enlarged view of a selected portion of the first side 2a of the body 2 of FIG. 3a (the portion shown in FIG. 3b is encircled by a dashed line in FIG. 3a).

The body 2 has a thickness from about 500 µm to about 800 µm, for example equal to about 675 µm.

The body 2 according to FIG. 3a comprises an inlet region 30, configured to receive a liquid. The inlet region 30 is a common inlet region 30 for all the channels 6 and the wells 4 formed in the body 2. The inlet region 30 is etched in the body 2 and has a depth, measured from the first side 2a along a Z axis, ranging from about 100 µm to about 150 µm, for example equal to about 120 µm. The inlet region 30 as shown has a substantially cylindrical shape. However, other shapes are possible, for example cubic shape, parallelepiped shape, or any other shape.

In greater detail, the network of channels 6 includes a main channel 6a, directly connected to the inlet region 30. The main channel 6a comprises a plurality of main branches 6a' and sub-branches 6a".

The aim of the main branches 6a' and sub-branches 6a" is to form a suitable network to supply the plurality of wells 4 with the liquid injected, during use at the inlet region 30. It is apparent that the conformation, the extension and/or the number of the branches 6a' and sub-branches 6a" is freely selectable according to the users need. For example, a single main channel 6a (without further branches) may be provided, additional branches can be added, or the pattern of branches can be varied.

A plurality of cross channels 6b radiates from the sub-branches 6a". Each cross channel 6b is moreover fluidically coupled to a respective well 4, so that the liquid injected at the inlet region 30 is supplied to the wells 4 through the network of channels 6.

According to the embodiment of FIG. 3a, the wells 4 are organized as an array having one or more rows (along a X axis) and one or more columns (along a Y axis). In particular, the wells 4 which are connected to a same sub-branch 6a", and extending at a same side of the sub-branch 6a" to which they are connected, are substantially aligned to one another along a direction parallel to the Y axis. Analogously, wells 4 connected to the same sub-branch 6a", but on the opposite side thereof, are also substantially aligned.

Each of the wells 4 is fluidically connected to a respective air outlet region 32, clearly visible in FIG. 3b, departing from a side of the respective well 4. The air outlet region 32 has the form of a strip or groove etched in the body 2 at the first surface 2a.

During use, when the liquid is supplied to the inlet region 30, it flows from the inlet region 30 along main channel 6a to the branches 6a', then to the sub-branches 6a", which feed individual wells 4 via individual cross channels 6b. Given the small dimension of the channels 6 (in the micrometer range), the flow of the liquid is driven by capillary action until the liquid enters the wells 4. The air outlet region 32 has the function of allowing trapped air to escape from the wells 4 when the liquid enters the wells 4.

According to a further embodiment of the present invention, the flow of the liquid is driven by positive pressure applied in a per se known way. Alternatively, the flow can be driven by negative pressure if a downstream chamber is sealed while at negative pressure. Breaking a valve, e.g., by applying heat and melting a membrane valve, will initiate flow towards the negative pressure chamber.

According to one embodiment, the main channel 6a (which, in the shown embodiment, is formed by the branches 6a' and 6a") extends within the body 2 for a depth $D_{MC}$, measured from the first surface 2a of the body 2 along the Z axis, ranging from about 100 µm to about 150 µm, for example equal to about 120 µm. In particular, the main channel 6a has a depth $D_{MC}$ that is equal to, or greater than, the depth of the inlet region 30. Moreover, the main channel 6a has a width $W_{MC}$ of about 110-130 µm.

The cross channels 6b extend within the body 2 for a depth $D_{CC}$, measured from the first surface 2a of the body 2 along the Z axis, lower than the depth $D_{MC}$ of the main channel 6a, and ranging from about 6 µm to about 12 µm, for example equal to about 10 µm when the main channel 6a has a depth $D_{MC}$ of about 120 µm. Moreover, each cross channel 6b has a width $W_{CC}$ of about 50-70 µm.

The wells 4 extend within the body 2 for a depth $D_W$, measured from the first surface 2a of the body 2 along the Z axis, greater than the depths $D_{MC}$, $D_{CC}$ of the main and cross channels 6a, 6b, and ranging from about 200 µm to about 600 µm, for example in the range of about 380 µm when the main channel 6a has a depth $D_{MC}$ of about 120 µm and the cross channels 6b have a depth $D_{CC}$ of about 10 µm. Each well 4, from a top view, is shown as having a polygonal shape, for example quadrangular shape, but any shape is possible, such as a circular shape, or any other shape.

In this way, fluid flows downhill from the inlets to the channels to the wells, and this feature assists in reducing cross-contamination.

The air outlet region 32 extends within the body 2 for a depth, measured from the first surface 2a of the body 2 along the Z axis, which is less than the thickness of the well 4 to which it is coupled (for example equal to the depth $D_{CC}$ of the cross channels 6b).

As it is more clearly visible from FIG. 3b, the grooves 10 surround, at least partially, the network of channels 6 and the wells 4. In particular, the grooves 10 extend between adjacent wells 4 not separated by the sub-branches 6a". In this way, when the cap 8 is glued to the body 2, it is ensured that adjacent wells 4 are physically isolated from one another and cross-contamination is avoided. The grooves 10 have a depth, within the body 2 measured starting from the first surface 2a along the Z axis, in the range of about 60-150 μm, for example of about 120 μm.

We have shown a pair of grooves 10, as two lines of glue provide a redundant seal at low cost, but any number is possible. Further, grooves 10 are shown as closely tracking the well and air outlet, but the exact layout of grooves can be varied, so long as the wells are separated or delineated from each other.

Figure 4A:
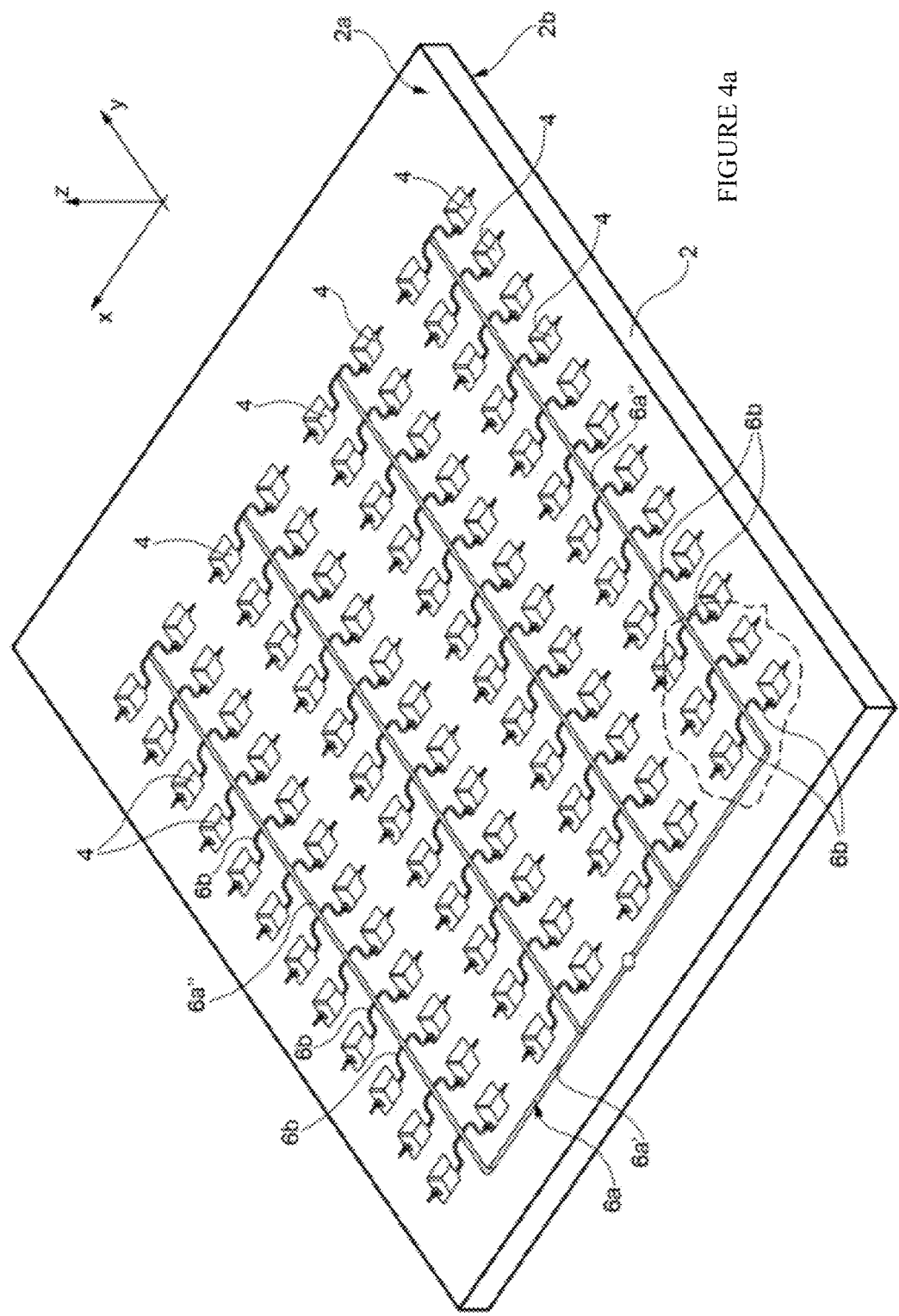
FIG. 4a shows a perspective view of a body of the microfluidic device of FIGS. 2a and 2b provided with a plurality of wells and channels.
Figure 4B:
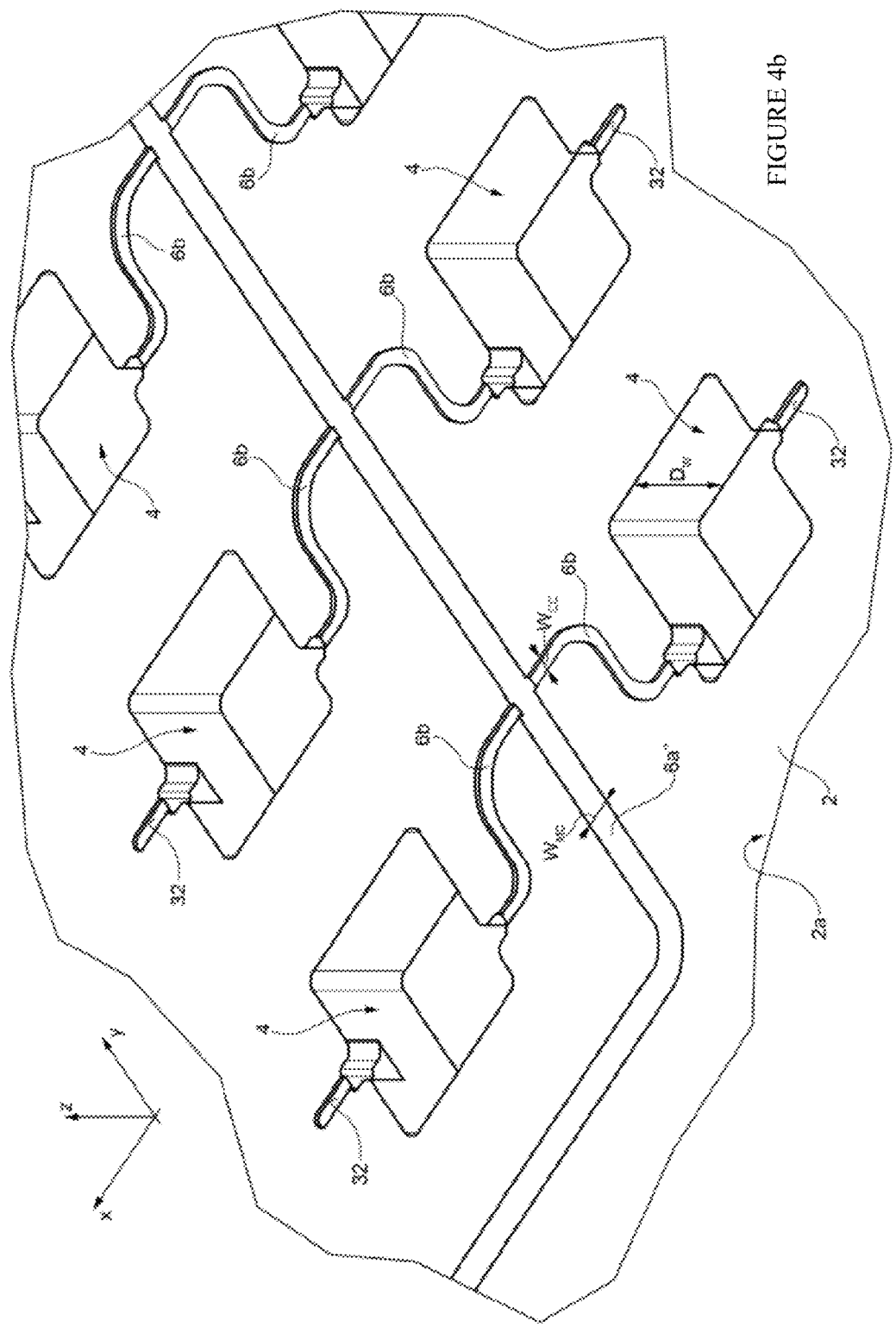

FIG. 4a shows a perspective view of the first side 2a of the body 2 according to the embodiment of the microfluidic device 1001 of FIG. 2a; FIG. 4b shows an enlarged view of a selected portion of the first side 2a of the body 2 of FIG. 4a (the portion shown in FIG. 4b is encircled by a dashed line in FIG. 4a). The embodiment of FIG. 4a, 4b is analogous to the embodiment of FIG. 3a, 3b, but the grooves 10 are omitted since a bi-adhesive layer is used instead. Elements of the embodiment of FIG. 4a, 4b common to respective elements of the embodiment of FIG. 3a, 3b are referenced with the same reference numbers and are not further described.

According to the embodiment of FIG. 4a, 4b, the adhesion between the body 2 and the cap 8, as well as the isolation between adjacent wells 4, is obtained by means of the second bi-adhesive layer 20.

Also shown in FIG. 4a, the pattern of channels 6 is simpler, and the branches 6a' and 6" develops in the body 2 in a continuous pattern.

Figure 6:
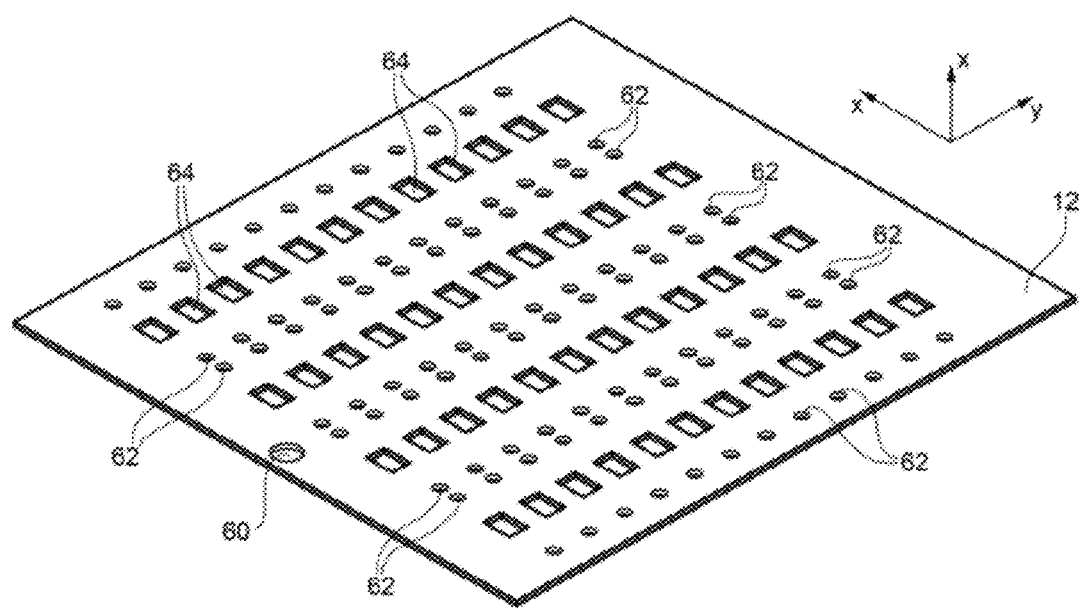
FIG. 6 shows a perspective view of an adhesion layer adapted to form a coupling interface between the body of FIG. 3a or 4a and the cover layer of FIG. 5a, or to form a coupling interface between the cover layer of FIG. 5a and further layers arranged above the cover layer.
Figure 7A:
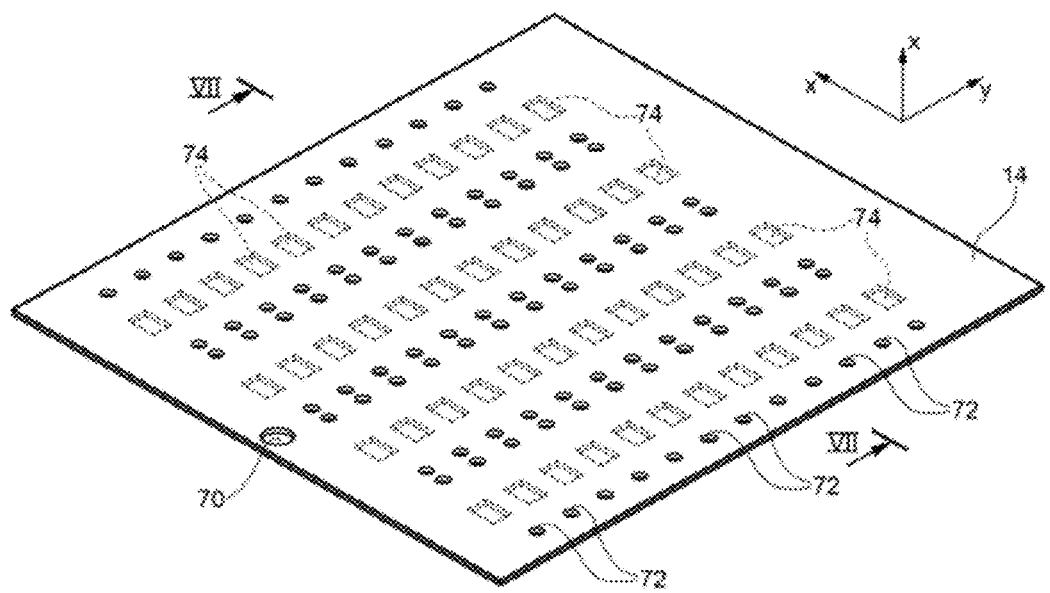
Figure 7B:
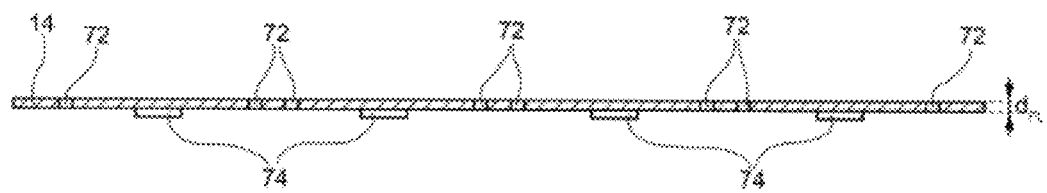
Figure 8:
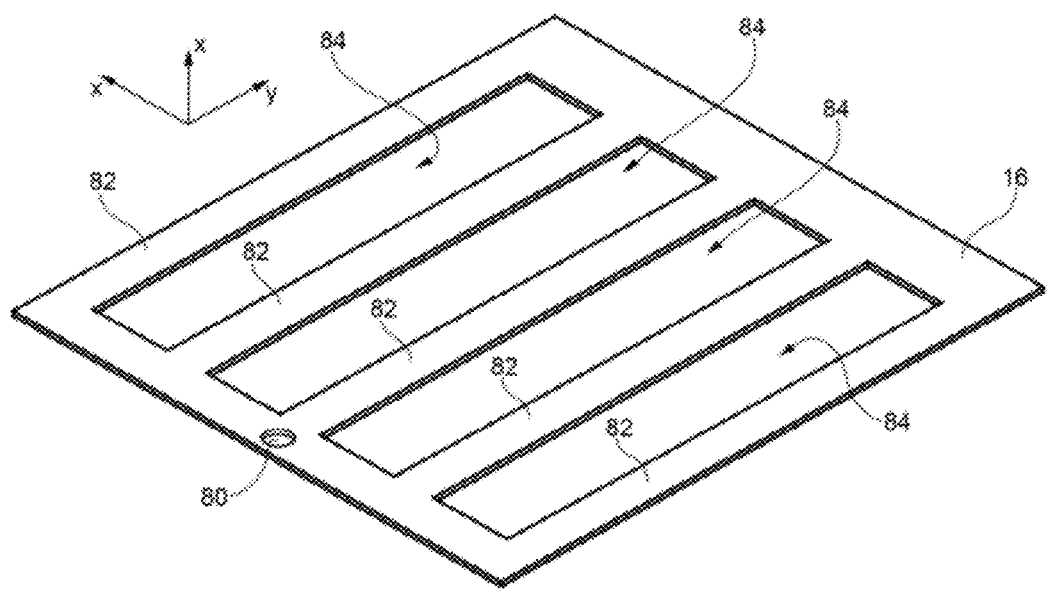

FIGS. 5a, 5b, 6, 7a, 7b, and 8 respectively show in greater detail embodiments of: the cap 8 (FIG. 5a, 5b); the first bi-adhesive layer 12 (FIG. 6); the flexible layer 14 (FIG. 7a, 7b); and the membrane 16 (FIG. 8).

Figure 5A:
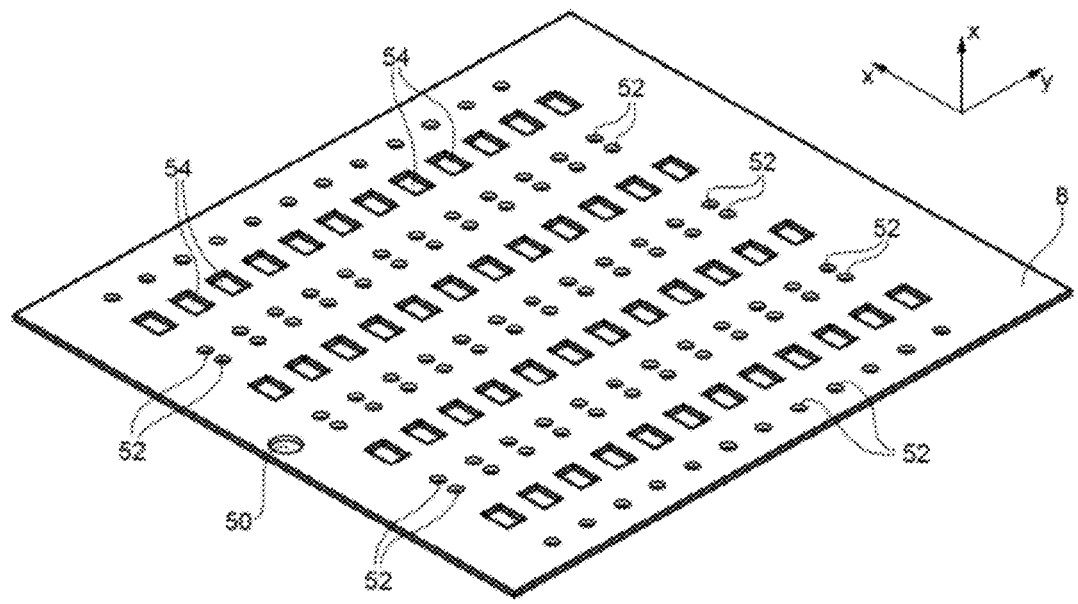

With reference to FIG. 5a, the cap 8 is shown in a perspective view. The cap 8 has a thickness from about 10 μm to about 100 μm, for example equal to about 50 μm. The cap 8 comprises a plurality of openings formed completely through it. In particular, the cap 8 comprises an inlet hole 50 having e.g., a circular shape (however, any other shape is possible). The inlet hole 50 is formed in a region of the cap 8 such that, when the cap 8 is arranged above the body 2, the inlet hole 50 is substantially aligned (along the Z axis) with the inlet region 30 of the body 2 in such a way that the inlet region 30 is accessible for injecting a liquid (for example using a pipette, not shown).

The cap 8 further comprises a plurality of air exhaust holes 52, shown here as having a circular shape (however, other shapes, generally polygonal, may be chosen). The air exhaust holes 52 are formed in a region of the cap 8 such that, when the cap 8 is arranged above the body 2, each air exhaust hole 52 is arranged above, and approximately aligned (along the Z axis) with, a respective air outlet region 32, thus being in fluidic communication with the respective air outlet region 32.

The cap 8 further comprises a plurality of valve holes 54, having herein a polygonal shape, for example quadrangular shape (but other shapes, for example circular or oval shapes may be chosen). Each valve hole 54 is formed in a region of the cap 8 such that, when the cap 8 is arranged above the body 2, each valve hole 54 extends (when considered from a top view) between two wells 4 facing a same sub-branch 6a" and aligned along the X axis. In particular, the valve hole 54 extends above a region of the body 2 housing the two cross channels 6b directly fluidically coupled to the wells 4 facing the same sub-branch 6a".

Figure 5B:
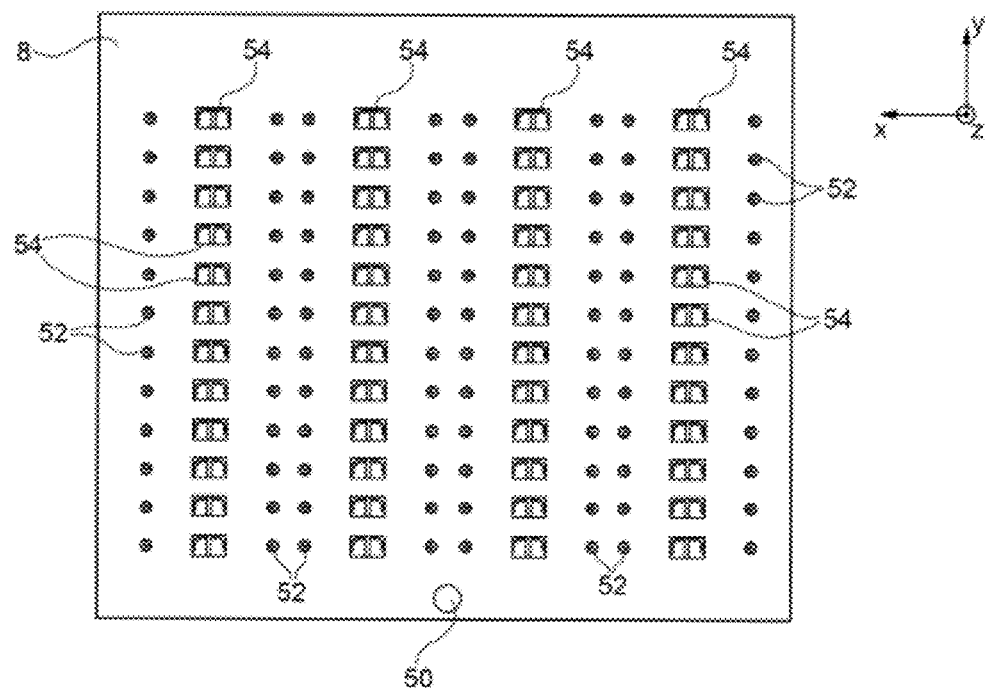

FIG. 5b shows a top view of the cap 8 arranged above the body 2, as described. According to one embodiment, when the cap 8 is arranged above the body 2, each valve hole 54 does not overlap (neither partially nor completely) with any of the wells 4. However, a partial overlap, due to misalignments, is possible and tolerated.

Figure 5C:
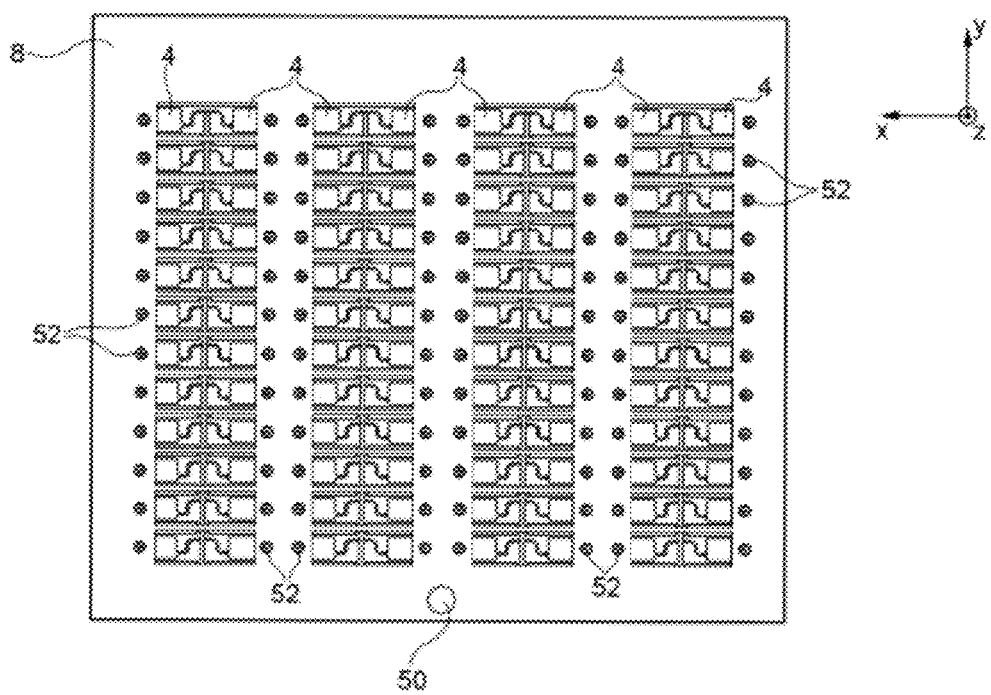

According to another embodiment, shown in FIG. 5c (top view) the cap 8 comprises further apertures above the wells 4 (i.e., each aperture is aligned, along the Z axis, with a respective well 4) in order to improve the transparency of the reaction wells and to ease the detection when it is based on fluorescence.

FIG. 6 shows, in a perspective view, the first bi-adhesive layer 12. The second bi-adhesive layer 20, according to the embodiment of FIG. 2a, 2b, has the same shape and structure as the first bi-adhesive layer 12 of FIG. 6. Accordingly, the following description, directed to the first bi-adhesive layer 12, applies analogously to the second bi-adhesive layer 20.

The first bi-adhesive layer 12 has a thickness from about 10 μm to about 100 μm, for example equal to about 50 μm. The first bi-adhesive layer 12 comprises a plurality of openings formed completely through it, analogously to the description of the cap 8 of FIG. 5a. An inlet hole 60 is formed through the first bi-adhesive layer 12 and has a circular shape, or the shape chosen for the inlet hole 50 of the cap 8.

The inlet hole 60 is formed in a region of the first bi-adhesive layer 12 such that, when the first bi-adhesive layer 12 is arranged above the body 2, the inlet hole 60 is substantially aligned, along the Z axis, with the inlet hole 50 of the cap 8, in such a way that the inlet hole 60 is also substantially aligned, along the Z axis, with the inlet region 30 of the body 2.

The first bi-adhesive layer 12 further comprises a plurality of air exhaust holes 62, having herein a circular shape (however, other shapes, generally polygonal, are possible). The air exhaust holes 62 are formed in a region of the first bi-adhesive layer 12 such that, when the first bi-adhesive layer 12 is arranged above the body 2, each air exhaust hole 62 is arranged above a respective air outlet region 32, in fluidic communication with the respective air outlet region 32 through the air exhaust holes 52 of the cap 8.

The first bi-adhesive layer 12 further comprises a plurality of valve holes 64, having herein (from a top view) a polygonal shape, for example quadrangular shape, but other shapes such as circular or oval shape are possible. In particular, the valve holes 64 have the same shape as the shape of the valve holes 54 of the cap 8, although this is not essential.

Each valve hole 64 is formed in a region of the first bi-adhesive layer 12 such that, when the first bi-adhesive layer 12 is arranged above the body 2, each valve hole 64 is arranged (when considered from a top view) between two wells 4 facing a same sub-branch 6a''', above of a region of the body 2 housing the two cross channels 6b directly fluidically coupled to the aforementioned wells 4 facing the same sub-branch 6a'''.

When the first bi-adhesive layer 12 is arranged as shown in FIGS. 1a and 1b, the inlet hole 60 of the first bi-adhesive layer 12 is substantially aligned, along the Z axis, with the inlet hole 50 of the cap 8. The air exhaust holes 62 of the first bi-adhesive layer 12 are also substantially aligned, along the Z axis, with the air exhaust holes 52 of the cap 8. Additionally, the valve holes 64 of the first bi-adhesive layer 12 are substantially aligned, along the Z axis, with the valve holes 54 of the cap 8.

FIG. 7a shows a perspective view of the flexible layer 14. The flexible layer 14 comprises an inlet hole 70, formed through the flexible layer 14 and having a circular shape (or the same shape as the shape chosen for the aforementioned inlet holes 50, 60 of the cap 8 and the first bi-adhesive layer 12, or any other desired shape). The inlet hole 70 is formed in a region of the flexible layer 14 such that, when the flexible layer 14 is arranged above the body 2, the inlet hole 70 is substantially aligned, along the Z axis, with the inlet region 30 of the body 2. Consequently, the inlet hole 70 is also substantially aligned, along the Z axis, with the inlet hole 50 of the cap 8 and the inlet hole 60 of the first bi-adhesive layer 12 in such a way that the inlet region 30 is accessible for adding fluids to the device.

The flexible layer 14 further comprises a plurality of air exhaust holes 72, having e.g., a circular shape (however, other shapes, generally polygonal, are possible). The air exhaust holes 72 are formed in a region of the flexible layer 14 such that, when the flexible layer 14 is arranged above the body 2, each air exhaust hole 72 is arranged above and in fluidic communication with a respective air outlet region 32, through the air exhaust holes 52 and 72. The air exhaust holes 72, the air exhaust holes 62 and the air exhaust holes 52 are substantially vertically aligned (i.e., aligned along the Z axis) to form a respective air exhaust micro channel 5.

The flexible layer 14 further comprises a plurality of protrusions 74 extending from a surface of the flexible layer 14 (see also FIG. 7b, which shows a section view of the flexible layer 14, taken along the section line VII-VII of FIG. 7a). The protrusions 74 have a polygonal shape such that, when the flexible layer 14 is mounted above the cap 8 and the first bi-adhesive layer 12, the protrusions 74 extends through the valve holes 54 and 64 and approach (or contact) the first surface 2a of the body 2 in the region of the first surface 2a where the cross channels 6b are formed (i.e., between two wells 4 facing one another along the X axis). Thus, the thickness of the protrusions 74 is substantially equal to the sum of the thicknesses of the cap 8 and the first bi-adhesive layer 12.

According to a different embodiment, the thickness of the protrusions 74 is higher than the sum of the thicknesses of the cap 8 and the first bi-adhesive layer 12, for example higher of a quantity equal to the depth $D_{CC}$ of the cross channels 6b.

According to a still different embodiment, the thickness of the protrusions 74 is lower than the sum of the thicknesses of the cap 8 and the first bi-adhesive layer 12.

Figure 7C:
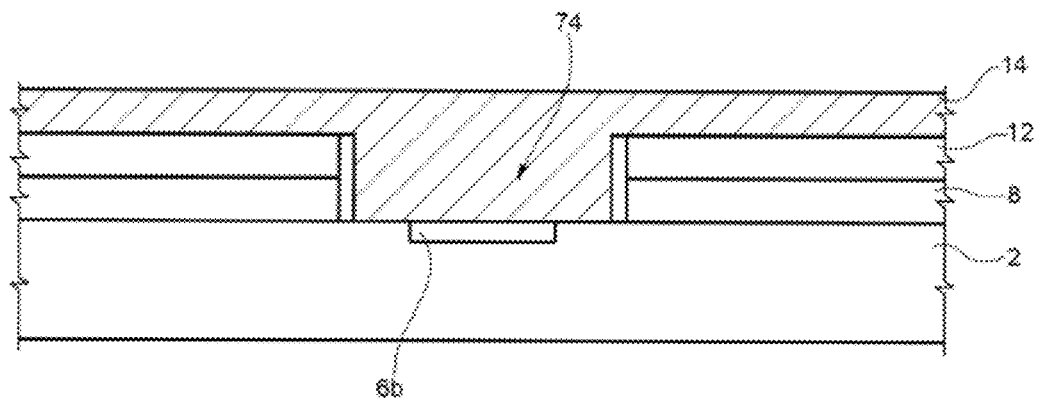
FIG. 7c is a cross sectional view of a portion of the microfluidic device of FIG. 1b, in a first operative condition.

FIG. 7c shows a cross section of a portion of the microfluidic device of FIG. 1b wherein the protrusion 74 contact the body 2 but it does not enter within the cross channel 6b. A fluid is thus free to flow through the cross channel 6b.

Irrespective of the chosen embodiment for the thickness of the protrusions 74, during use the protrusions 74 are pressed (FIG. 7d) against the body 2 so that at least part of the protrusions 74 enters within the secondary channels 6b, obstructing the secondary channels 6b. This may be achieved, for example, using the device holder shown in FIG. 17-19 and described later on.

The flexible layer 14 has a thickness $D_{FL}$ (not including the protrusions 74) from about 100 μm to about 500 μm, for example equal to about 150 μm.

When considering the embodiment of the microfluidic device 1001 of FIG. 2a, 2b, the thickness of the protrusions 74 is substantially equal to the sum of the thicknesses of the cap 8, the first bi-adhesive layer 12, and the second bi-adhesive layer 20. In particular, each protrusion 74 completely fills the space of the valve holes resulting from the stacking of the cap 8, the first bi-adhesive layer 12 and the second bi-adhesive layer 20.

According to another embodiment of the microfluidic device 1001 of FIG. 2a, 2b, the thickness of the protrusions 74 is higher than the sum of the thicknesses of the cap 8, the first bi-adhesive layer 12, and the second bi-adhesive layer 20, for example it is thick enough to penetrate and block the cross channels 6b.

According to a still different embodiment of the microfluidic device 1001, the thickness of the protrusions 74 is lower than the sum of the thicknesses of the cap 8, the first bi-adhesive layer 12 and the second bi-adhesive layer 20, so that it is assured that they not interfere with the liquid flowing through the network of channels 6 during the step of supplying the wells 4.

Figure 7D:
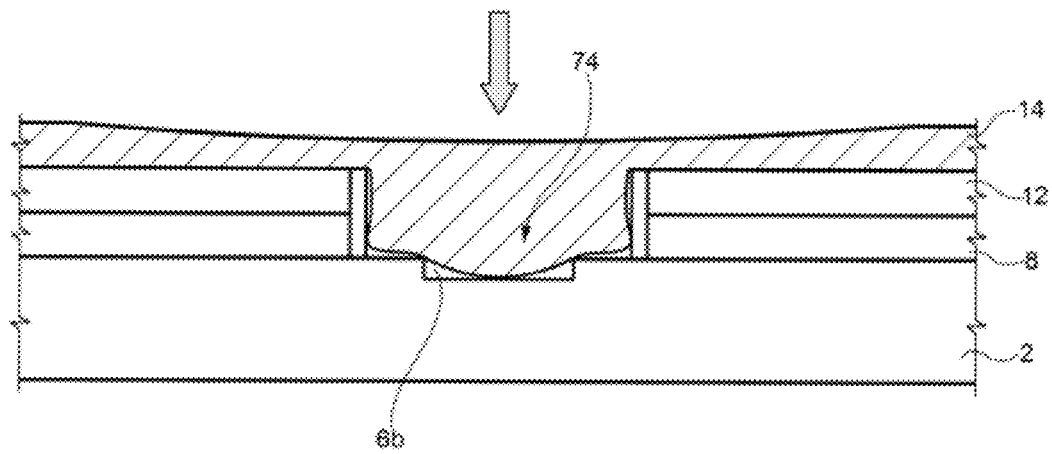
FIG. 7d is the same cross sectional view of FIG. 7c, but in a second operative condition.

Irrespective of the chosen embodiment for the thickness of the protrusion of the microfluidic device 1001, during use the protrusions 74 can be operated as already described with reference to FIGS. 7c and 7d.

FIG. 8 shows a perspective view of the membrane 16. The membrane 16 is adapted to cover, when arranged above the flexible layer 14 as shown in FIG. 1a, 1b and FIG. 2a, 2b, the air exhaust holes 72 so as to close the air exhaust micro channels 5. Membrane 16 is a microporous membrane configured for allowing gas (e.g., air) passage through it, while preventing the passage of a liquid. The membrane is glued to the elastomeric layer. The membrane allows gas to escape, thus allowing fluid flow into the wells; it may also prevent cross contamination of fluid via the air vents.

The membrane 16 has a thickness from about 50 μm to 300 μm, for example equal to about 100 μm. Membrane 16 has an inlet hole 80, formed completely through the membrane 16. The inlet hole 80 is formed in a region of the membrane 16 such that, when the membrane 16 is arranged above the body 2, the inlet hole 80 is substantially aligned, along the Z axis, with the inlet region 30 of the body 2, in such a way that it is of no hindrance for liquid injection at the inlet region 30. Consequently, the inlet hole 80 is also substantially aligned, along the Z axis, with: the inlet hole 50 of the cap 8, the inlet hole 60 of the first bi-adhesive layer 12 and the inlet hole 70 of the flexible layer 14.

The membrane 16 is shaped as a plurality of strips 82 adapted to close or block the air exhaust micro channels 5 in such a way that fluid flow through the membrane 16 is prevented, while gas (e.g., air) flow through the membrane 16 is allowed.

Between adjacent strips 82 of the membrane 16, a plurality of apertures 84 are formed so that, when the membrane 16 is arranged above the flexible layer 14, the wells 4 formed in the body 2 are not covered by the membrane 16. In this way, the wells 4 are optically accessible from the outside of the microfluidic device 1000, 1001.

The need for optical accessibility of the wells 4 requires that also the cap 8, the first bi-adhesive layer 12, the flexible layer 14, and the second bi-adhesive layer 20 (when present), must be transparent with respect to at least the wavelength of interest to the assay. Should the membrane 16 be transparent to the same chosen wavelength, the apertures 84 are not necessary.

During use, the wells 4 can be filled with a liquid by using, for example, a micropipette (not shown), by injecting a liquid sample at the inlet region 30, which is accessible through the inlet channel 3 formed by the inlet holes 50, 60, 70 and 80. The liquid thus injected flows from the inlet region 30, by capillary action, through the main channel 6a and the cross channels 6b, and enters the wells 4.

Any air that may have been trapped within the network of channels 6 and the wells 4 during manufacturing is free to flow out of the wells 4 through the outlet regions 32, the air exhaust micro channel 5, and the membrane 16. Liquid entering the wells 4 may also fill the empty spaces of the air exhaust micro channels 5, but it cannot flow through the membrane 16. The liquid is thus confined within the microfluidic device 1000, 1001 (and, in particular, within the wells 4).

According to one embodiment, all of the wells 4 are, during use of the microfluidic device 1000, 1001, fluidically isolated from one another, in such a way that cross talk between wells 4 is avoided (e.g., the liquid present in a first well 4 does not mix with an adjacent well 4). In the embodiment of FIG. 3a, 3b, fluidic isolation between adjacent wells 4, is guaranteed by the presence of the grooves 10 extending around the wells 4 and sealing the cap 8 to the body 2, particularly in the region between adjacent wells 4 along the Y axis.

In the embodiment of FIG. 4a, 4b, fluidic isolation between adjacent wells 4 is guaranteed by the presence of the second bi-adhesive layer 20, which adheres to the first surface 2a of the body 2, in particular in the region between adjacent wells 4 along the Y axis, thus interrupting any undesired fluidic path among wells 4 along the Y axis.

The other fluidic paths between wells 4 are interrupted by means of the protrusions 74. In order to obtain a good (i.e., watertight) contact between the protrusions 74 and the body 2, the flexible layer 14 is pressed, during use, toward the body 2 in such a way that the protrusions 74 act as pistons contacting the first side 2a of the body 2, entering the cross channels 6b, and thus closing the cross channels 6b. The wells 4 are, in this way, completely fluidically isolated from one another.

Figure 9:
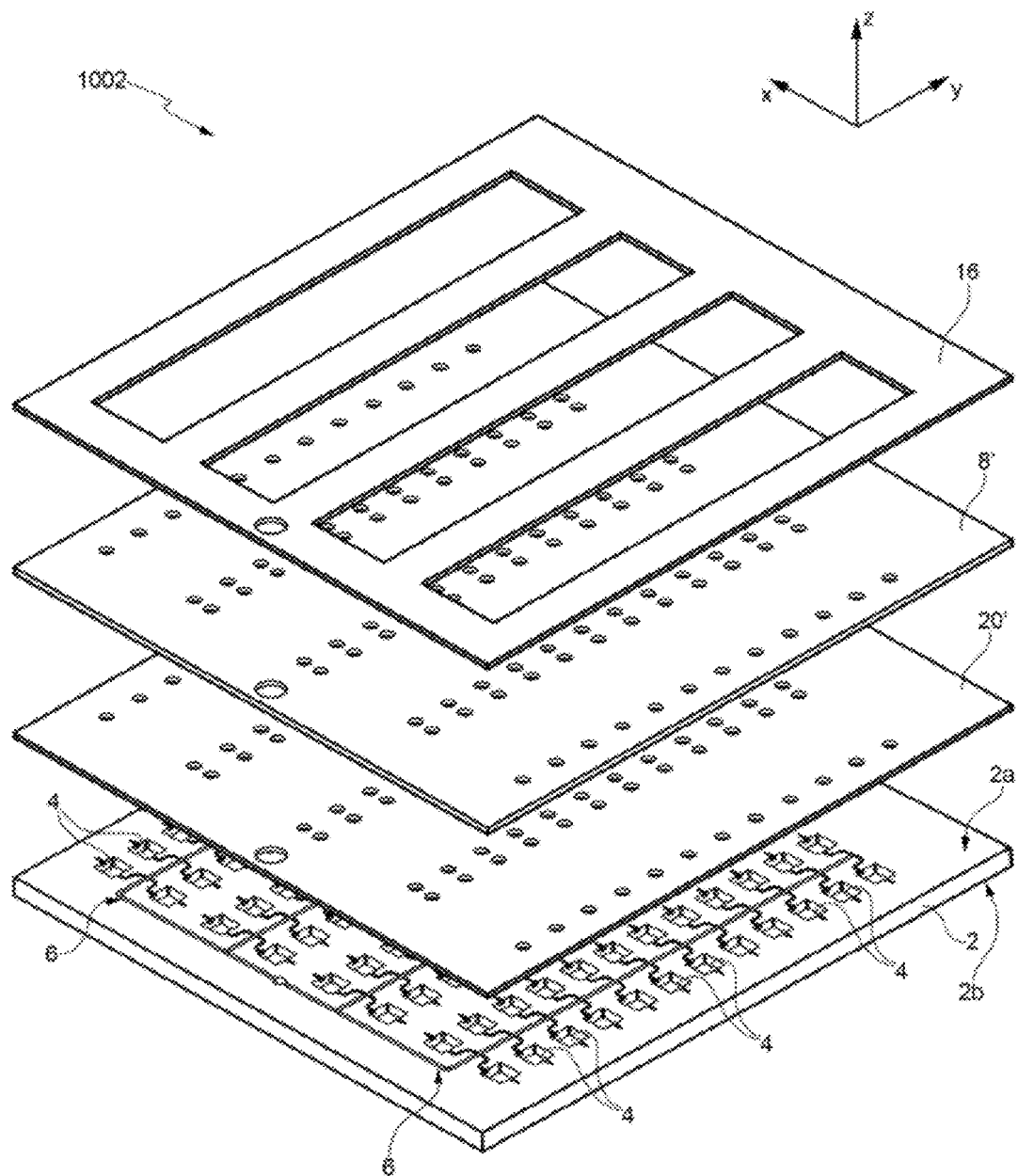
FIG. 9 shows an expanded view of a further embodiment of the microfluidic device.

FIG. 9 shows a further embodiment of the present invention. Elements of FIG. 9 that are the same as previously described devices 1000 and 1001 are labeled with the same reference numbers and not further described.

According to an embodiment of FIG. 9, a microfluidic device 1002 comprises the body 2 having the first side 2a and the second side 2b opposite to one another. The body 2 is, according to an aspect of the present invention, of semiconductor material, for example silicon. However, other material may be used for the body 2, for example plastic materials (e.g., biocompatible plastic), or glass, or even other materials according to need. The body 2 houses, at the first side 2a: at least a couple of wells 4 (preferably, a plurality of wells 4); the inlet region 30 forming an entrance point for a fluid to be supplied to the wells 4; the main channel 6a fluidically connected to the inlet region 30; and at least a couple of secondary channels 6b (preferably a plurality of couples of secondary channels 6b) fluidically connecting the main channel 6a to a respective well 4.

The wells 4 extends within the body 2 for the depth $D_W$, the main channel 6a extends within the body 2 for the depth $D_{MC}$, the secondary channels 6b extend within the body 2 for the depth $D_{CC}$, such that $D_W > D_{MC} > D_{CC}$. Examples of values of the depths have been previously given.

According to FIG. 9, the flexible layer 14 is absent and the first bi-adhesive layer 12 is also absent. Given the small dimension of the channels 6 (in the micrometer range), the flow of the liquid is driven by capillary action until the liquid enters the wells 4. The different values of the depths $D_{MC}$, $D_{CC}$, and $D_W$, and in particular the fact that $D_W > D_{MC} > D_{CC}$ of the cross channels 6b, provides for the advantage that the fluid, once it has entered a certain well 4, cannot escape from the respective well 4 (the fluid is trapped within each one of the wells 4). In this way, cross contamination between wells 4 is considerably reduced, or even eliminated, even without the presence of the flexible layer 14 having the protrusions 74.

According to a further embodiment, the microfluidic device 1002 is provided with the flexible layer 14. According to this embodiment, the possibility of cross contamination between wells 4 is further reduced even if the microfluidic device is kept in an upside down position or shaken.

According to a further embodiment, the body 2 of the microfluidic device 1002 is covered with a cap 8'. The cap 8' is configured in the same as the cap 8 (i.e., it is provided with the apertures 54) only if flexible layer 14 is included. Otherwise, in the absence of the flexible layer 14, the cap 8' is without the apertures 54. The same teaching applies to the bi-adhesive layer 20' (analogous to the second bi-adhesive layer 20 and having the same function).

According to a further embodiment, the adhesive layer 20' is not present, and the cap 8' is coupled to the body 2 by means of glue. Grooves 10 may be present, analogously to what already described with reference to FIGS. 3a and 3b.

Figure 10A:
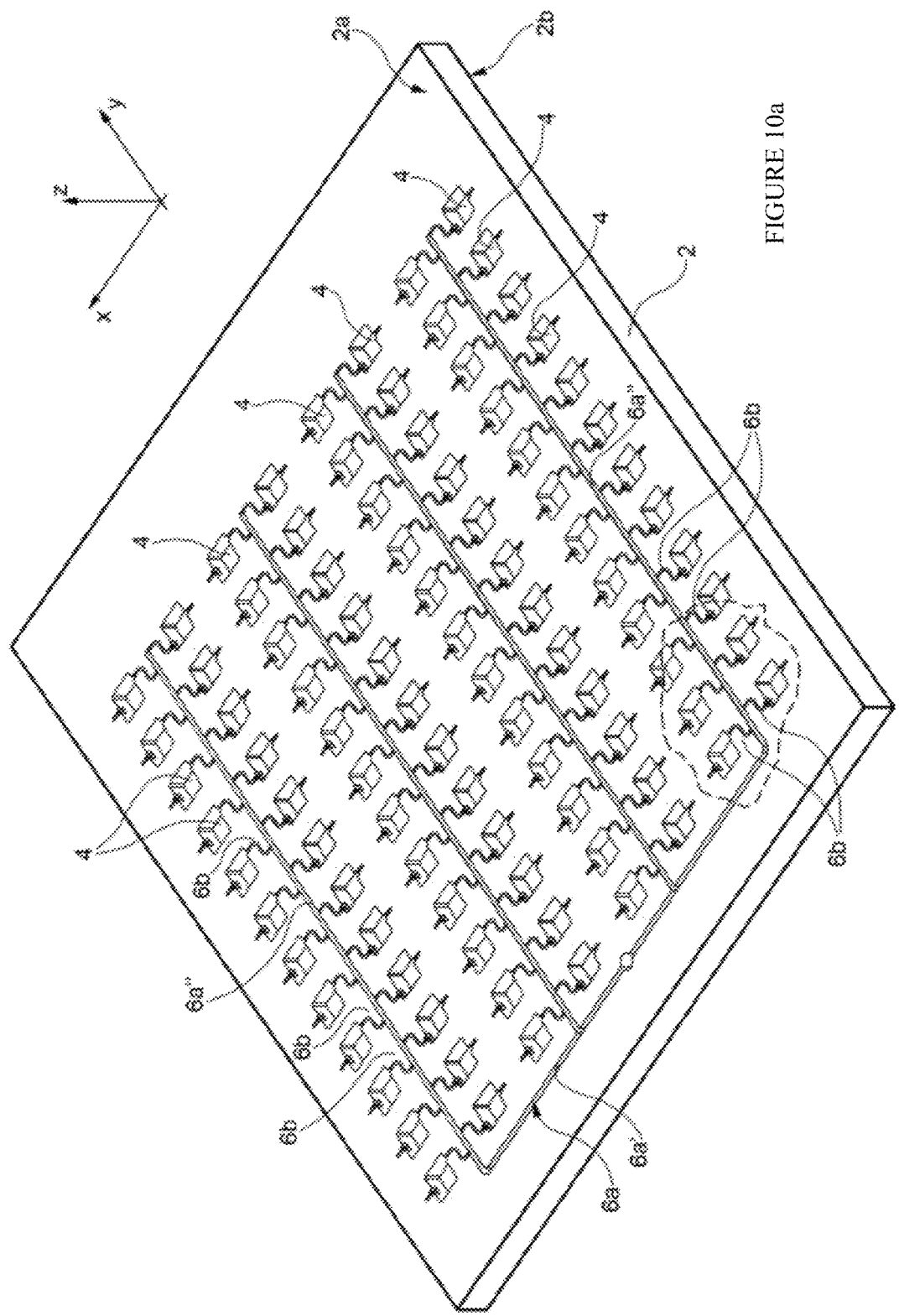
FIG. 10a shows a perspective view of a body of the microfluidic device, according to a further embodiment.
Figure 10B:
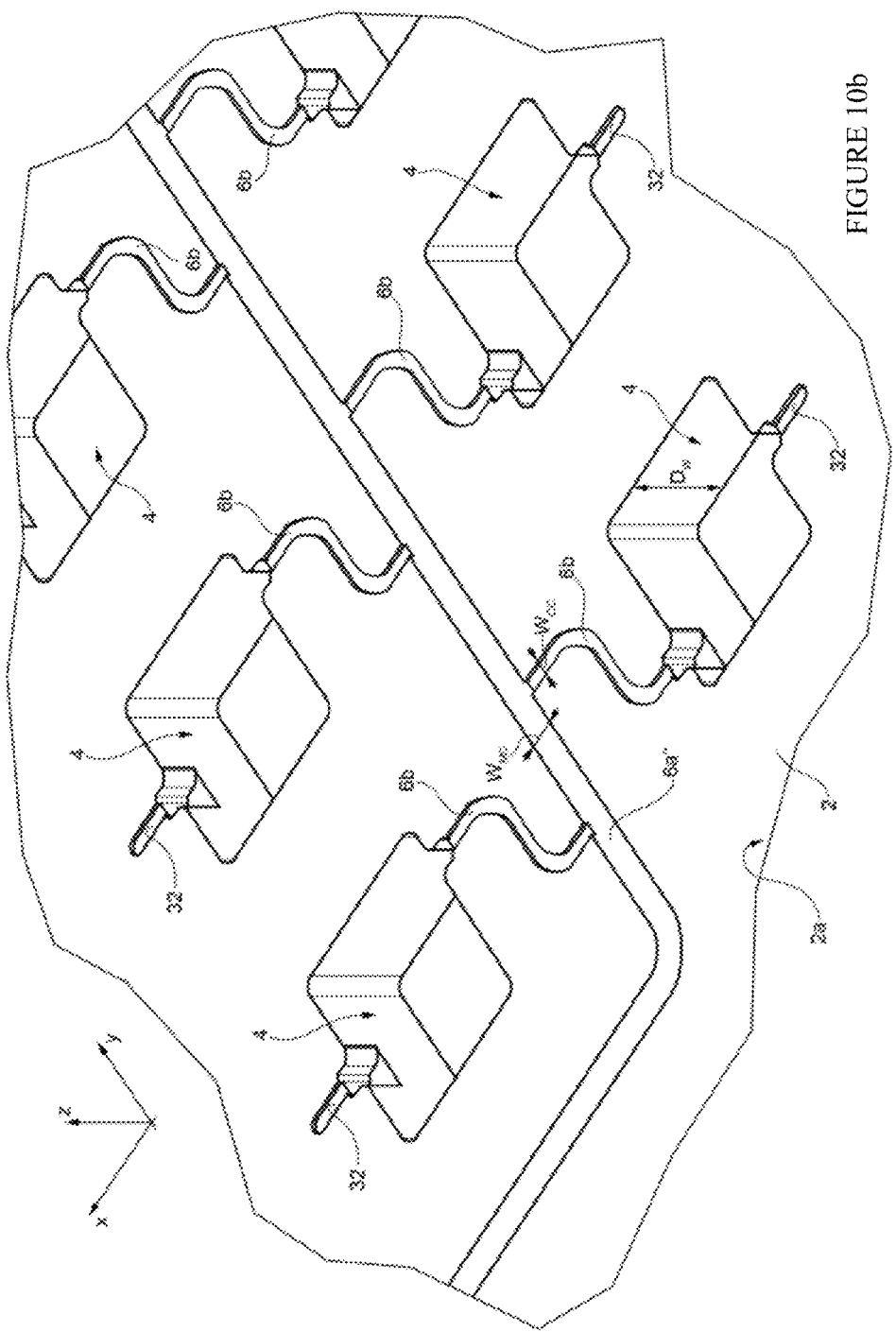

FIG. 10a, 10b show a still further embodiment of the body 2. According to FIG. 10a, 10b, the wells 4 are organized as an array having one or more rows (along a X axis) and one or more columns (along a Y axis). In a preferred arrangement, the wells 4 are substantially aligned in both the X and Y axes, although this is not essential and the wells could be staggered in one or more axes.

However, the cross channels 6b that connect a well 4 to the sub-branch 6a" are not aligned to one another along a same direction parallel to the X axis. Instead, the cross channels 6b extending on a same side of the sub-branch 6a" of the main channel 6a are staggered with respect to the cross channels 6b extending on the opposite side of the same sub-branch 6a" of the same main channel 6a. In this way, cross contamination among wells 4 is further reduced since the fluidic path from a well 4 to another well 4 via channels 6b is increased in length.

The embodiment of FIG. 10a, 10b can be applied to the microfluidic device 1000, 1001, i.e., in combination with the flexible layer 14 provided with protrusions 74, so as to further reduce cross-contamination among wells 4. In this situation, according to an aspect, one protrusion 74 for each cross channel 6b is provided.

According to another aspect, one protrusion 74 may be provided for two staggered cross channels 6b, provided that the two staggered cross channels 6b are sufficiently close to one another to allow a single protrusion 74 to contact both of them and to enter, when a sufficient pressure is applied on the flexible layer 14, within the staggered cross channels 6b so as to obstruct the staggered cross channels 6b.

It is clear that the teaching of the embodiment of FIG. 10a, 10b may be applied in general to a different configurations wherein the sub-branch 6a" and the main branch 6a' coincide (e.g., the main channel comprises a single, straight, branch as in FIG. 10a), or they can be separate branches (as in FIG. 1a).

Figure 11:
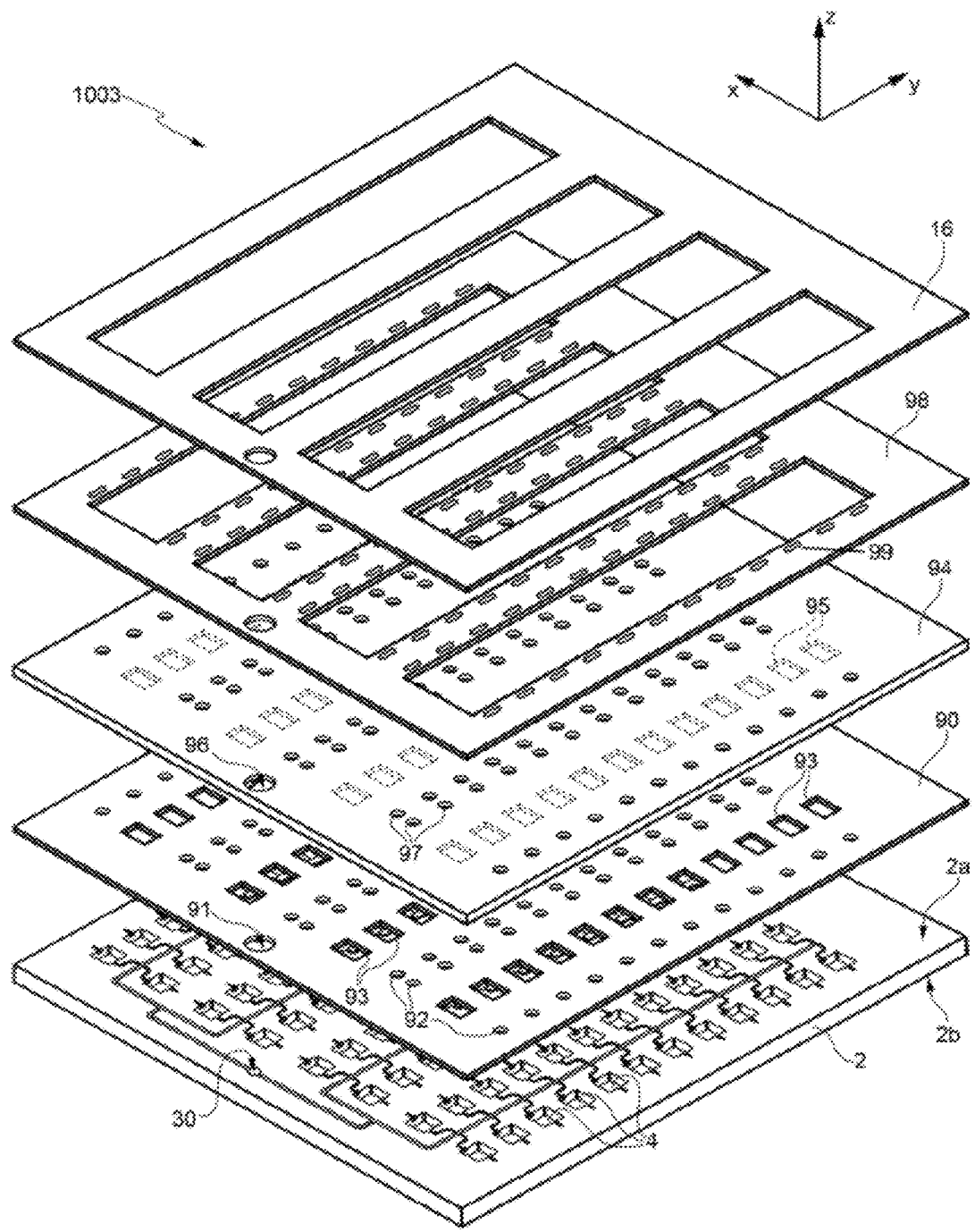
FIG. 11 is an expanded view of a microfluidic device according to another embodiment.

FIG. 11 shows a further embodiment of a microfluidic device 1003, according to a perspective, exploded, view.

The microfluidic device 1003 comprises a body 2 analogous to the body 2 described with reference to FIG. 2a, 4a, 4b, or FIG. 10a and thus designated with the same reference number.

Above the first surface 2a of the body 2 is arranged a bi-adhesive layer 90. The bi-adhesive layer 90 comprises a plurality of openings formed completely through it, analogous to what already described with reference to the second bi-adhesive layer 20. In detail, an inlet hole 91 is formed through the bi-adhesive layer 90 and has a circular shape, or the shape chosen for the inlet region 30 of the body 2, or any other shape according to need. The inlet hole 91 is positioned such that, when the bi-adhesive layer 90 is arranged above the body 2, the inlet hole 91 is substantially aligned, along the Z axis, with the inlet region 30 of the body 2.

The bi-adhesive layer 90 further comprises a plurality of air exhaust holes 92, having e.g., a circular shape (however, other shapes, generally polygonal, are possible). The air exhaust holes 92 are positioned such that, when the bi-adhesive layer 90 is arranged above the body 2, each air exhaust hole 92 is arranged above, and in fluidic communication with, a respective air outlet region 32.

The bi-adhesive layer 90 further comprises a plurality of valve holes 93, having (from a top view) a polygonal shape, for example quadrangular shape, or a circular or oval shape. Each valve hole 93 is positioned such that, when the bi-adhesive layer 90 is arranged above the body 2, each valve hole 93 is arranged (when considered from a top view) between two wells 4 facing a same sub-branch 6a", above a region of the body 2 housing the two cross channels 6b directly fluidically coupled to the aforementioned wells 4 facing the same sub-branch 6a". To summarize, when the bi-adhesive layer 90 is arranged as shown in FIG. 11, the inlet hole 91 is substantially aligned with the inlet region 30, and the air exhaust holes 92 are substantially aligned with respective air outlet regions 32.

The bi-adhesive layer 90 adheres to the surface 2a of the body 2 in the same way as described with reference to the second bi-adhesive layer 20 of FIG. 2a.

Above the bi-adhesive layer 90 is a cap 94. The cap 94 is a flexible layer, e.g. made of elastomeric or flexible material. Other materials may be used for the cap 94, for example the same materials described for the flexible layer 14 (e.g., PDMS or PMMA or silicone and the like). According to an embodiment, the cap 94 is made of a flexible, bio-compatible material.

The cap 94 adheres to the bi-adhesive layer 90. In this way, the bi-adhesive layer 90 is arranged between the cap 94 and the body 2, and couples the cap 94 to the body 2.

The cap 94 is provided with protrusions 95 (analogous to the protrusions 74 in FIG. 7a, 7b) configured to extend through respective valve holes 93 of the bi-adhesive layer 90. The cap 94 has a minimum thickness (protrusions 95 excluded) in the range from 100 μm to 500 μm, for example of about 150 μm.

According to an embodiment, the protrusions 95 have each a thickness slightly higher than the thickness of the bi-adhesive layer 90 (for example equal to the thickness of the bi-adhesive layer 90 plus the depth $D_{CC}$ of the cross channels 6b). According to another embodiment, the protrusions 95 have each a thickness substantially equal to the thickness of the bi-adhesive layer 90. In general, the protrusions 95 are configured such that, during use, when a sufficient pressure is applied to the cap 94 along the Z axis towards the body 2, the protrusions 95 enters the cross channels 6b. The protrusions 95, thus, have the same function as the protrusions 74 already described.

The cap 94 is moreover provided with an inlet hole 96 formed in a region of the cap 94 such that, when the cap 94 is arranged above the body 2 and the bi-adhesive layer 90, the inlet hole 96 is substantially aligned, along the Z axis, with the inlet region 30 of the body 2 and the inlet hole 91 of the bi-adhesive layer 90.

The cap 94 is moreover provided with air exhaust holes 97, substantially aligned, when the cap 94 is arranged above the body 2 and the bi-adhesive layer 90, with the air exhaust holes 92 of the bi-adhesive layer 90.

Above the cap 94 is a further bi-adhesive layer 98. Above the bi-adhesive layer 98 is a membrane, which is the same as the membrane 16 already described (and thus indicated with the same reference number), adapted to act as a gas/liquid separator. The bi-adhesive layer 98 acts as an interface between the cap 94 and membrane 16, to couple the cap 94 to the membrane 16.

In order to allow an air flow to pass through the membrane, the bi-adhesive layer 98 is provided with a plurality of air exhaust holes 99, each of them being substantially aligned when assembled with the air exhaust holes 97 (and thus also with the air exhaust holes 92 and the air outlet regions 32).

The bi-adhesive layer 98 need not be provided with valve holes analogous to the valve holes 93 of the bi-adhesive layer 90. According to an aspect of the present invention, the bi-adhesive layer 98 has the same shape already described for the membrane 16 (i.e., it is provided with a number of apertures 98' analogous to the apertures 84 of the membrane 16). This is particularly useful when the microfluidic device 1003 is used for fluorescence-based biological analysis (as described later on). In fact, the adhesive layer may be slightly opaque, thus creating a barrier (or a scattering region) for the light supplied to the wells 4, and/or for the light outputted by the wells 4, during fluorescence-based analysis.

Figures 12A, 12B:
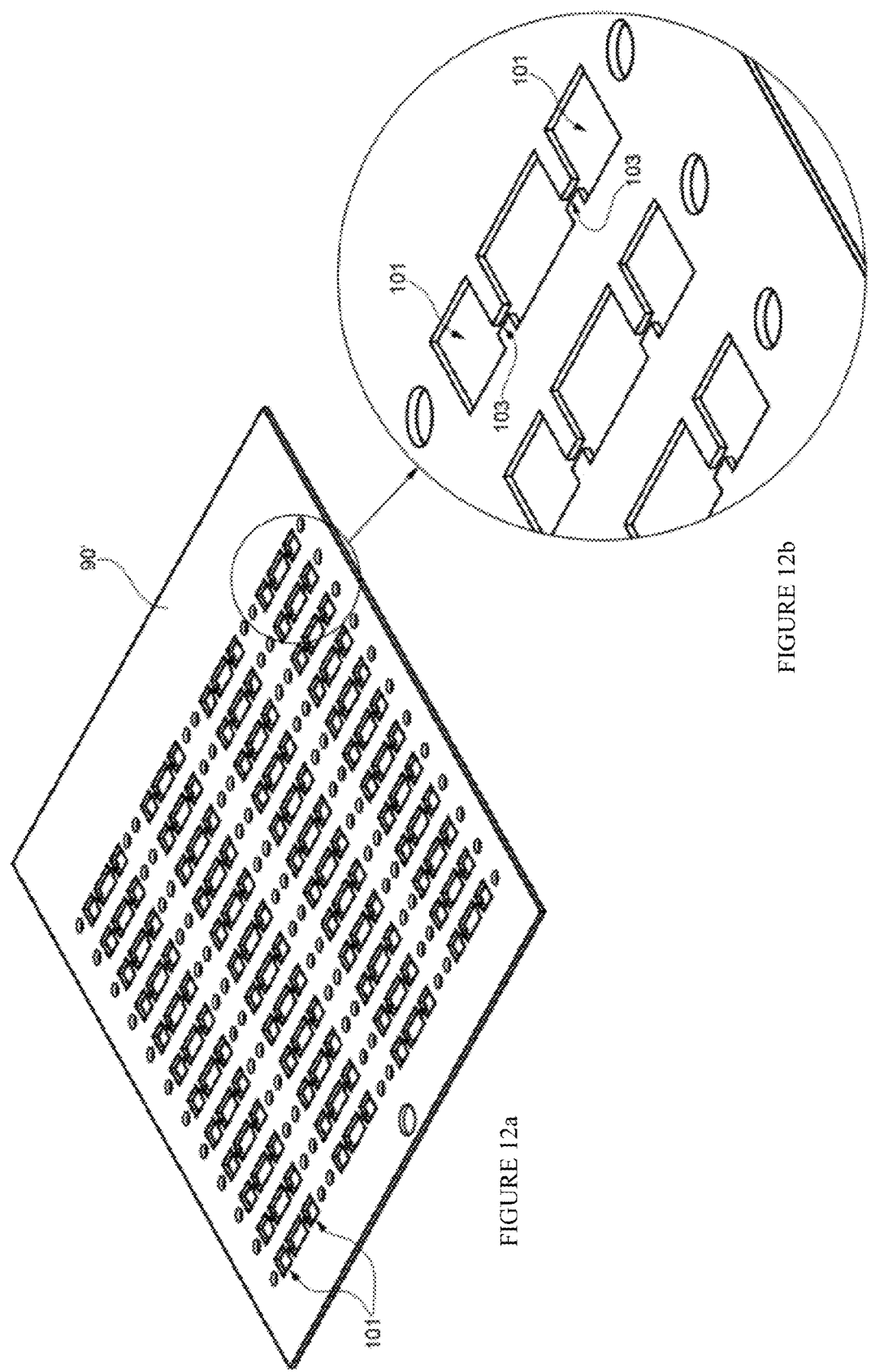

FIGS. 12a and 12b show a further embodiment of a bi-adhesive layer 90' that reduces the interference of the bi-adhesive layer with the light directed toward, and coming from, the wells 4.

In particular, FIG. 12b is an enlarged view of the encircled portion of FIG. 12a. The bi-adhesive layer 90' of FIG. 12a, 12b comprises the features of the bi-adhesive layer 90 of FIG. 11 and further comprises openings 101 configured to be aligned, when the bi-adhesive layer 90' is arranged above the body 2 as shown in FIG. 11, with respective wells 4. In particular, each well 4 is aligned, at least partially, along the Z axis, with a respective opening 101. In this way, the bi-adhesive layer 90' does not interfere with the optical path toward and from the wells 4.

Optionally, the bi-adhesive layer 90' further comprises openings 103 configured to be aligned, when the bi-adhesive layer 90' is arranged above the body 2 as shown in FIG. 11, with respective portions of the cross channels 6b, in particular the portion of the cross channels directly facing and entering the respective wells 4. In this way, also portions of the cross channels 6b are opened. This feature avoids possible obstruction of the cross channels 6b by the bi-adhesive layer 90'.

Figure 13:
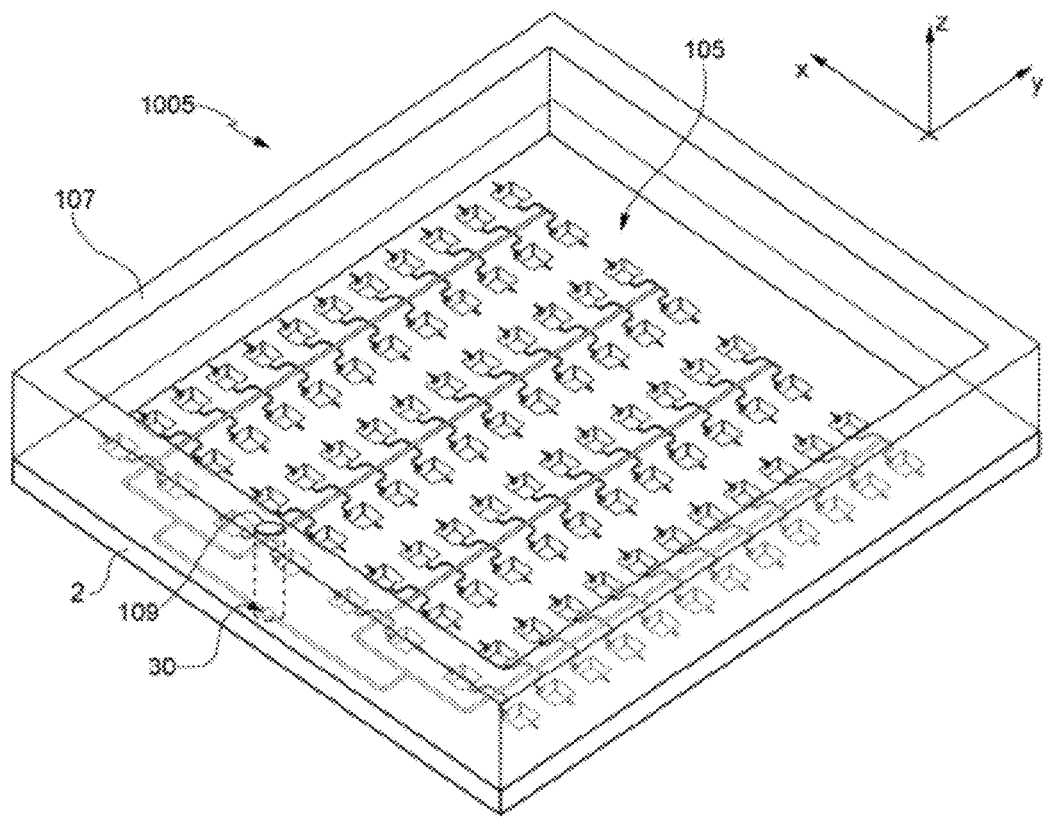
FIG. 13 shows a perspective view of a further embodiment of the microfluidic device.

According to a further embodiment, shown in FIG. 13, a microfluidic device 1005 comprises a reservoir 105, formed on the body 2. The reservoir 105 is formed by arranging a structure 107 defining a closed structure on the body 2, in such a way to enclose the microfluidic network (wells and channels) formed in the body 2. The structure 107 is made of rigid (e.g., PC, PMMA, PVC) or soft (e.g., PDMS) material, and coupled to the body 2 by means of glue, welds, clamps, or otherwise. According to one embodiment, the glue is silicone adhesive, which can be dispensed precisely.

As visible in FIG. 13, the structure 107 is arranged above the inlet region 30 of the body 2 and is provided with an inlet hole 109 extending through the structure 107 for its entire thickness along the Z axis. The inlet hole 109 may have a shape that is chosen according to need. In particular, the inlet hole 109 is formed in such a way to allow fluidic access to the inlet region 30, so that, during use, a liquid can be injected to the inlet region 30 through the inlet hole 109. According to a preferred embodiment, the inlet hole 109 has a base area that is approximately the same as the area covered by the inlet region 30. According to another embodiment, the inlet hole 109 has a base area greater than the area covered by the inlet region 30, thus facilitating access to inlet 30.

Figure 14:
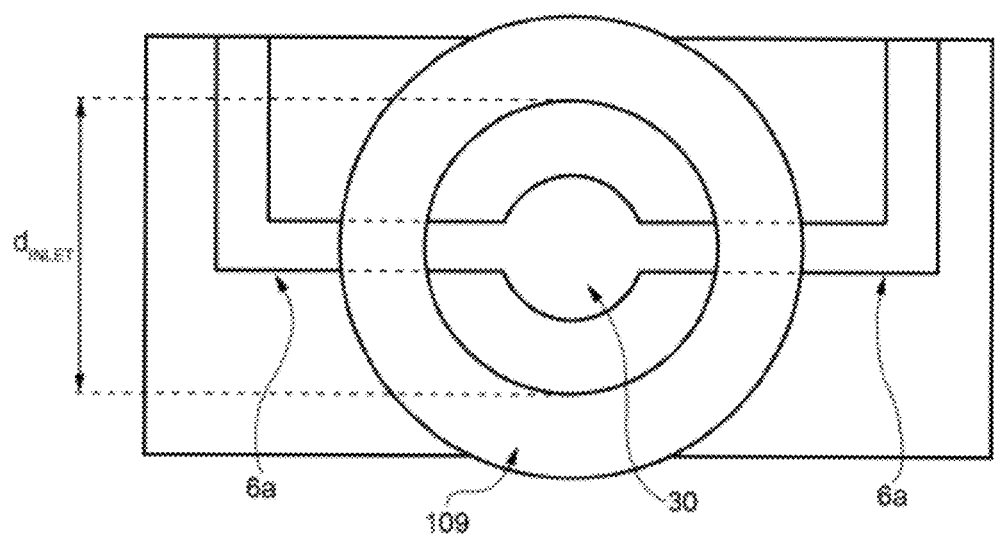
FIG. 14 is a top enlarged view of an inlet portion of the microfluidic device of FIG. 13, according to yet another embodiment.

FIG. 14 shows, from a top view, an enlarged view of a portion of the body 2 and the structure 107 arranged over the body 2 where the inlet hole 109 and the inlet region 30 are visible. According to the embodiment of FIG. 14, the inlet hole 109 has a circular base and forms a round-shaped reservoir for containing a liquid that has to be supplied to the inlet region 30. For example, the inlet hole 109 of FIG. 14 contains some tens of microliters, e.g., 30 μl. The diameter $DIA_I$ of the base of the inlet hole 109 is chosen according to need, for example in the range from 1 to 10 mm, in particular 1-2 mm.

Figure 15:
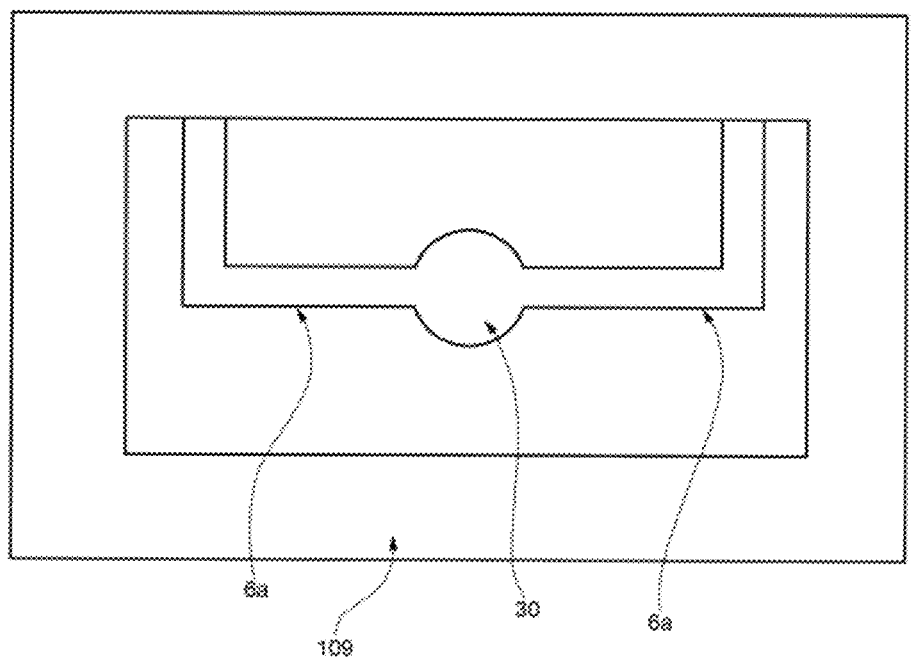
FIG. 15 is a top enlarged view of an inlet portion of the microfluidic device of FIG. 13, according to a further embodiment.

FIG. 15 shows, from a top view, an enlarged view of a portion of the body 2 and the structure 107 arranged over the body 2 where the inlet hole 109 and the inlet region 30 are visible, according to another embodiment. According to FIG. 15, the base of the inlet hole 109 has a quadrangular shape, in particular rectangular, with sides of one or more millimeters, for example 1.5 mm×10 mm.

The embodiments of FIG. 13-15 provide a reservoir (i.e., the inlet hole 109), which eases the operation of supplying a liquid sample to the inlet region 30 so as to fill the wells 4 through the channels 6.

Figure 16:
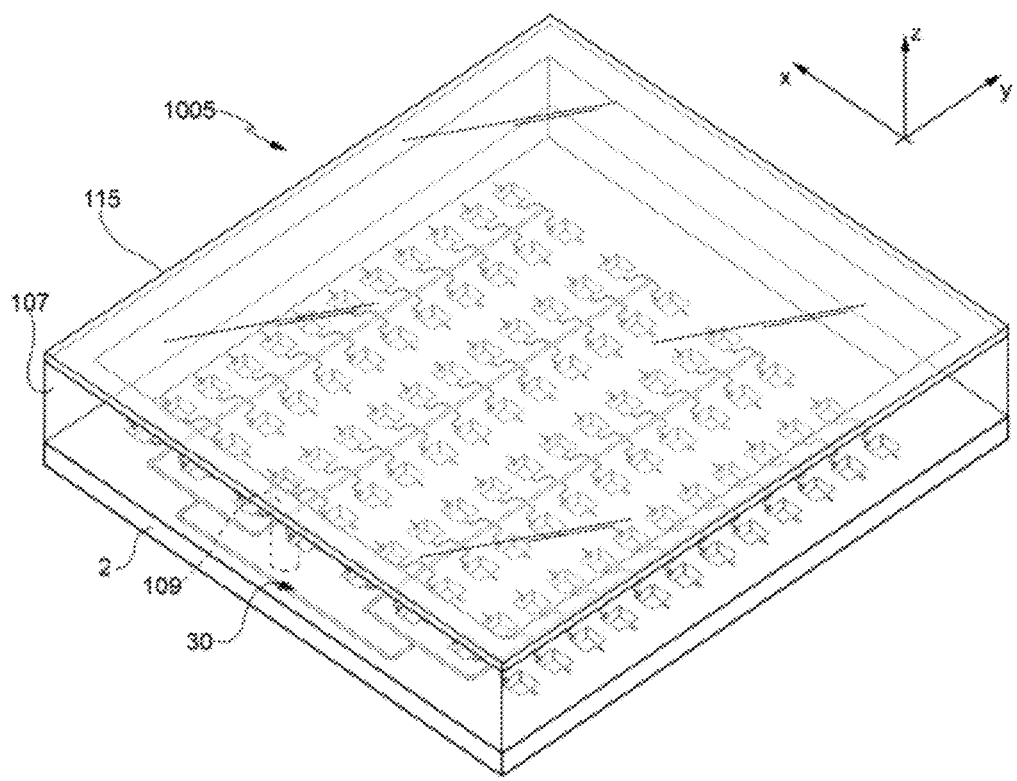
FIG. 16 shows the microfluidic device of FIG. 13 when loaded with a mineral oil for preventing evaporation.

With reference to FIG. 16, once the liquid sample has been supplied to the wells 4, a mineral oil is poured, pipetted, or supplied in any other way, above the body 2 within the closed region or chamber defined by the structure 107. In this way, the mineral oil completely covers the wells 4 and the channels network 6, acting as a vapor barrier to prevent evaporation and internal condensation of the wells 4. The type of mineral oil to be used is chosen according to need, for example, the mineral oil may be chosen of a type configured to act as means for facilitating thermal transfer through the wells 4.

A transparent covering layer 115 may then be arranged above the structure 107 so as to protect the mineral oil from leaking or spilling from the closed reservoir defined by the structure 107.

We have illustrated in FIG. 13-16 a single reservoir for holding oil over all wells. However, it is also possible to subdivide structure 107 (not shown), such that every well 4 has its own oil chamber above it, thus further minimizing the chance of contamination. Alternatively, groups of wells can be outfitted with separate reservoirs, e.g., for duplicate or triplicate sample wells.

Figure 17:
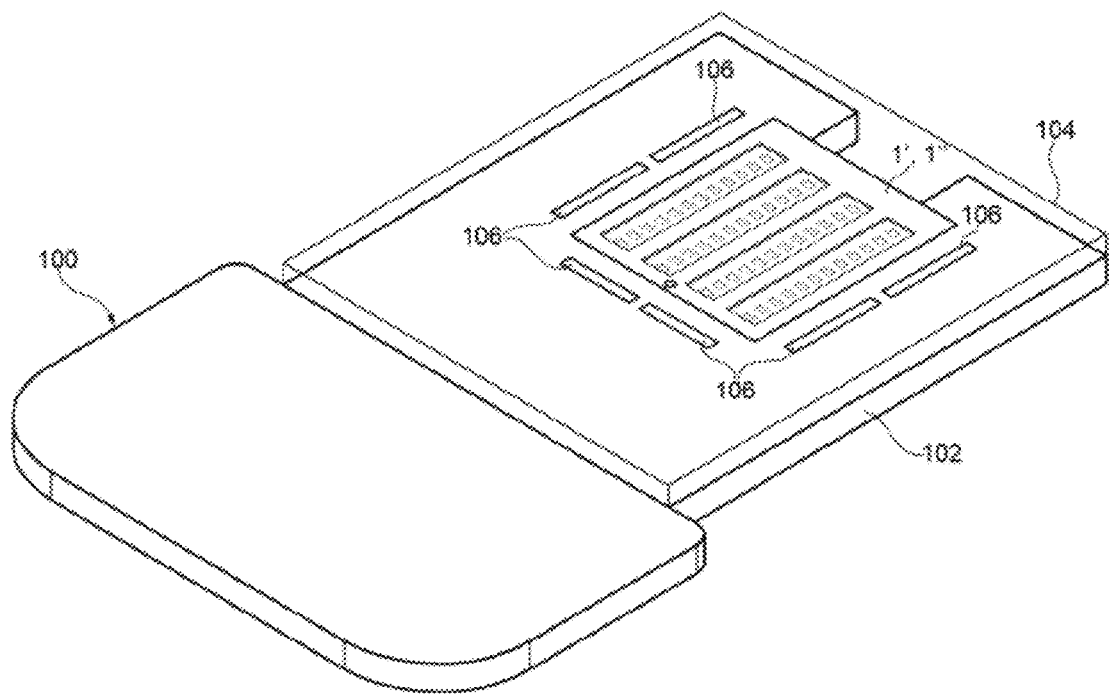
FIG. 17 shows a perspective view of a holder device adapted to house, during use, the microfluidic device of FIG. 1b, FIG. 2b, FIG. 9 and/or FIG. 11.

FIG. 17 shows a device holder 100 configured to hold the microfluidic device 1000, 1001, 1003 (when assembled as shown, e.g., in FIGS. 1b and 2b), and to exert a pressure on the flexible layer 14 in such a way that the protrusions 74 contact the first surface 2a of the body 2 and enter within the cross channels 6b, thus acting as pistons and closing the cross channels 6b. The protrusion 74, being formed of an elastomeric or flexible material (e.g., PDMS or silicone rubber), are sufficiently deformable to enter the cross channels 6b when sufficient pressure is applied.

Figure 20:
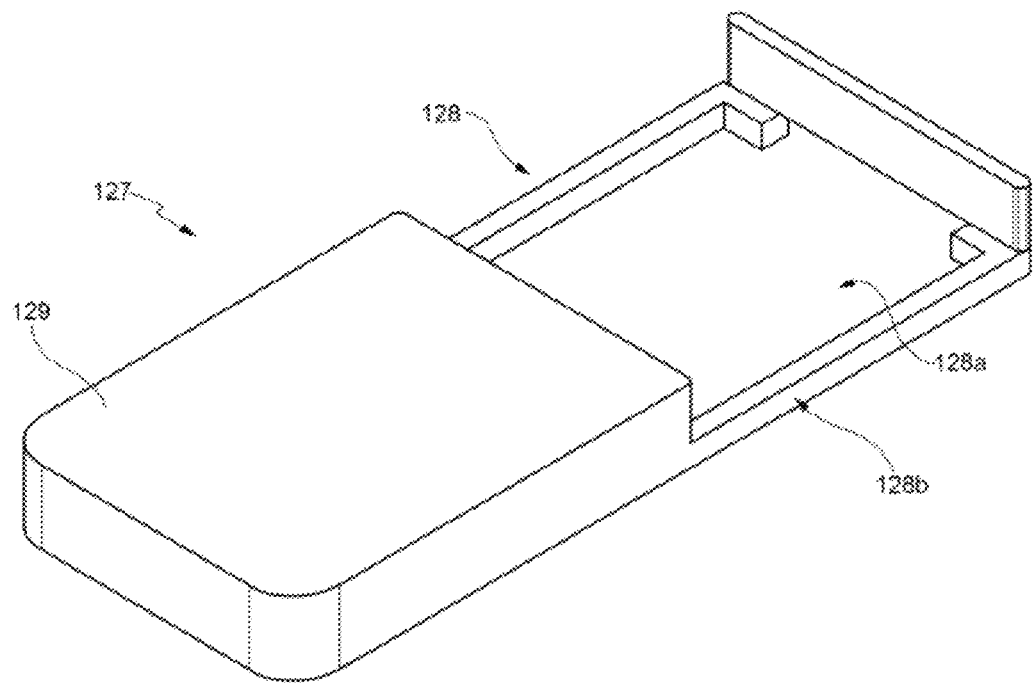
FIG. 20 shows a perspective view of a holder device adapted to house, during use, the microfluidic device of FIG. 9 and/or FIG. 13.

The device holder 100 can also be used to hold the microfluidic device 1002 since it provides a practical way of favoring the adherence of the stacked layers and to safely manipulate the microfluidic device 1002. However, since the microfluidic device 1002 does not comprises the flexible layer provided with protrusions 74, the device holder 100 is not optimal for holding the microfluidic device 1002. A further device holder, particularly suitable for holding the microfluidic device 1002, is shown in FIG. 20 and described later.

In the following, use of the device holder 100 will be described with particular reference to the embodiments of the microfluidic device 1000, 1001, without limiting the use of the device holder 100 to these specific embodiments.

The device holder 100 comprises a base portion 102 adapted to sustain the microfluidic device 1000, 1001, and a cover portion 104, adapted to couple to the base portion 102 in such a way that the microfluidic device 1000, 1001 is sandwiched between the base portion 102 and the cover portion 104. To this extent, coupling elements 106 are provided, which can be cantilevered snap fitting hooks, clamps, screws, or the like.

In an embodiment of the present invention, the cover portion 104 is made of plastic transparent material. In particular, the cover portion 104 is transparent with respect to at least a certain wavelength (in the visible or non-visible frequency range), even more in particular, to the same wavelength to which the first bi-adhesive layer 12, the flexible layer 14, and the second bi-adhesive layer 20 (when present) are transparent. According to an embodiment of the present invention, the first bi-adhesive layer 12, the flexible layer 14, the second bi-adhesive layer 20 (when present), and the cover portion 104 are transparent to one or more wavelengths in the visible range.

Figure 18:
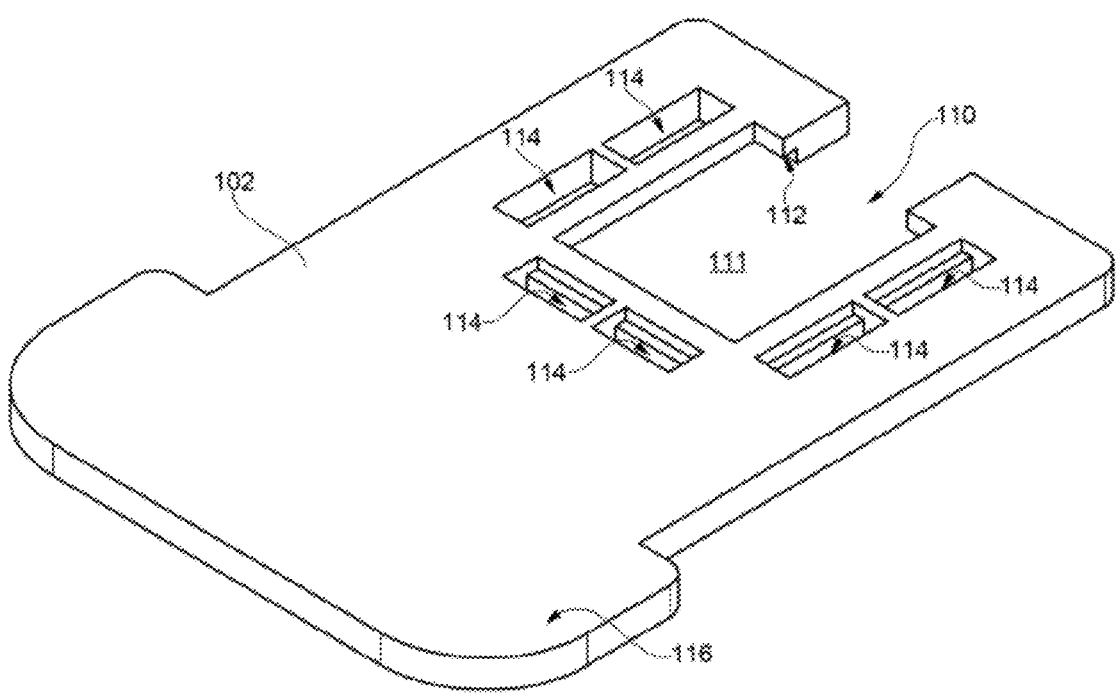
FIG. 18 is a first portion of the holder device of FIG. 17.

FIG. 18 shows the base portion 102. The base portion 102 comprises a compartment 110 adapted to hold the microfluidic device 1000, 1001. The compartment 110 includes an housing aperture 111 and a frame 112, surrounding, at least partially, the housing aperture 111. The frame 112 has a step-like shape or ledge, so that a peripheral region of the second side 2b of the body 2 lies in contact with the frame 112. The microfluidic device 1000, 1001 is, in such a way as to be sustained by the frame 112. When the microfluidic device 1000, 1001 is placed within the compartment 110, both the top and the bottom of the microfluidic device 1000, 1001 are free for inspection.

The base portion 102 further comprises an handle portion 116, via which a user can handle the device holder 100.

The base portion 102 further comprises a plurality of coupling apertures 114 formed around the housing aperture 111 and the frame 112. The coupling apertures 114 are through holes, having (from a top view) a polygonal, for example quadrangular, shape. The coupling apertures 114 are configured to be coupled with hooks 124 of the cover portion 104 of the device holder 100.

Figure 19:
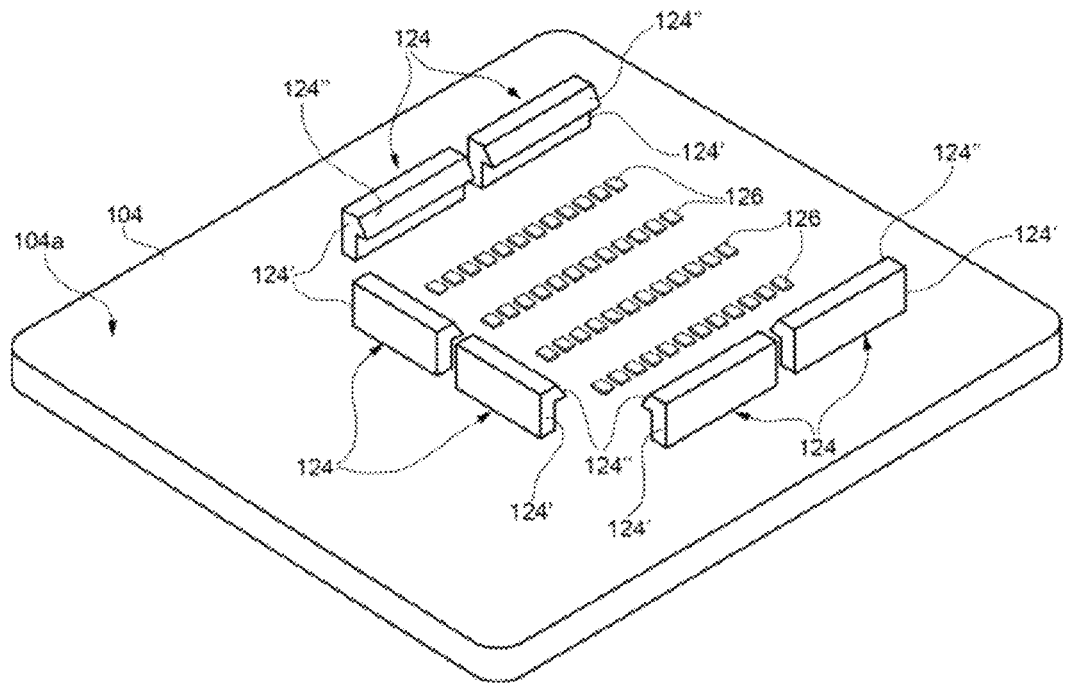
FIG. 19 is a second portion of the holder device of FIG. 17, adapted to couple with the first portion of FIG. 18.

FIG. 19 shows in greater detail an embodiment of the cover portion 104, provided with the hooks 124. The hooks 124 include a base 124' protruding from the cover portion 104 along a direction orthogonal with respect to the surface 104a of the cover portion 104, and a locking portion 124", extending, at a distance from the surface 104a, from the base 124' along a direction parallel to the surface 104a. Thus, hook 124 provides a cantilevered snap fit.

The cover portion 104 and the base portion 102 are coupled together, during use, by inserting the hooks 124 into the coupling apertures 114. The locking portion 124" of each hook 124 pass through the coupling apertures 114, but they cannot be easily released from the coupling apertures 114. In this way, the cover portion 104 is secured to the base portion 102 of the device holder 100 thus forming the coupling elements 106 of FIG. 17.

Furthermore, the cover portion 104 has the function of exerting a pressure on the flexible layer 14 so that the protrusions 74 close the cross channels 6b. To this extent, the cover portion 104 houses a plurality of bumps 126 such that, when the microfluidic device 1000, 1001 is arranged in the compartment 110 and the cover portion 104 is coupled to the base portion 102 (situation shown in FIG. 17), each bump 126 presses the flexible layer 14 in a region of the flexible layer 14 which corresponds to a respective protrusion 74. The actual thickness of the bumps 126 is chosen according to need, in such a way that a sufficient pressure on the flexible layer 14 is applied without excessive deformation of the flexible layer 14 and/or of the microfluidic device 1000, 1001 as a whole, which could cause damage to the microfluidic device 1000, 1001 or parts thereof.

During use, a liquid is supplied to the inlet region 30 of the microfluidic device 1000, 1001. During the liquid supplying step, the protrusions 74 are not pressed in such a way to close the cross channels 6b, so that liquid flow is not hampered by the protrusions 74 (i.e., the microfluidic device 1000, 1001 is not sandwiched by the base portion 102 and the cover portion 104). As previously described, the liquid enters the wells 4 through the network of channels 6. Once the wells 4 are filled (partially or completely, according to need) by the liquid (e.g., after a certain amount of time), a pressure is applied to the flexible layer 14, for example by use of the device holder 100 of FIG. 17-19. The wells 4 are, in this way, isolated from one another and cross-talking or cross-contamination is avoided.

FIG. 20 shows a device holder 127 according to a further embodiment of the present invention. Device holder 127 is particularly useful to hold the microfluidic device 1002 and/or the microfluidic device 1005. The device holder 127 comprises a compartment 128 adapted to hold the microfluidic device 1002, 1005. The compartment 128 includes an housing aperture 128a and a frame 128b, surrounding, at least partially, the housing aperture 128a. The frame 128b has a step-like shape, so that a peripheral region of the second side 2b of the body 2 lies in contact with the frame 128b. The microfluidic device 1002, 1005 is, in such a way, sustained or supported by the frame 128b. When the microfluidic device 1002, 1005 is placed within the compartment 128, both the top and the bottom of the microfluidic device 1002, 1005 are open for inspection. The device holder 127 further comprises a handle portion 129, by which a user can handle the device holder 127.

FIG. 21-28 relate, in general, to any one of the microfluidic devices previously described with reference to the respective embodiments. In particular, FIG. 21-28 relate the microfluidic devices 1000, 1001, 1002, 1003, 1005. In the following, reference to one or more of such embodiments is made using the wording microfluidic device 1000-1005.

Figure 21A:
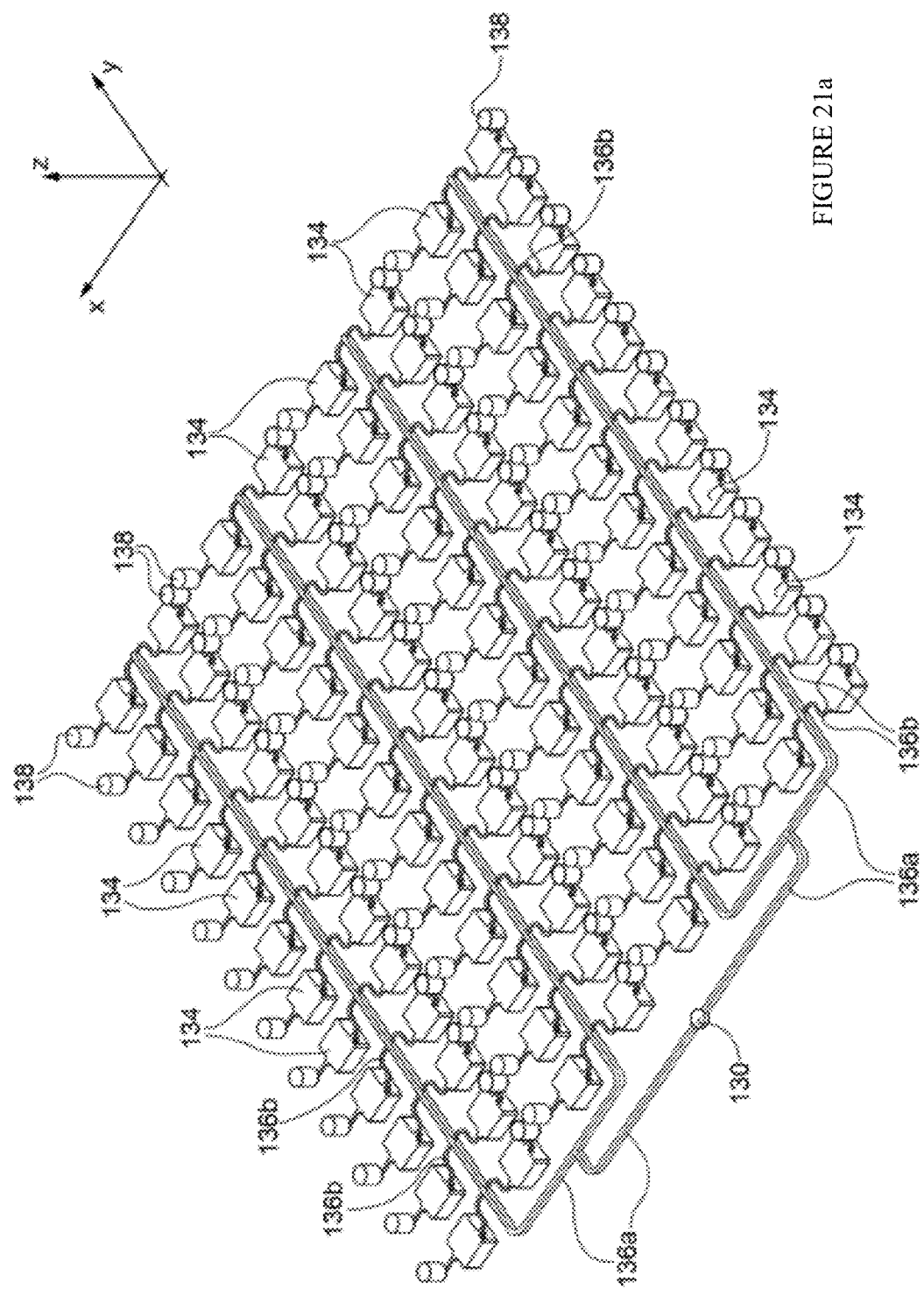
FIG. 21a shows only the fluidic domain of the microfluidic device according, for example, to the embodiment of the microfluidic device of FIG. 1a, 1b.
Figure 22A:
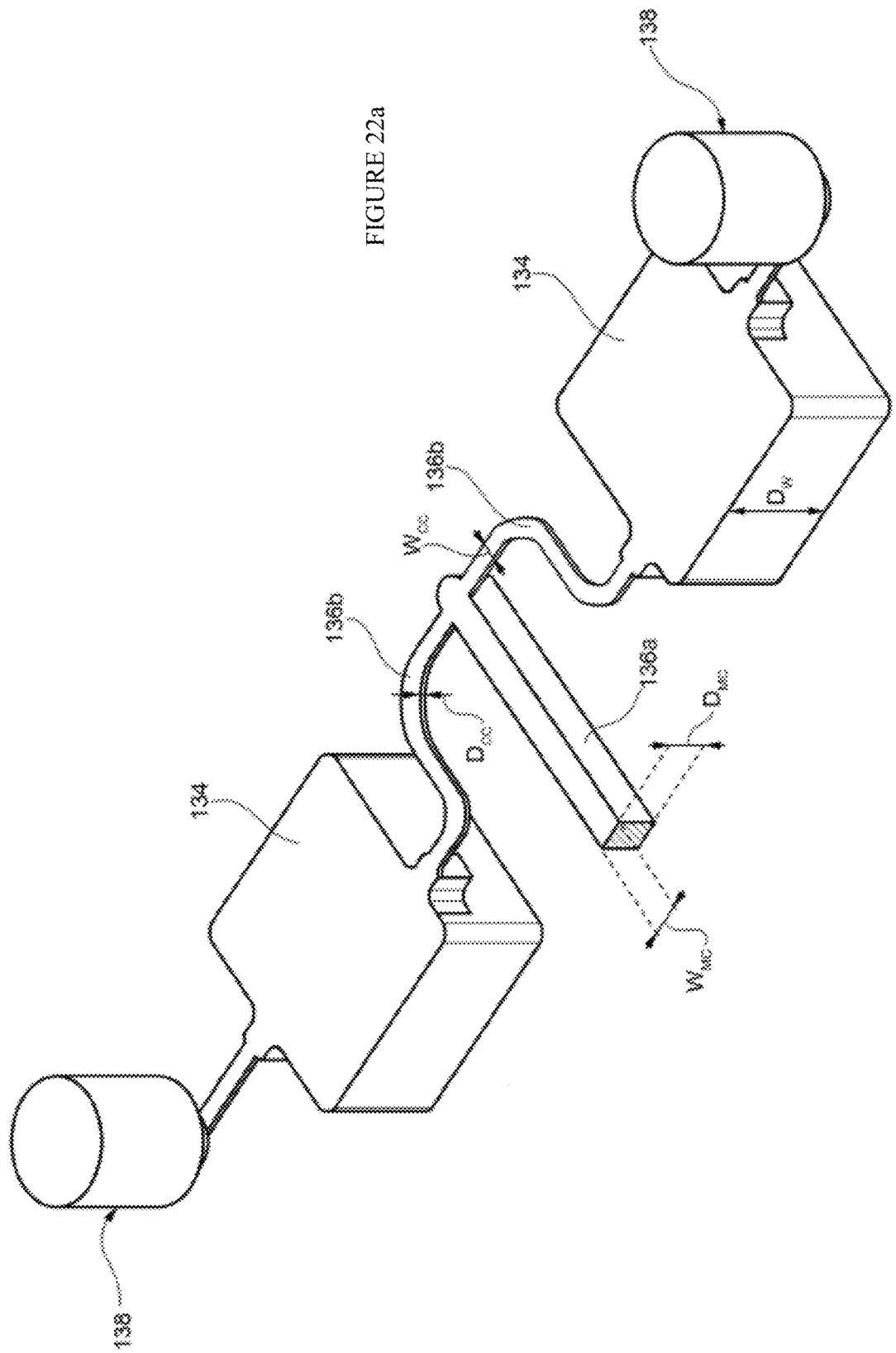

FIGS. 21a and 22a show a fluid domain of the microfluidic device 1000-1005, represented by a solid model. In detail, the fluidic domain of FIG. 21a relates to a microfluidic device 1000-1005 including a body 2 of the type shown in FIGS. 3b and 4b; the fluidic domain of FIG. 22a relates to a microfluidic device 1000-1005 including a body 2 of the type shown in FIG. 10a, 10b.

The fluidic domain corresponds to the complementary volume of the microfluidic network of channels 6, wells 4, outlet regions 32, and air exhaust micro channels 5. The liquid volume of the inlet region 30 is designated in FIG. 21a, 22a by reference number 130; the liquid volume of the main channel 6a is designated in FIG. 21a, 22a by reference number 136a; the liquid volume of the cross channels 6b is designated in FIG. 21a, 22a by reference number 136b; the liquid volume of the wells 4 is designated in FIG. 21a, 22a by reference number 134; the liquid volume of the air exhaust micro channels 5 and the air outlet regions 32 is designated in FIG. 21a, 22a by reference number 138.

Figure 21B:
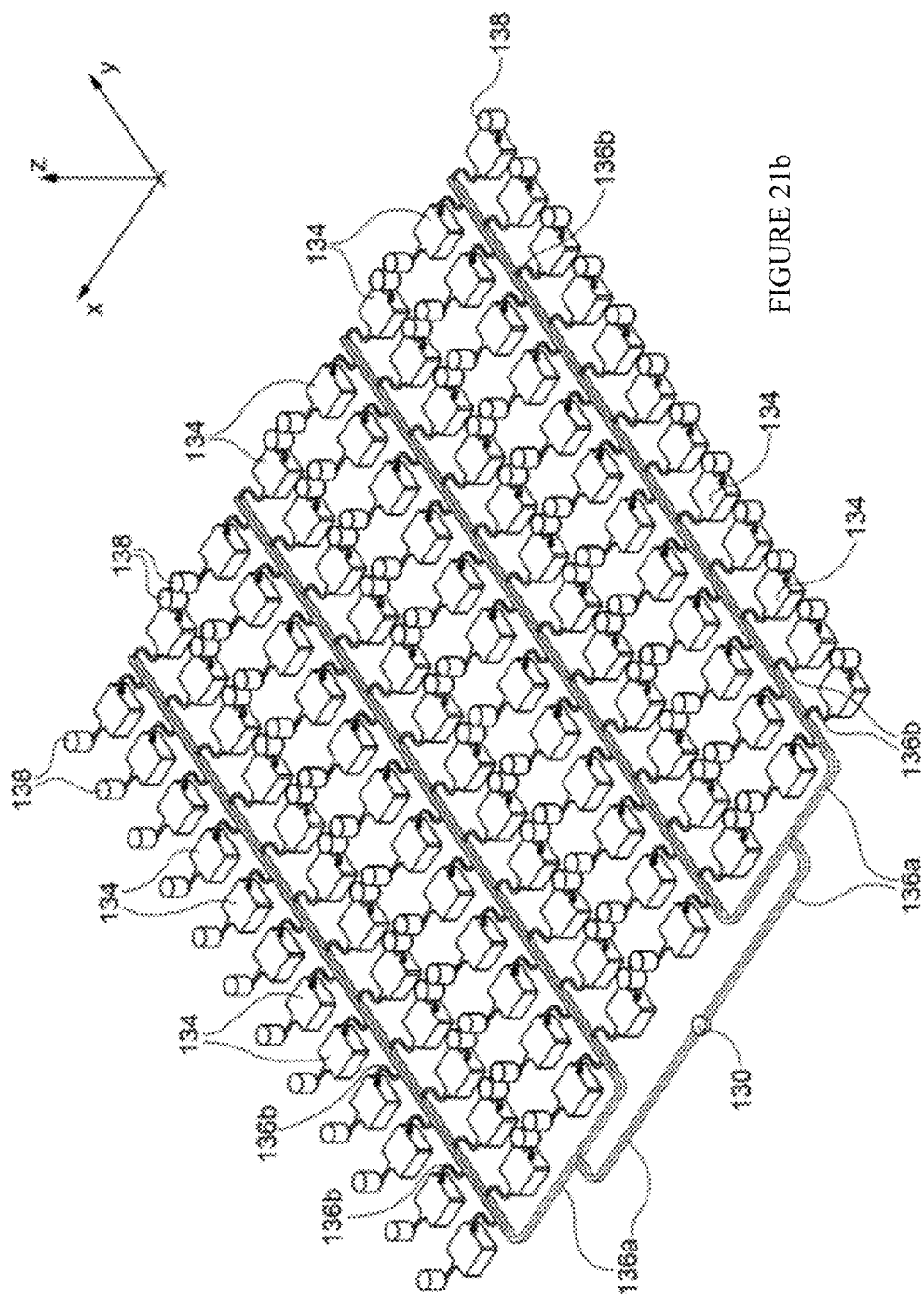
FIG. 21b shows the fluidic domain of the microfluidic device according a microfluidic device including a body of the type shown in FIG. 10a, 10b.
Figure 22B:
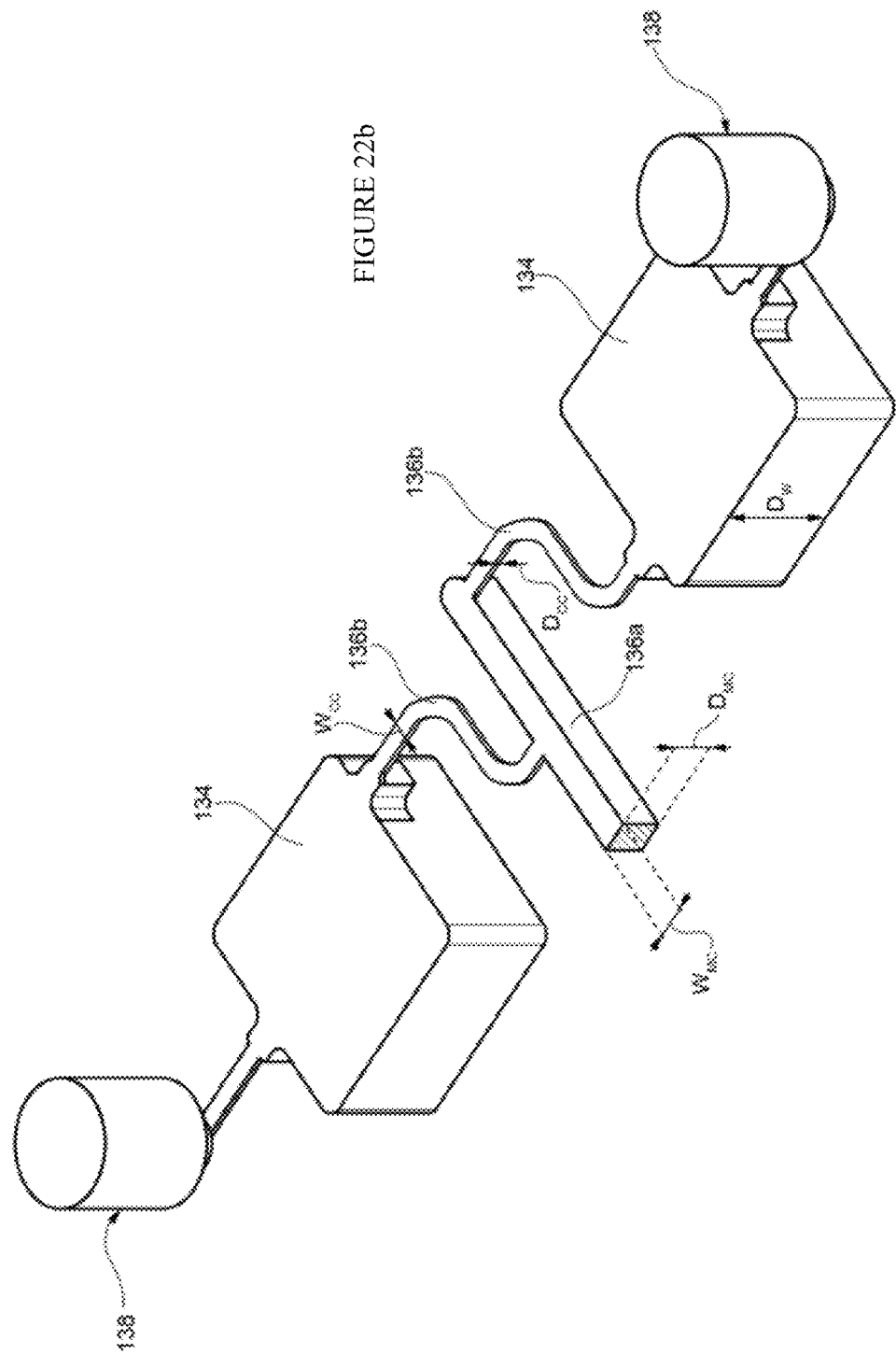
FIG. 22b shows an enlarged portion of the fluidic domain of FIG. 21b.

To evaluate the pressure drop due to the fluidic resistance faced by the liquid filling the aforementioned channels 6, wells 4, and air exhaust micro channels, a simplified model of the fluid domain is considered, as shown in FIG. 21b, 22b, which shows a portion of the fluidic domain of FIG. 21a and, respectively, 22a.

The simplified fluid domain of FIG. 21b, 22b includes the volumes 134 of a couple of wells 4, the volumes 136b of related cross channels 6b, the volumes 138 of air exhaust micro channels 5 and air outlet regions 32, and the volume 136a of a trunk of the main channel 6a.

Discretization of the fluid domain of FIG. 21b, 22b into a finite volume model allows us to compute a fluidic simulation of the microfluidic device 1000-1005, applying boundary conditions. The boundary conditions applied to the fluid domain are summarized in the following.

The liquid considered has the same properties as water at ambient temperature of 25° C., and ambient pressure $P_{amb}$ (i.e., $P_{amb}$=1 atm) during the sample loading at the inlet region 130. An inlet sample flow rate of about 40 μl/min was considered, corresponding to an inlet velocity in the main channel 6a of 0.011 m/s. The adhesion of the fluid to the walls defining the fluidic domain is considered by imposing all components of fluid velocity to a value equal to zero at the walls, which delimit the fluidic domain (no slip boundary conditions). The outlet condition of the fluidodynamic environment is obtained applying the environment pressure at the gas/liquid separator membrane 16.

The pressure drop computed by simulation shows that the relative pressure distribution within the microfluidic device 1000-1005 varies from a maximum value of about 1.7·103 Pa at the main channel 6a to a minimum value of about zero at the air exhaust micro channels 5 (the given values are referred to relative pressure, i.e. the difference between local and ambient pressure).

The pressure within the cross channels 6b is maximum where the cross channels 6b intersect the main channel 6a (1.7·103 Pa) and minimum where the cross channels 6b intersect the wells 4 (4.2·102 Pa). The pressure within the wells 4 is of about 4.2·102 Pa.

The simulation allows us to compute the overpressure (pressure drop) from the atmospheric value needed to flow the liquid from the inlet region 30 to the air exhaust micro channels 5. The overpressure value is due to localized pressure drops generated by fluid viscosity and localized pressure resistances due to section variation and fluidic path variations (restrictions and enlargements).

The maximum pressure drop is located at the cross channels 6b, where there is a consistent reduction of the channel section, and, consequently, the fluid increases its own velocity and main pressure loss occurs. The velocity distribution of the fluid within the fluidic domain of FIG. 21, 22, is maximum at the cross channels 6b, where there is a channel section reduction, and at the air exhaust micro channels. The whole pressure drop required to fill the system with the fluid (here, as said, water) has been simulated as being about 20 mbar. The local resistance opposed to the fluid during its flow into the network of channels 6 is negligible.

The microfluidic device 1000-1005 is, according to an embodiment of the present invention, a platform for DNA-based blood analyses, but can be used for any chemical assays, including antibody based assays, enzymatic assays, chemical assays and the like.

As an example, in DNA-based blood analyses, a sample typically containing white blood cells is broken up or lysed using chemical, thermal or biochemical means in order to liberate the DNA to be analyzed. The DNA is denatured by thermal, biochemical or chemical processes and amplified by an amplification reaction, such as PCR (polymerase chain reaction), LCR (ligase chain reaction), SDA (strand displacement amplification), TMA (transcription-mediated amplification), RCA (rolling circle amplification), NASBA (nucleic acid sequence based amplification), and the like. The amplification step allows the operator to avoid purification of the DNA being studied because the amplified product greatly exceeds the starting DNA in the sample.

If RNA is to be analyzed the procedures are similar, but more emphasis is placed on purification or other means to protect the labile RNA molecule. RNA is usually copied into DNA (cDNA) and then the analysis proceeds as described for DNA.

The amplification product undergoes some type of analysis, usually based on sequence or size or some combination thereof. In an analysis by microarray hybridization, for example, the amplified DNA is passed over a plurality of detectors made up of individual oligonucleotide detector fragments that are anchored, for example, within the wells 4 (which are the reaction chambers) of the microfluidic device 1000-1005. If the amplified DNA strands are complementary to the oligonucleotide detectors or probes, stable bonds will be formed between them (hybridization) under specific temperature conditions. The hybridized detectors can be read by observation using a wide variety of means, including optical, electromagnetic, electromechanical or thermal means.

Other biological molecules are analyzed in a similar way, but typically molecule purification is substituted for amplification, and detection methods vary according to the molecule being detected. For example, a common diagnostic involves the detection of a specific protein by binding to its antibody. Such analysis requires various degrees of cell separation, lysis, purification and product analysis by antibody binding, which itself can be detected in a number of ways. Lipids, carbohydrates, drugs and small molecules from biological fluids are processed in similar ways. However, for simplicity, the following discussion is focused on nucleic acid analysis, in particular DNA analysis, as an example of a biological molecule that can be analyzed using the devices of the present invention.

The devices of the instant invention allow parallel and multiplex DNA analysis, including real time assays using, for example, four molecular beacon probes labeled with different color fluorophores in each well. In this way, a 12×8=96 array of wells can detect amplicons for as many as 384 different target sequences. Thus, massive parallel and multiplex processing is possible on the tiny device, yet cross contamination has been reduced, if not eliminated by the designs employed herein.

Figure 23:
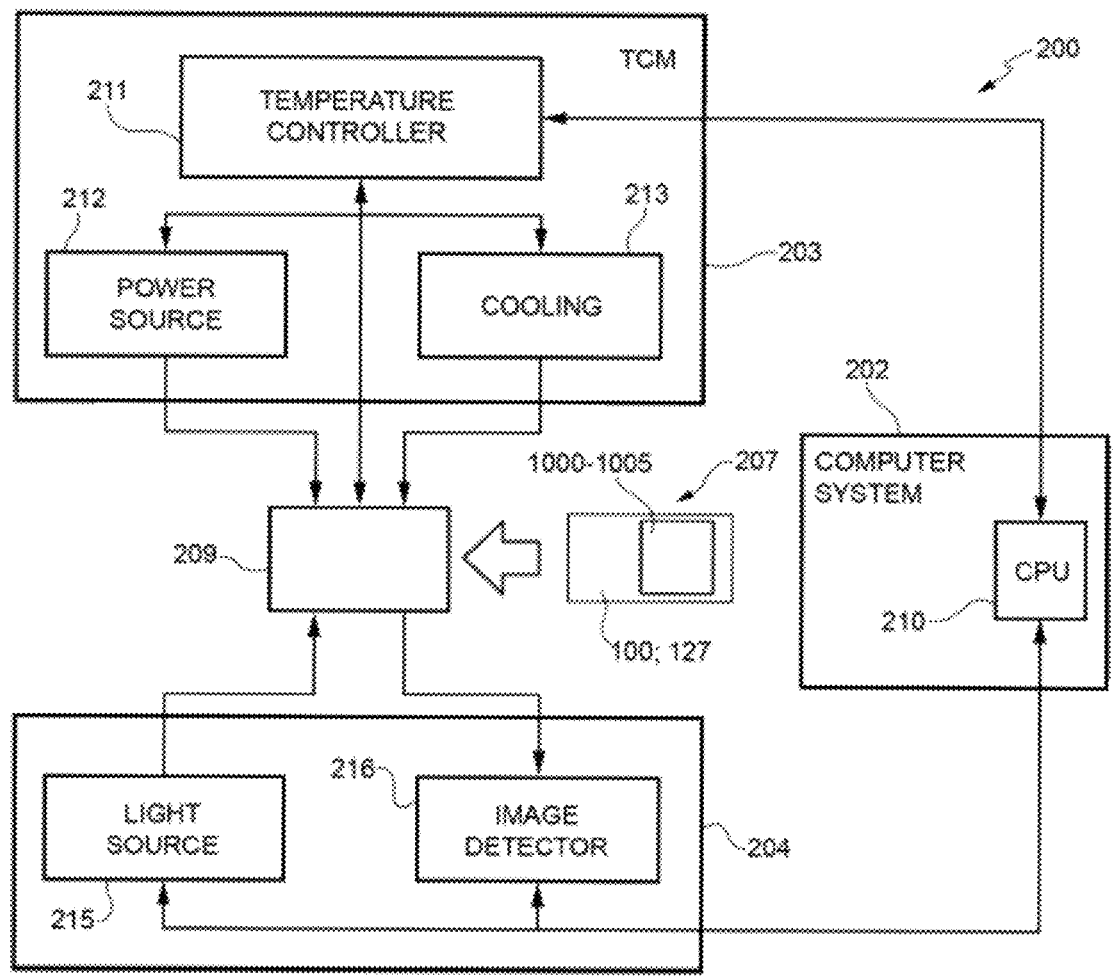
FIG. 23 is a system depiction of an apparatus for carrying out nucleic acid amplification according to one embodiment.

With reference to FIG. 23, a biochemical analysis apparatus 200 comprises a computer system 202, a temperature control module 203, and a reader device 204.

The biochemical analysis apparatus 200 is configured to interact with the device holder 100, 127 provided with the microfluidic device 1000, 1001, 1002, 1003, 1005, for performing biochemical analyses. In the following, the device holder with the microfluidic device will be referred to as cartridge 207, irrespective of the particular embodiment of the device holder and/or the microfluidic device. The cartridge 207 is loadable into a receptacle 209 for coupling with the temperature control module 203 and the reader device 204.

The temperature control module 203 and the reader device 204 are both controlled by a processing unit 210 of the computer system 202. The temperature control module 203 includes a temperature controller 211 and a power source 212. The temperature controller 211 is configured to receive a temperature signal from a temperature sensor (described below) formed integrated within the microfluidic device 1000-1005, or generally coupled to the microfluidic device 1000-1005.

The temperature control module 203 may also include a cooling element 213, e.g. a Peltier module or a fan coil, which is controlled by the temperature controller 211 and is thermally coupled to the microfluidic device 1000-1005 when the cartridge 207 is loaded in the receptacle 209.

The power source 212 and the cooling element 213 are operable by the temperature controller 211 respectively to deliver power to heater(s) (also described below) formed integral with the microfluidic device 1000-1005, or thermally coupled to the microfluidic device 1000-1005, and to cool the microfluidic device 1000-1005 in order to set an operating temperature in accordance with a temperature profile (defined by the chosen PCR thermal cycling).

In one embodiment, the reader device 204 is configured to perform optical detection of reaction products in the wells 4 of the microfluidic device 1000-1005, as hereinafter described. In particular, the reader device 204 includes a light source 215 for illuminating the wells 4 of the microfluidic device 1000-1005 with light at an excitation wavelength; and an image detector 216, configured to receive fluorescence radiation emitted from the wells 4, in response to the light at one or more excitation wavelengths. To this end, the layer(s) arranged above the body 2 (as previously described) are transparent to both the excitation wavelength(s) and the wavelength of the emitted fluorescence radiation.

However, it is understood that other ways to carry out detection are available in the known art and can be exploited, in place of optical detection. For example electrochemical detection can be performed.

Figure 24:
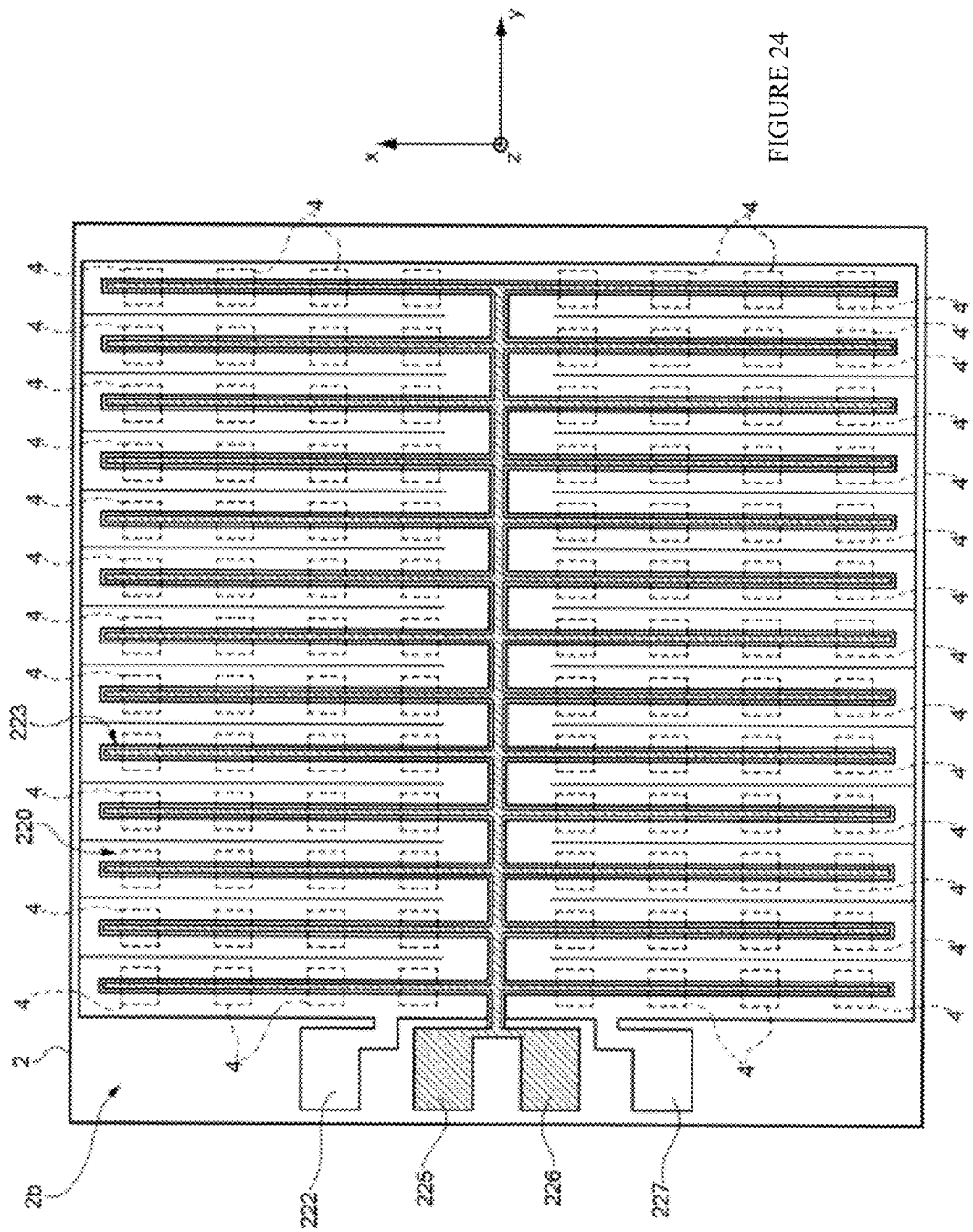
FIG. 24 shows a back-side view of the microfluidic device according to any one of the embodiments of the microfluidic device, comprising an heater and/or a temperature sensor.

FIG. 24 illustrates the body 2 from a bottom view (second side 2b, opposite to the first side 2a), showing in detail an embodiment of an integrated heater 220 and which can be used with any of the devices described herein.

The heater 220 is formed at the second side 2b of the body 2 and forms a thermal path, which develops on the second side 2b of the body 2. According to another embodiment, not shown, the thermal path develops (at least partially) inside the body 2.

Irrespective of the embodiment of the heater 220, the heater 220 includes an electric path configured to generates heat by Joule effect. The electric path is formed by a continuous strip (made of a material such as Al, AlCu, or other metallic, alloys or conductive materials), extending from a first conductive pad 227 to a second conductive pad 222. The electric path of the heater 220 is formed in such a way that all the wells 4 are uniformly heated to the desired temperature(s) during use.

In FIG. 24 the electric path of the heater 220 is shown as extending (when observed from the bottom, along the Z direction) substantially between wells 4 adjacent along the Y direction, only partially overlapped, along the Z axis, with the wells 4. The heater 220 thus has the shape of a rake or comb, which is reflected again on the opposite side.

A temperature sensor 223 is formed vertically aligned (i.e., aligned along the Z axis) with the wells 4. The temperature sensor 223 is formed by a plurality of strips extending on the second side 2b of the body 2 from a third and a fourth pad 225, 226. The temperature sensor 223 is arranged above (or below) the second side 2b of the body 2 substantially aligned, along the Z axis, with the wells 4. The temperature sensor 223 extends on the second side 2b in the regions of the second side 2b not covered by the heater 220. The temperature sensor 223, which is known per se, is made of metallic materials with a higher electrical resistance than the heater, for instance of two orders of magnitude more resistive than the heater.

When the cartridge 207 is loaded into the receptacle 209 (FIG. 23), the heater 220 is connected, through the pads 221, 222, to the power source 212 for receiving electrical power, and the temperature sensor 223 is connected through the pads 225, 226, to the temperature controller unit 211 for providing a temperature signal indicative of the temperature to which the wells 4 are heated/cooled.

The design/layout of the heater 220 can be optimized according to any particular configuration of the microfluidic device 1000-1005 and arrangement of the wells 4, in order to achieve the desired temperature profiles. The temperature sensor 223 is preferably arranged under the wells 4.

The body 2 is made, according to this embodiment, of a thermally conductive material, such as undoped silicon. In this way the heat generated by the heater 220 is transferred easily to the wells 4 through the body 2. The vertical distance (measured along the Z axis) between the heater 220 and the bottom of the wells 4 ranges between 100 µm and 350 µm, for example equal to 300 µm.

Figure 25:
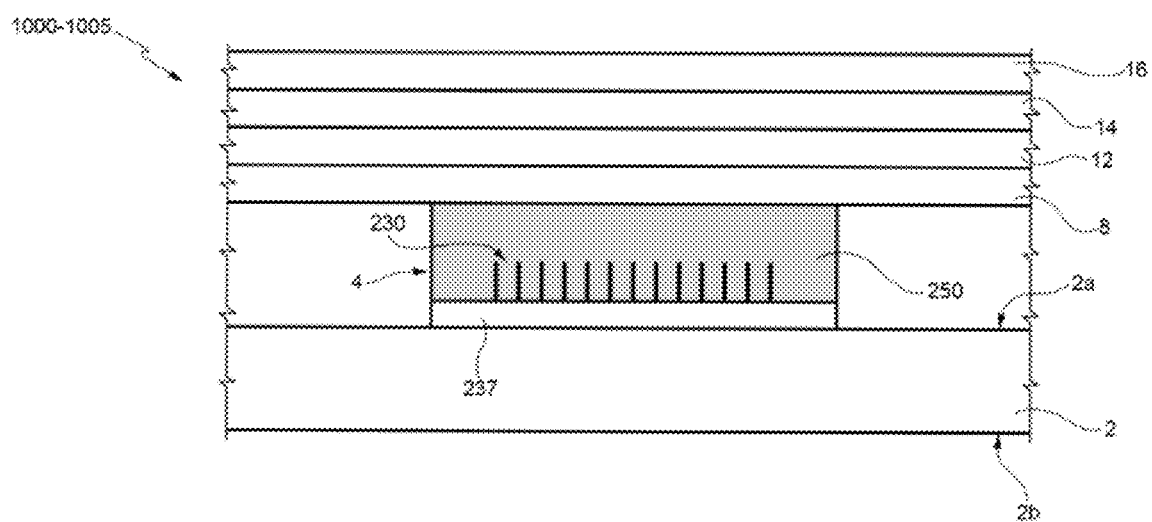
FIG. 25 is a cross sectional view of a portion of the body of a microfluidic device according to any one of the embodiments of the microfluidic device.

For use of the microfluidic device 1000-1005 as a microarray for biochemical analysis, in particular for PCR reactions, DNA probes 230 are arranged within the wells 4, as schematically shown in FIG. 25, which shows a section view of a well 4. According to an embodiment, all the wells 4 of the microfluidic device 1000-1005 contain DNA probes 230; according to another embodiment, only some of the wells 4 contain DNA probes 230, and the other wells are for various control samples. The probes 230 in a well 4 may be different from the probes 230 in another well 4, or the same probes 230 may be used, according to need.

According to one embodiment, the plurality of nucleic acid probes 230 in the wells 4 are single strand deoxy-oligonucleotides, grafted to the bottom of the wells 4. The bottom of the wells 4 may have been treated in such a way that grafting of probes 230 is enhanced. For example, as shown in FIG. 25, a passivation layer 237 may have been formed within the wells 4.

Probes 230 are adapted to hybridize to target DNA at a specific hybridization temperature when a reaction, such as nucleic acid amplification, is carried out in the wells 4. The probes can be all of the same type within a given well, or different probes can be laid down at addressable locations, as desired. Alternatively, detection can be via molecular beacon probes free in solution, and thus bottom of well 4 may not have bound probes thereon.

Hereinafter reference will be made to a nucleic acid analysis process including PCR. As it is known, PCR is a cyclical process involving a series of enzyme-mediated reactions whose final result are identical copies of the target nucleic acid. A raw biological sample is preliminarily processed by conventional steps of cell separation or purification and cell lysis. Then, the sample is added to a solution comprising enzymes (typically a DNA polymerase such as TAQ), primers, the four nucleotides (collectively referred to as dNTPs), cofactor, buffer, and e.g., a fluorescent dye capable of binding to double-helix DNA. Such dyes include, but are not limited to, bisbenzimide or indole-derived stains (Hoechst 33342, Hoechst 33258 and 4',6-diamidino-2-phenylindole), phenanthridinium stains (ethidium bromide and propidium iodide) and cyanine dyes (PicoGreen, YOYO-1 iodide, SYBR Green I and SYBR Gold). The fluorescent dye is preferably selected from the group of cyanine dyes and, in one example, is SYBR Green I. As an example, a dye-DNA complex that forms during the amplification process, adsorbs visible radiation selectively around a wavelength of 488 nm (blue) and emits visible radiation with a maximum of emission at 522 nm (green).

On the basis of the sequences of the probes 230 and of the primers, it is determined a hybridization temperature at which the probes 230 hybridize to complementary target DNA single strands, and an annealing temperature at which the primers bind to their complementary sequences on the target DNA. The probes 230 and the primers may be selected such that the hybridization and annealing temperatures are different from one another; alternatively, hybridization and annealing temperatures may be selected such as they are approximately the same.

To start an analysis process involving PCR, a solution 250, for example containing blood cells as previously described, is supplied to the wells 4 through the inlet region 30 of the microfluidic device 1000-1005. Cells lysis and preparation in PCR buffer may be performed before sample loading or it can be performed on-board by means of chemical processing or physical actions (e.g. ultra-sounds, beads, etc.).

According to an embodiment, the aforementioned operation of supplying is done before inserting the microfluidic device 1000-1005 in the device holder 100, so that the cross channels 6b are not closed by the protrusions 74, and the wells 4 can be supplied with the solution 250. After the step of supplying the wells 4 with the solution, the microfluidic device 1000-1005 is secured within the device holder 100, as previously described. Each well 4 is, from now on, completely isolated from the other wells 4 of the same microfluidic device 1000-1005.

DNA amplification by PCR is then carried out in the wells 4. To this end, the temperature controller 211 operates the power source 212 and the cooling element 213 to controllably deliver electric power to the heater 220 and to cyclically control an operating temperature of the solution 250 in the wells 4 in accordance with a desired amplification temperature profile.

Figure 26:
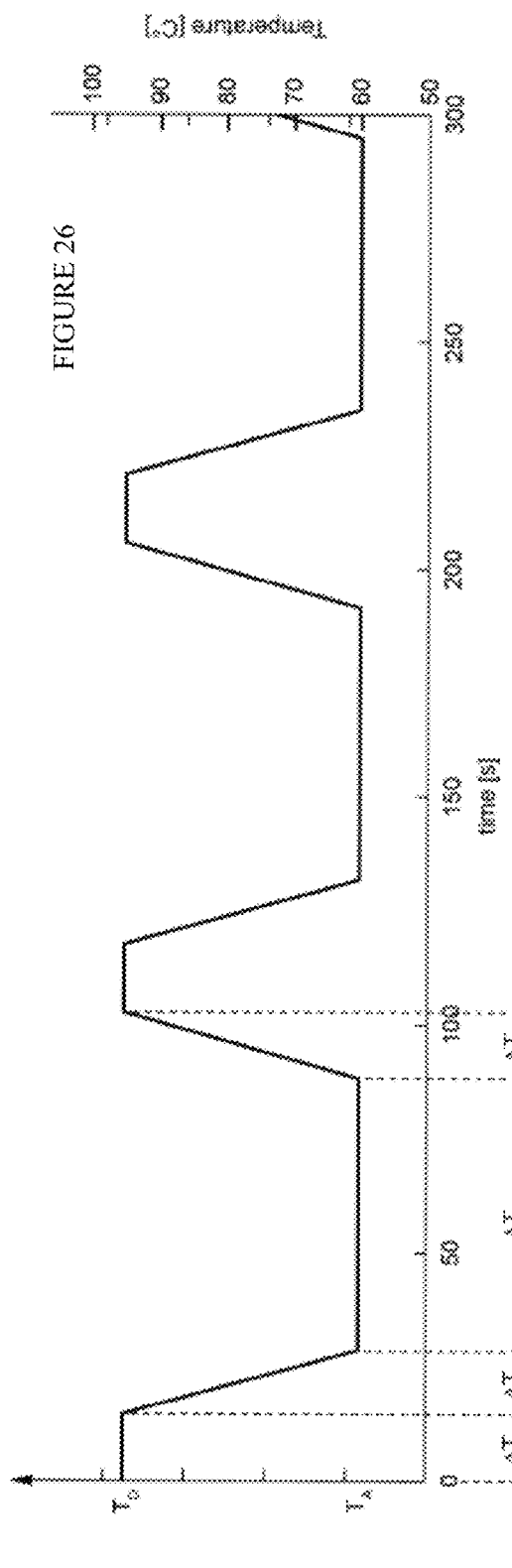
FIG. 26 is a temperature profile used in a method for PCR according to one embodiment.

An example of an amplification temperature profile for the operating temperature during a PCR amplification cycle is shown in FIG. 26. PCR amplification cycles are iteratively carried out until one or more stop conditions are met. For example, DNA amplification is monitored at each cycle of PCR. When the DNA is in the log linear phase of amplification, the amount of fluorescence increases above the background. The point at which the fluorescence becomes measurable may be chosen as the stop condition (this point is also called threshold cycle or crossing point).

With reference to FIG. 26, double stranded DNA is first denatured at a denaturation temperature TD, for example around 95° C., for 10 s to 60 s (interval ΔT1 in FIG. 26, equal to 15 s in the example shown). In this step, DNA helixes separate into single strands.

Then, the temperature of the solution 250 is lowered (cooling phase) to a temperature of about 50° C. to 70° C., for example 60° C. (interval ΔT2 in FIG. 26).

Then, interval ΔT3 in FIG. 26, there is a phase of annealing of the primers, which takes place at a temperature TA of about 50° C. to 70° C. for 10 s to 70 s (60° C. for 60 s in the example shown). At this stage, primers, which are more numerous than the probes, effectively compete for and bind to their complementary sequences in the floating target DNA thus allowing amplification of target sequences.

During interval ΔT3 takes place also the extension (or elongation) phase at which DNA polymerase extends primers, by adding nucleotides that are complementary to the target strand. The extension temperature is, shown, in this example, the same temperature TA as the annealing temperature. Then, the temperature is increased up to TD and a new phase of denaturation takes place. The process is cyclic, and may comprise from 10 to 30 cycling before ending.

During the aforementioned thermal cycle, target DNA can be assessed in any of the known ways in real time, including the use of non-specific intercalating dyes, such as EtBr, or with the use of an array of labeled probes, or with one of the dual labeled probes, such as Molecular Beacon®, Scorpion® or TaqMan® probes.

During each cycle of FIG. 26, the heating rate is, for example, at least 5-7° C./s, while the cooling rate is, for example, greater than 10° C./s.

The cycles may be repeated until sufficient copies of the target DNA have been produced as to be detectable. The amplification process may then be interrupted upon positive detection of the searched target DNA, or after a threshold number of cycles, if the target DNA is not detected (it is thus determined that the starting sample did not contain the target DNA).

It is apparent that other thermal cycles may be used, for example as described in patent application EP2,382,324.

Thermal simulations have been performed to assess ability of the microfluidic device 1000-1005 to undergo the thermal ramps (see FIG. 26) required to perform the PCR cycles, to ensure an accurate and uniform temperature distribution within reaction wells 4.

Finite elements method (FEM) simulations have been performed. To this end, the temperature distribution is simulated for a couple of wells 4 (see FIG. 28). The dimensions of the portion of microfluidic device 1000-1005 that have been considered for the simulation (two reaction wells 4, a trunk of the main channel 6a, two cross channels 6b, and two air exhaust micro channels) includes an height along the Z axis of 1.225 mm, a width along the Y axis of 1.4 mm, and a length along the X axis of 4.6 mm. The dimensions of each well 4 that have been chosen for simulation includes a side length of 0.7 mm for a squared well, and a depth of 0.35 mm.

Both stationary and transient simulations have been performed: stationary simulations are useful to assess absolute thermal performance of the microfluidic device 1000-1005 in terms of accuracy and uniformity, and transient simulations are useful to evaluate the ability of the microfluidic device 1000-1005 to follow time-dependent temperature set-up during PCR cycles.

Only thermal conduction is considered (no temperature field advection by any fluid flow). That means the governing equation is the following:

$$\frac{\partial T}{\partial t} = \vec{\nabla} \cdot (k \vec{\nabla} T)$$

where k is the thermal conductivity of the material and T is the absolute temperature.

The time dependent term vanishes when stationary simulations are performed.

Simulations have been performed considering some basic assumptions, in particular: the wells 4 are completely filled with water (i.e., no air bubbles are trapped within the wells 4 and the network of channels 6); only thermal conduction is considered within the embedded liquid fluids (i.e., potential convective flows are not taken into account therein); only thermal conduction is considered in the air exhaust micro channels (i.e., potential convective flows are not taken into account therein); thermal flux is only due to free convection on the upper side of the microfluidic device 1000-1005 (i.e., radiative flux, negligible in the investigated temperature range, is not taken into account); and the second side 2b of the body 2 is temperature driven (Dirichlet boundary condition). For transient simulations, a 95° C. stationary state is considered as the initial condition.

For performing simulations, several temperature cycles have been simulated. To quantitatively assess thermal performance level of the microfluidic device 1000-1005, three different output indicators have been considered. They have been systematically evaluated at one of the two wells 4 of the simulated portion of the microfluidic device 1000-1005.

The output indicators are defined as follows:

$$\Delta T_{max} = T_{max} - T_{min}$$

which indicates the maximum temperature difference within one reaction well 4;

$$\Delta T_{mean} = \text{mean}(T - T_{setup})$$

which indicates the temperature deviation with respect to the temperature setup. It is an indication of the offset that has to be applied to match temperature setup and the averaged temperature of the considered well 4.

Thermal performance of the microfluidic device 1000-1005 has been evaluated at temperatures $T_{setup1}=60°$ C. and $T_{setup2}=95°$ C. Irrespective of the temperature setup, a weak thermal dispersion (<0.2° C.) was obtained, confirming that, at a stationary state, the required temperature is properly set within the reaction wells 4.

Figure 27:
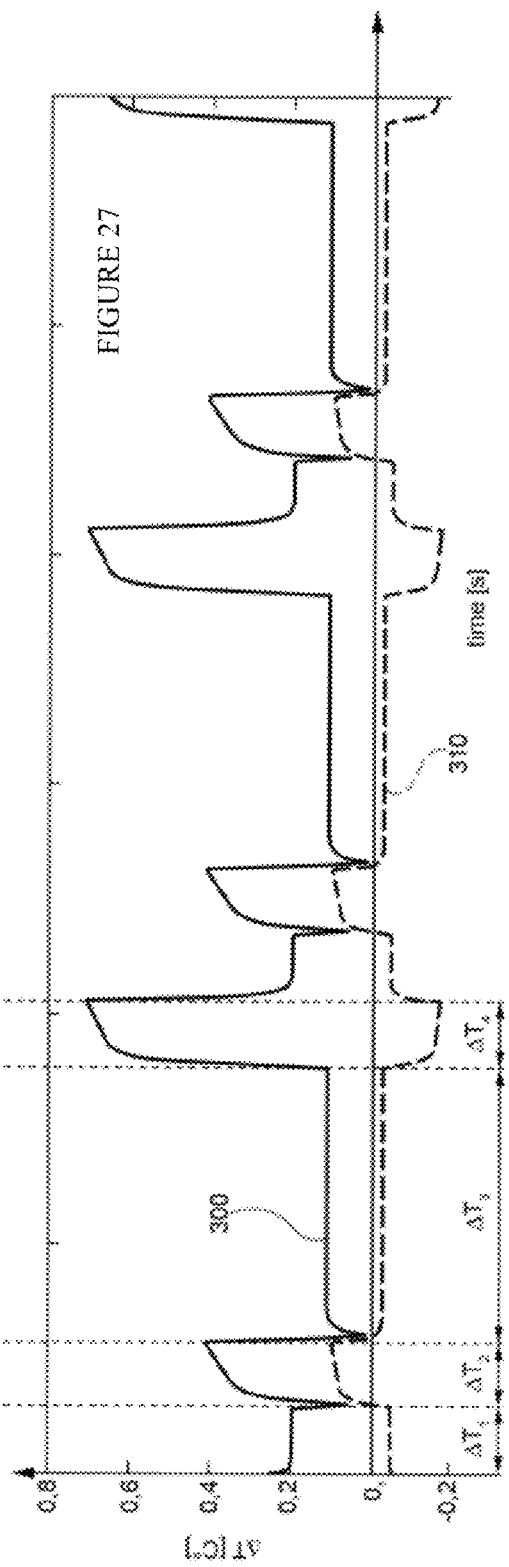
FIG. 27 shows simulations of thermal dispersion and offset within a reaction chamber of the microfluidic device shown in FIG. 28, when the temperature profile of FIG. 26 is applied.
Figure 28:
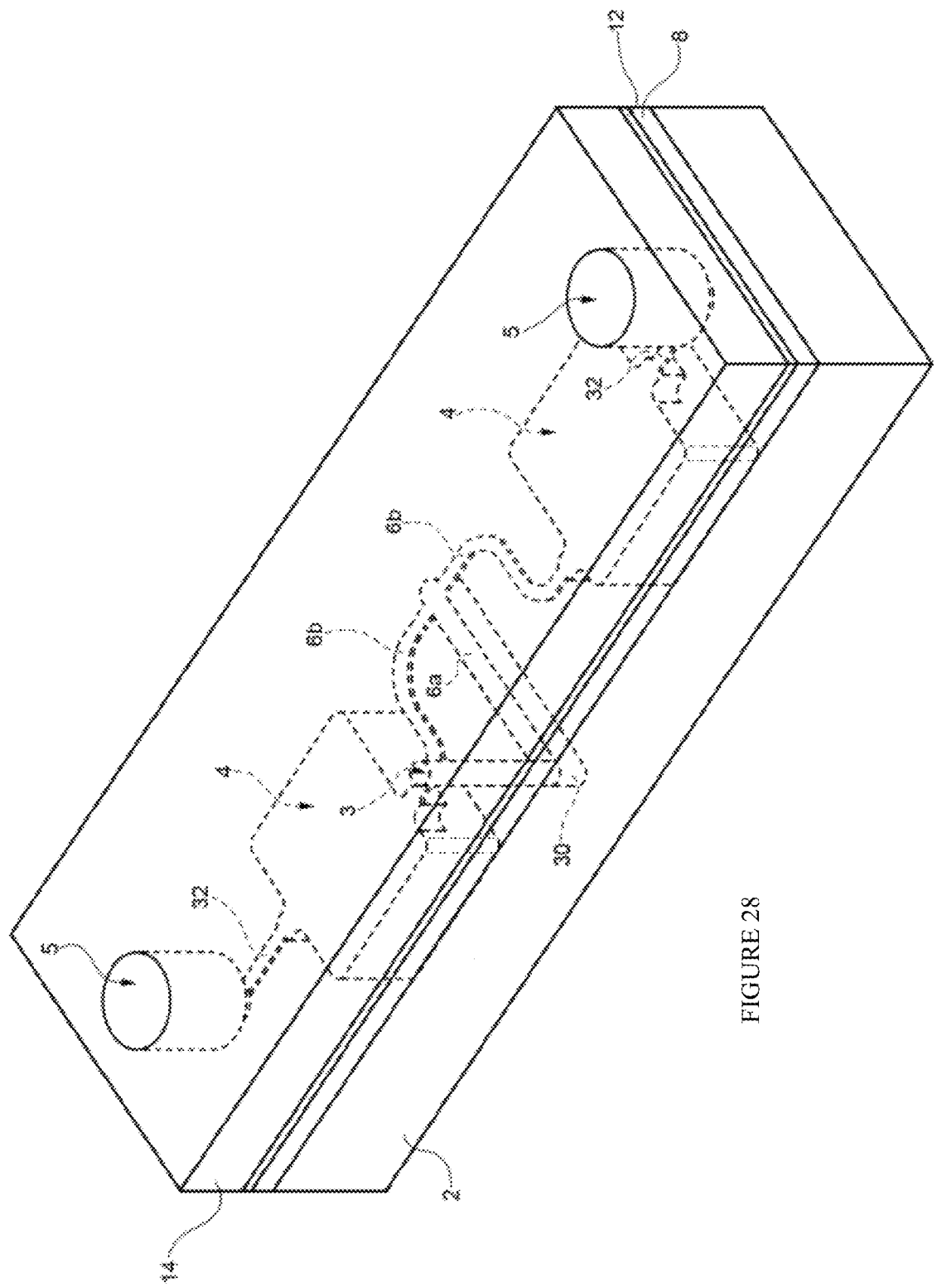
FIG. 28 shows a portion of the body of the microfluidic device comprising a couple of wells 4 used for temperature distribution simulation.

Simulations are performed under a plurality of PCR cycles, according to the temperature profile of FIG. 26, and are reported in FIG. 27 using the same temporal scale as of FIG. 26. FIG. 27 shows dispersion 300 (solid line) and offset 310 (dashed line) curves (see the previously defined output indicators $\Delta T_{max}$ and $\Delta T_{mean}$). The results show that at the beginning of each setup ramp, dispersion and offsets are subject to very short over- or under-shoots, that is due to numerical ramp smoothing which makes computations more robust and has to be considered as an artifact.

Simulations show that with the convection constant at a default value (h=10 W·m-2·K-1, where h is the convection constant), the thermal field remains within the required values ($\Delta T_{max}$<0.25° C., where $\Delta T_{max}$ is the temperature gradient) irrespective of the temperature setup. In terms of transient performance, typical time is below 3.5 seconds, which is quite fast compared to setup plateau duration (15 sec and 60 sec at 95° C. and 60° C. respectively). For the largest h value (e.g., 20 W·m$^{-2}$·K$^{-1}$), the system would be out of specifications, noticeably at $T_{setup}$=65° C., but such a free convection rate is unlikely.

Furthermore, thermal performance of the microfluidic device 1000-1005 has also been simulated when the body 2 is substituted with a plastic body (in particular, polycarbonate), having the same network of channels 6 and wells as the body 2.

Simulations show that, due to the insulating properties of the plastic, the thermal inertia is greater, and dramatically slows down the time needed to reach the plateau.

Moreover, the heat dispersion is higher for the plastic body than the silicon body (about five times higher at temperature equal to 95° C.). Therefore, although plastic can be used for disposable PCR cartridges, semiconductor materials (e.g., silicon) provide a much improved response time with great accuracy. That makes semiconductor materials a valuable material for manufacturing e.g., PCR multiplex devices with strict thermal requirements.

With the current design, thermal power required to perform accurate ramps (slope of 2.5° C./s) can be roughly estimated as about 30 mW for the heating step and 25 mW for the cooling step.

Main results of the thermal study are the following: at stationary state, the microfluidic device 1000-1005 provided with heaters and temperature sensor integrated at the second side 2b of the body 2, and free convection over the upper side (through the air exhaust micro channels) fulfills predetermined thermal requirements (e.g., dispersion <0.25° C.) within any one reaction well 4, irrespective of the temperature setup.

A semiconductor-based (in particular silicon-based) body 2 allows the microfluidic device 1000-1005, to almost perfectly follow the thermal ramps (heating and cooling steps). The microfluidic device 1000-1005 reaches a plateau almost instantaneously.

In the following discussion, proof will be given that a microfluidic device wherein the depth $D_W > D_{MC} > D_{CC}$ is effective in preventing cross contamination among wells 4. To do so, we simulated PCR experiments with a dual labeled probe, wherein the fluorophore is released during extension, such as with a Taqman probe. As described, the microfluidic device according to the present invention comprises a plurality of wells 4 (which are reaction wells when it is used as a PCR cartridge, according to an embodiment of the present invention). Each well 4 may contain a specific primer and probe, spotted in the reaction well. Thus, each reaction well 4 can contain a different target that can be amplified at the same time as the target of another reaction well 4. At the starting time, primers and probes are well separated, but during the time of a PCR experiment, they may be transported from one well to a neighboring well due to molecular diffusion. Possibly, a wrong couple of primers and probes in a given well will give rise to a non-specific signal and then will lead to false quantification results. The microfluidic device according to the present invention makes this risk considerably low.

Candidate PCR classically relies on well designed primers but also on specific probes named reporters. To produce a signal unit, a primer and a probe must hybridize to a DNA template in a same thermal cycle. When in suspension in the liquid sample, probes are quenched and actually produce a very low fluorescence signal. But when they participate in an amplification, they are digested by Taq® Polymerase during elongation process and then unquenched free fluorescent molecules are released. Every time both primers and probes hybridize to a target to produce an amplicon, a fluorescence unit is definitively added to the liquid sample. The fluorescence signal is monitored by the instrument during the whole PCR experiment.

Amplicons are the prime output of a PCR. Consequently, in an initial study, we first focus on those DNA molecules to well understand the basic processes involved in the contamination process. Then, we take a closer look at the amount of fluorescent molecules, which allow the instrument to monitor the PCR. The amount of free fluorophores is actually different from the amount of produced amplicons during the PCR because primers and probes do not have either the same initial concentrations nor the same diffusion coefficients. The aim of the study is to evaluate the risk of a contamination of well 4 by PCR products specific of another well 4. To this end, absolute amounts or averaged concentrations of either amplicons or free fluorophores will be systematically compared. Contamination level by fluorophores will also be compared to current system limit of detection to assess if a potential contamination may be detected or not.

The following reference parameters were used. Each diffusion step lasted 89 seconds.

---

Probes:

Sequence length: 15-20 bases
Initial concentration: 250 nM
Diffusion coefficient (m$^2$ · s$^{-1}$): 1.6 × 10$^{-10}$
Primers:

Sequence length: 19-23 bases
Initial concentration: 900 nM
Diffusion coefficient (m$^2$ · s$^{-1}$): 1.6 × 10$^{-10}$
Targets:

Sequence length: 58 bases
Initial concentration: 1 → 1 × 10$^5$ copy/well; 7.5 × 10$^{-6}$ → 0.75 nM
Diffusion coefficient (m$^2$ · s$^{-1}$): 0.9 × 10$^{-10}$
FAM:

Sequence length: 1 base + FAM molecule + linker
Initial concentration: 0 nM
Diffusion coefficient (m$^2$ · s$^{-1}$): 2.0 × 10$^{-10}$

---

Figure 29A:
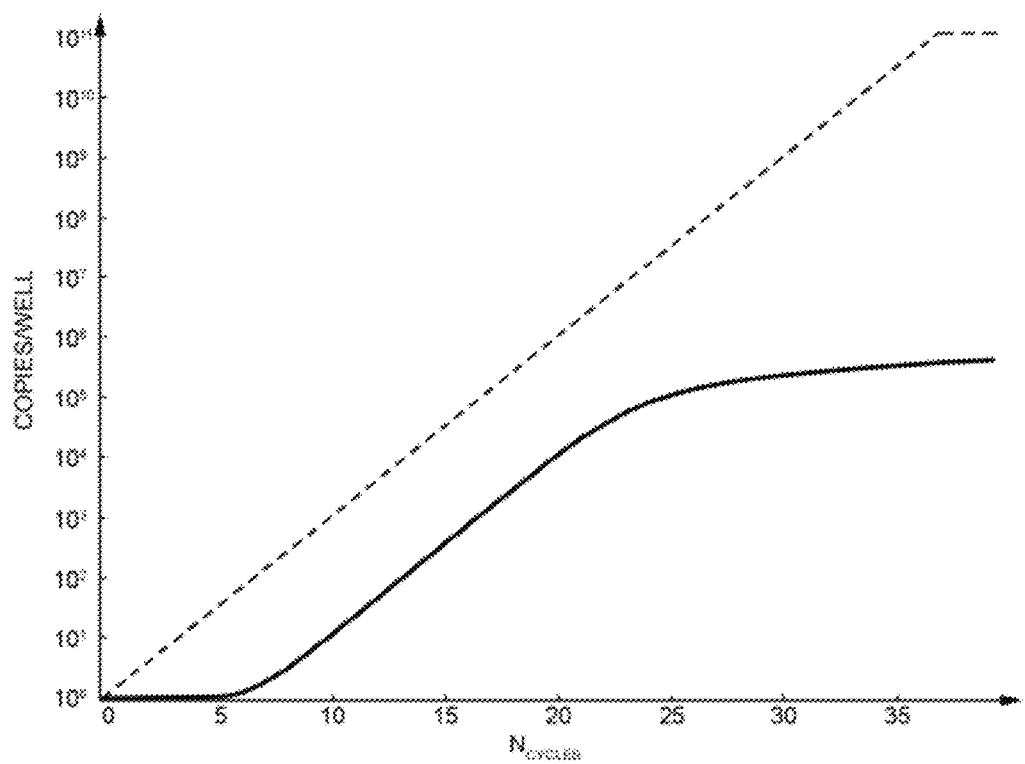
FIGS. 29a and 29b show simulated amplification results relating to a reaction chamber (dotted line) and an adjacent negative control chamber (solid line) of a microfluidic device having a body as shown in FIG. 3b or 4b, after 40 PCR cycles with low and, respectively, high initial target concentration.
Figure 29B:
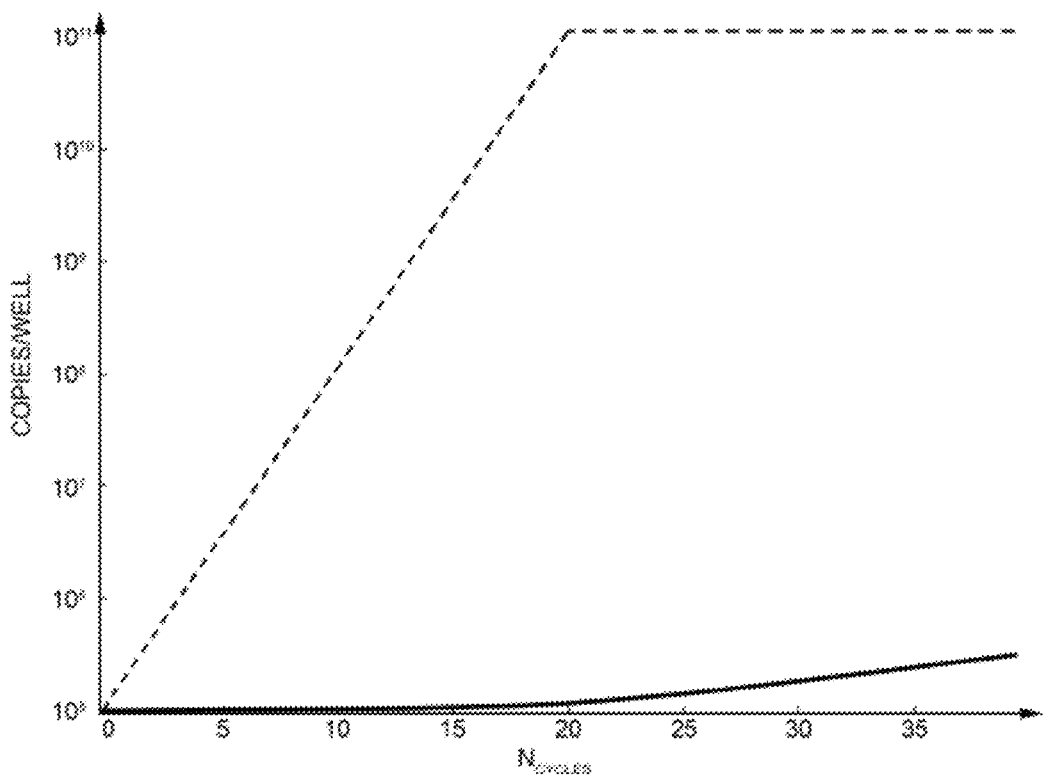

FIG. 29a, 29b show simulated amplification results after 40 cycles with both low and high initial target concentration (respectively, 1 and 1×10$^5$ copies per well). Amplification yield was set to 1. In this graph, the amount of amplicons produced in both wells are presented as a function of the number of cycles $N_{cycles}$.

Throughout the study, graphs will be presented the same way, wherein the dotted line curve indicates the amount of molecules of interest (DNA targets or free fluorophores) contained in a well 4 where primers and probes have been formerly spotted. Solid lines, in contrast, refer to the amount of molecules of interest (DNA targets or free fluorophores) in an adjacent well 4 where only targets were initially contained. The dotted line thus signals the level of contamination of this negative control well.

With reference to FIG. 29a, the reaction well 4 (dotted curve) exhibits a typical exponential growth (linear curve in logarithmic y-scale) before saturation because of complete primers depletion (maximum concentration reached is 880 nM, which is almost the initial primers concentration).

The same amplification rate is observed in the control well 4 (solid curve) but with a delay of 6 to 7 cycles, the time required for fluid to flow from the reaction well 4 to the control well 4, by diffusion. At around 25 cycles, solid curve growth rate decreases because primers contained in the reaction well are severely depleted. The very low rate of increase of DNA targets in the control well 4 after this 25th cycle shows that incoming flux of primers collapse. Perhaps signal continues to increase only because of diffusion of amplicons contained in the microfluidics channel, which links the two wells.

If we now focus on the high target concentration curve (FIG. 29b), the results are the same. But initial amount of target in the reaction well 4 (dotted curve) is so high that primers are considerably more quickly depleted. As a consequence, it increases the delay for first primers to reach the control well 4 where PCR amplification starts at the 20th cycle.

Figure 30A:
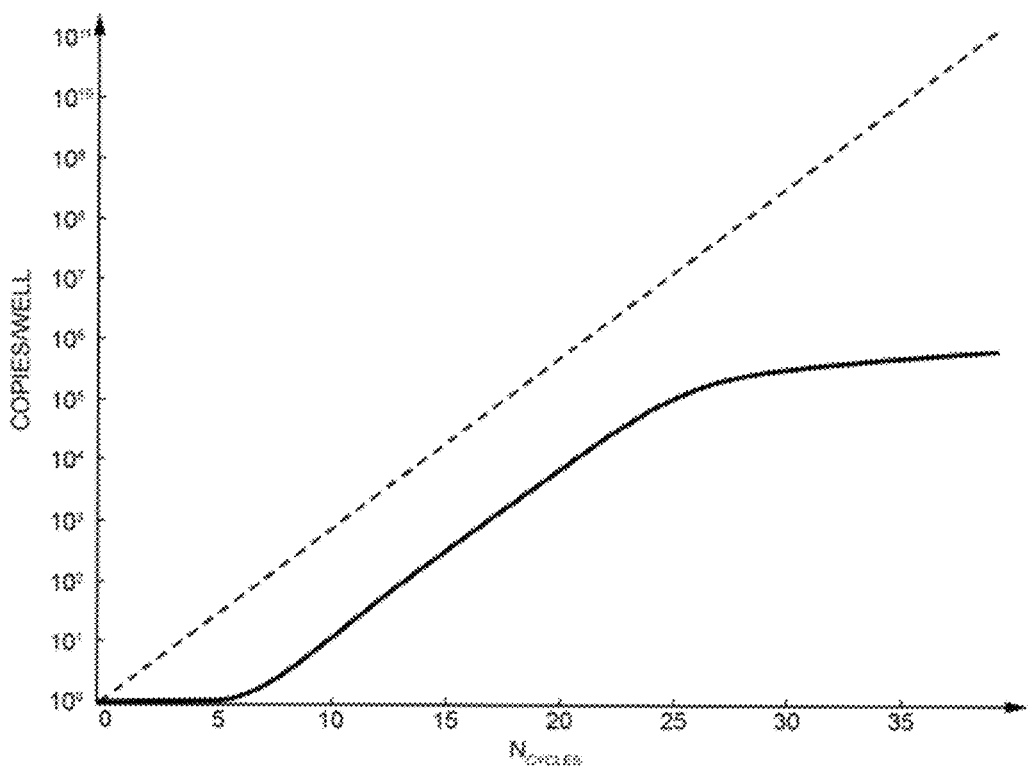
FIGS. 30a and 30b show simulated amplification results relating to a reaction chamber (dotted line) and a control chamber (solid line) of a microfluidic device having a body as shown in FIG. 3b or 4b, after 40 PCR cycles with low and, respectively, high initial target concentration, in a case where the amplification yield is weaker than the situation of FIG. 29a, 29b.
Figure 30B:
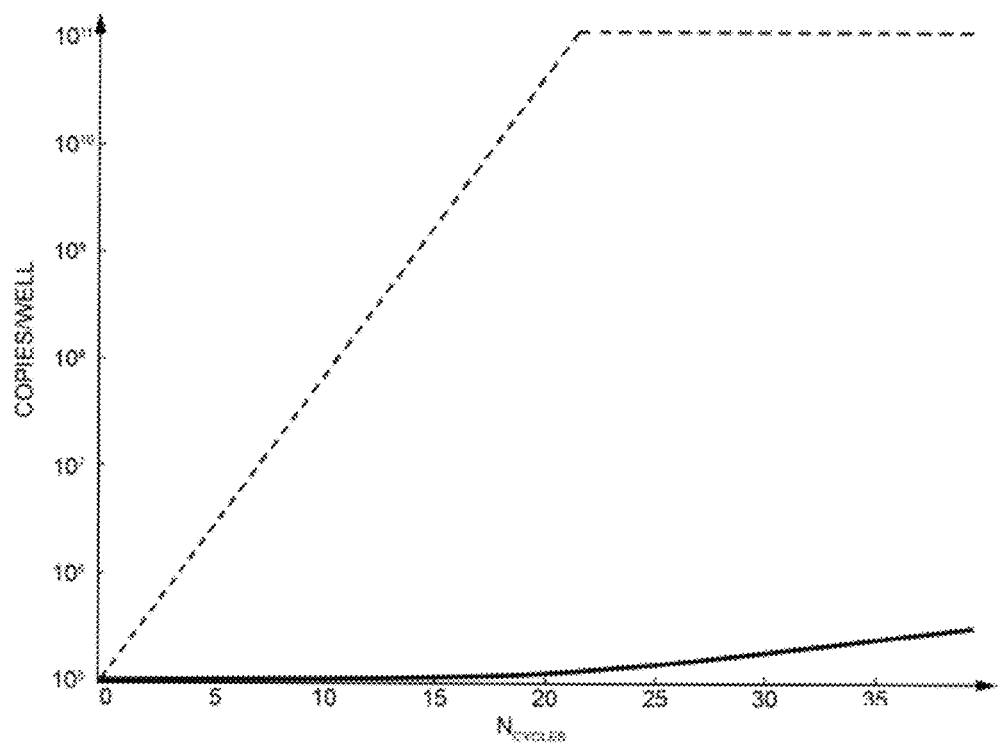

In case of a weaker amplification yield r=0.9, the situation is the same although saturation is not reached in the reaction well 4 after 40 cycles with a low target load as illustrated in FIG. 30a, 30b.

Simulated results show that, whatever the yield rate r, the amount of targets in the reaction well 4 (solid curve) after 40 cycles is always the same. In every case, ratio of amplicons in the reaction well 4 (dotted curve) versus those contained in the control well 4 is extremely high (20,000 in the worst case scenario). This means that, according to simulated experiments, contamination exists but may be undetectable compared to the amount of specific amplicons even with a very low target load.

According to another simulation, a fluorescence signal is produced only if a primer and a probe hybridizes to a DNA template at the same time. The aforementioned probe is, according to an embodiment, a TaqMan® probe. Because there are initially less probes than primers, there will be actually more amplicons produced than free fluorophores released in the cartridge at the end of the PCR experiment.

Figure 31A:
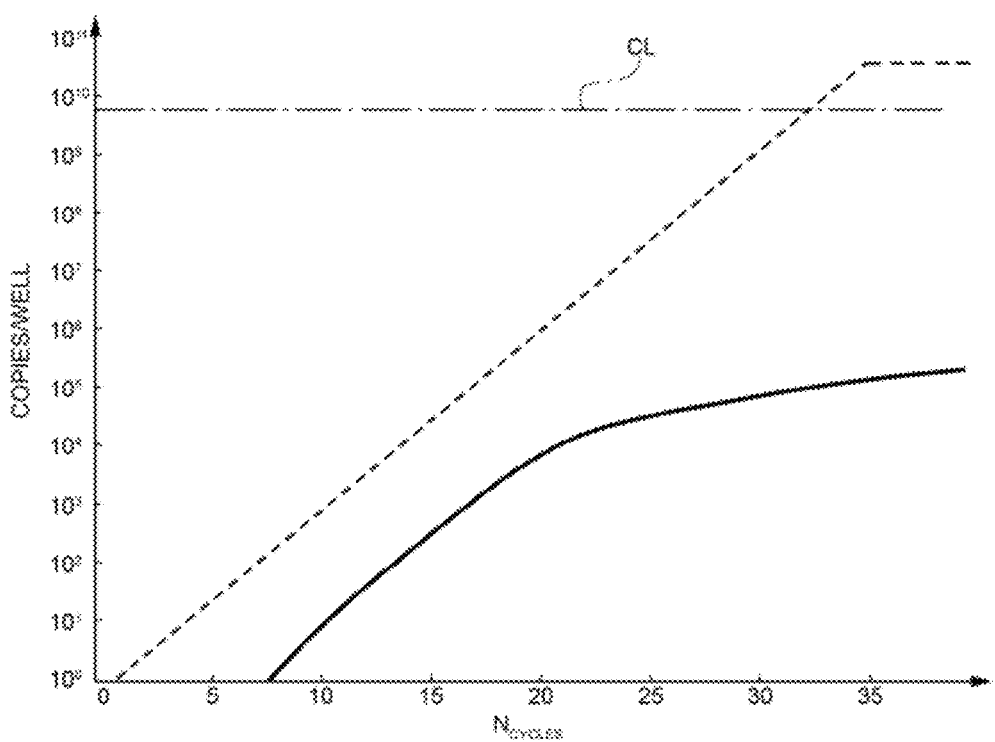
FIGS. 31a and 31b show simulated results relating to the amount of free fluorophores released in both reaction (dotted curve) and control (solid curve) chambers of a microfluidic device having a body as shown in FIG. 3b or 4b, as a function of PCR cycles number at low initial target concentration and, respectively, high initial target concentration.
Figure 31B:
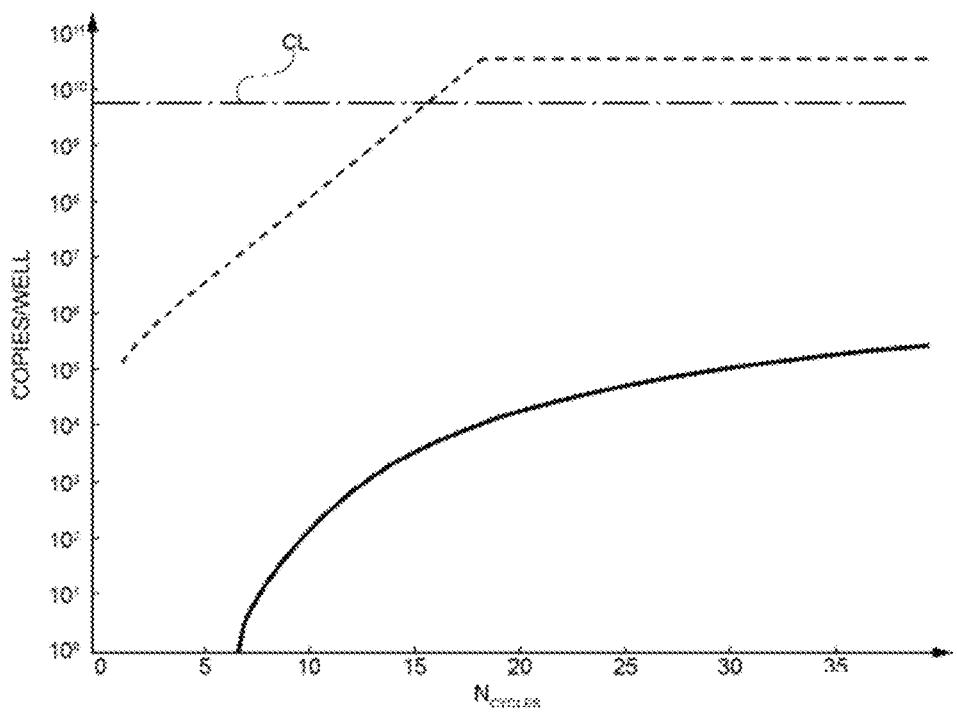

In the same manner as with amplicons study, it is analyzed the amount of free fluorophores released in both reaction (dotted curve) and control (solid curve) wells 4 as a function of PCR cycles number (FIG. 31a, 31b). At low initial target concentration (FIG. 31a), the same delay of 6 to 7 cycles is observed between the two wells. Around the 25th cycle, exponential growth phase stops and fluorescence signal increases mainly because of a severe primer depletion in the reaction well. At high initial target concentration (FIG. 31b), curve behavior is quite the same except that exponential growth rate decrease earlier than with a lower target load.

On these curves, the current specified limit of detection of the system is indicated by line CL. As a reminder, the aim of this study was to assess the risk of contamination of control well by primers and probes coming from the adjacent reaction well and producing non-specific fluorescence signal in the control well. In other terms, to be sure that a contamination signal is non-detectable by the system, the solid curve must remain below the line CL (and obviously the further below, the better). It can be observed that it is always true and in every case, with a good margin. Potential contamination signal is 20000 times less than the current limit of detection of the optical system.

As a conclusion, whatever the amplification yield rate r, fluorescence contamination occurs, but with an associated level of fluorescence well below the limit of detection of the system.

It must be noticed that the given results relate to a fluorescence signal produced by one primer. PCR protocol is actually designed with a couple of specific primers. Strictly speaking, simulated signal level should be multiplied by a factor of two before being compared to detection limit of the system. Nevertheless, difference between the concentration of fluorophores in the two reaction wells is so high that it does not affect the conclusions that the microfluidic device according to the present invention is effective in considerably reducing cross-contamination among wells fluidically coupled to a same fluidic channel.

It can be noticed that the results of FIG. 29a-31b relate to a geometry as given, for example, in FIG. 3b or 4b, where microchannels linking reaction wells to main loading microchannel come out "face to face". Considering former results with both amplicons and fluorophores, we may expect that increasing the path length between the two reaction wells would reduce the contamination level in the non-functionalized well 4. This can be done by staggering the secondary channels 6b as shown, for example, in FIG. 10a, 10b.

Figure 32:
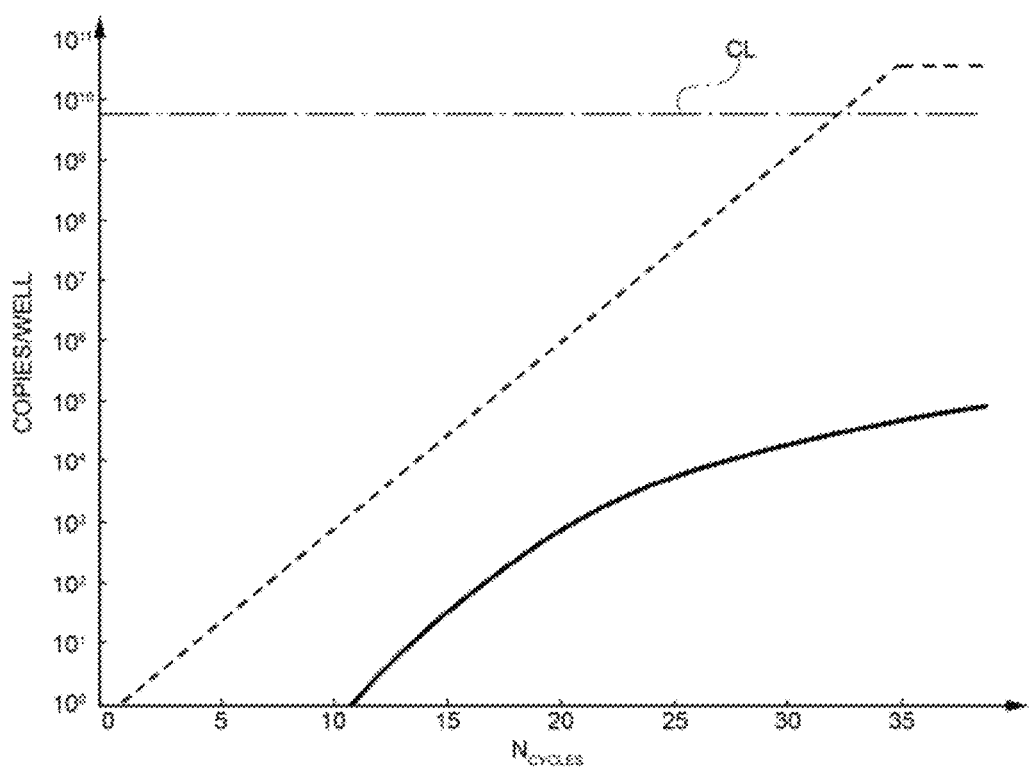
FIGS. 32 and 33 show the simulated results relating to a reaction chamber (dotted line) and a control chamber (solid line) of a microfluidic device having a body as shown in FIGS. 10a and 10b, for low and, respectively, high initial target concentration.
Figure 33:
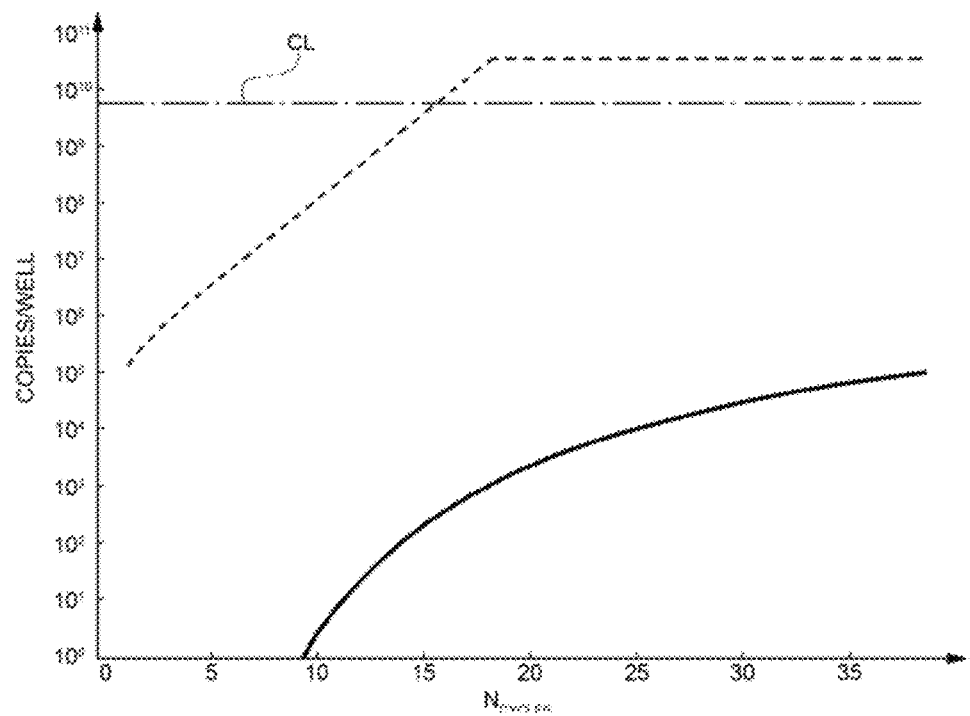

FIGS. 32 and 33 show the simulated results when a pathway extension is taken into account (for example of around 500 μm), for both low (FIG. 32) and high (FIG. 33) initial target concentration respectively. Because more time is needed for primers and probes to reach the control well 4, it results in a adding a delay of 3 to 4 cycles between reference and modified geometry. As a consequence, since exponential growth rate in the control well (solid curve) remains roughly the same, final free fluorophores concentration in the control well is smaller in case of staggered microchannels by a factor of three.

All previous simulations are based on the reference diffusion coefficients given above. It is now analyzed the case in which targets, probes or free fluorophores are able to travel faster through the microfluidics channels. Because primers and probes on one side and free fluorophores on the other side play different roles in a PCR process (first ones serve to amplify targets when the second acts as a signal transducer), sensitivities of the model to higher molecular diffusion coefficients are studied separately.

Figure 34A:
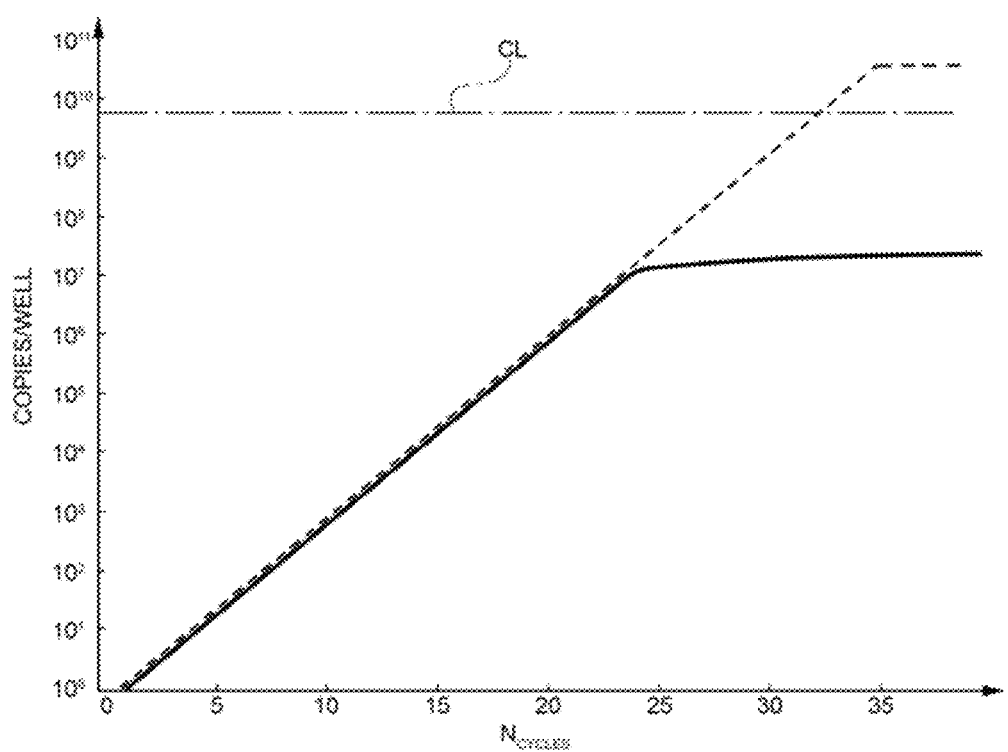
FIGS. 34a and 34b show simulated results relating to the amount of free fluorophores released in both reaction (dotted curve) and control (solid curve) chambers of a microfluidic device having a body as shown in FIG. 10a or 10b, as a function of PCR cycles number at low initial target concentration and, respectively, high initial target concentration.
Figure 34B:
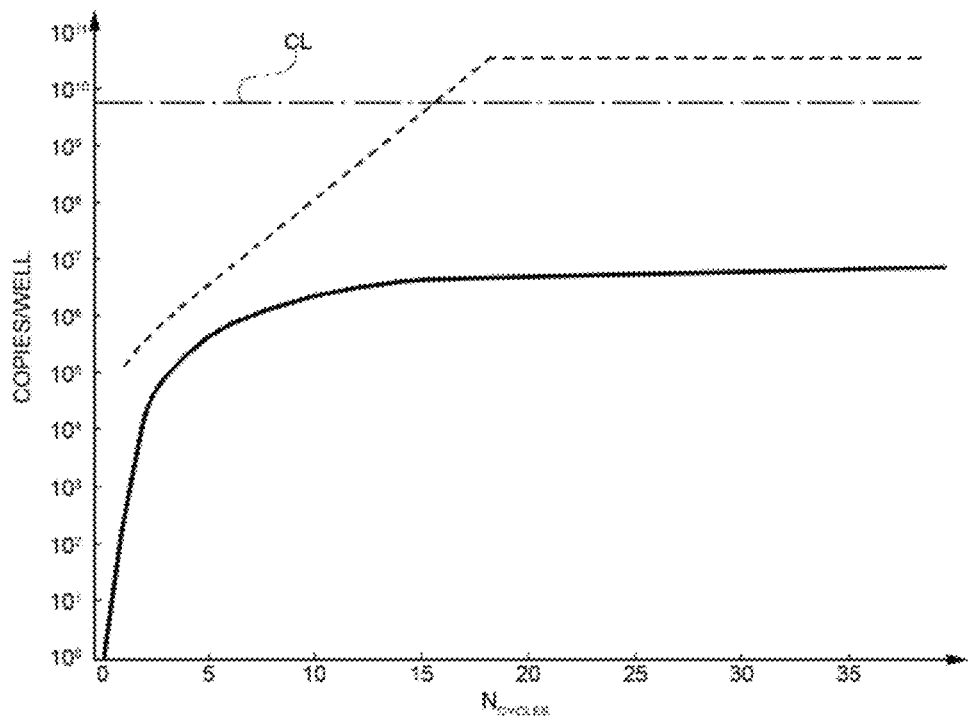

If molecular diffusion coefficients D are multiplied by a factor of 10, but other simulation parameters remaining unchanged, system behavior is quite different compared to reference case analyzed previously. Simulated results for amount of free fluorophores in both reaction and control wells 4 are shown in FIG. 34a (low initial target concentration) and FIG. 34b (high initial target concentration). Dotted curve refers to reaction well 4; solid curve refers to control well 4.

At a low concentration (FIG. 34a), because primers and probes can spread very quickly through the microfluidics network, exponential growth starts at the same time in the two reaction chambers. Nevertheless, PCR is privileged in the reaction well 4 (dotted curve) since primers and probes have been spotted there. At some point, around 23rd cycle, primers begin to be limited in the control well 4 (solid curve) and free fluorophore release rate in the control well suddenly drops.

At high initial target concentration (on the right), curve shape in control well 4 is similar than with lower diffusion rates but fluorescence rises earlier than in the reference case of non-staggered secondary channels 6b.

If molecular diffusion coefficient D of free fluorophores is modified, fluorescence signal in the control well 4 at the end of the 40 thermal cycles increases (graphs not shown), but with a level remaining well below the limit of detection of the system. In fact, the worst case scenario gives a fluorescence level of 0.13 nM to be compared to the 40 nM limit of detection.

These simulations show that the model is sensitive to diffusion rates input parameters. However, it has to be noted that fluorescence contamination by diffusion of probes, primers and fluorophores would certainly never exceed the limit of detection of the system.

From an examination of the characteristics provided according to the present invention, further advantages emerge clearly.

The microfluidic device according to the present invention has low cost and thus finds an application as a disposable device.

The plurality of reaction wells (e.g., 96 wells), each of them capable of storing, according to an embodiment, a liquid volume of 200 to 300 nl, allows the user to perform a plurality of biological analysis at the same time. Moreover, given that, according to an embodiment, the material (e.g., silicon) in which the wells are formed is thermally conductive, a plurality of thermal cycles can be conducted, according to any particular need.

The fluidic device of the present invention can be manufactured using standard MEMS processing and technology (e.g., lithography and etching). Thus, manufacturing costs are reduced.

Furthermore, the fluidic device is provided, according to an embodiment, of a heater and a temperature sensor both distributed on the surface opposite to that of the wells, so as to ensure a uniform heating of all of the wells with temperature differences contained below 1° C., with and without the sample and reaction products.

Finally, it is clear that modifications and variations may be made to the embodiments described and illustrated herein, without thereby departing from the scope of protection of the present invention, as defined in the annexed claims.

For example, the air outlet region 32 can be omitted and each air exhaust channel formed vertically aligned (along the Z axis) with a portion of a respective well 4 instead.

According to a further embodiment, the bi-adhesive layer 90' of FIG. 12a, 12b can be used in any one of the embodiments of the microfluidic device previously described, in particular microfluidic device 1000, 1001, 1002, to substitute the bi-adhesive layer 12 and/or 20 and/or 20'.

Further, the arrangement of wells, channels, heaters and sensor can be modified according to need, following the design principles discussed herein. Further, the shape and size of any openings can be modified as needed.

The invention claimed is:

1. A microfluidic device, comprising:
a body having a first side and a second side opposite the first side, said first side having:
at least two amplification reaction chambers, the amplification reaction chambers configured to store reagents and samples;
an inlet region forming an entrance for a fluid to be supplied to the amplification reaction chambers;
a main channel fluidically connected to the inlet region; and
at least two secondary channels, each one of the secondary channels fluidically connecting the main channel to a respective one of the amplification reaction chambers,
wherein the amplification reaction chambers extend within the body for a first depth, the main channel extends within the body for a second depth, the secondary channels extend within the body for a third depth, the first depth being greater than the second depth, and the second depth being greater than the third depth.

2. The microfluidic device according to claim 1, wherein the secondary channels are coupled to opposite sides of the main channel and are staggered with respect to one another.

3. The microfluidic device according to claim 1, wherein the main channel and the secondary channels are configured to transport the fluid within the main channel and the secondary channels by capillary action.

4. The microfluidic device according to claim 1, further comprising a flexible layer arranged above the first side of the body and provided with at least a protrusion extending towards the first side of the body and overlapping, at least partially, the secondary channels, the flexible layer being configured to selectively, fluidically isolate a first one of the amplification reaction chambers from a second one of the amplification reaction chambers, upon application of a pressure to the flexible layer.

5. The microfluidic device according to claim 4, further comprising a cover layer, arranged above the first side of the body and configured for sealing the amplification reaction chambers.

6. The microfluidic device according to claim 5, wherein the flexible layer is arranged above the cover layer, the cover layer being provided with at least a first valve hole which extends through the cover layer and overlaps, at least partially, the secondary channels, the protrusion extending through the first valve hole.

7. The microfluidic device according to claim 5, further comprising a plurality of air exhaust channels, each of the air exhaust channels being fluidically coupled to a respective one of the amplification reaction chambers, and configured to exhaust a gas from within the amplification reaction chambers to an environment external to the amplification reaction chambers.

8. The microfluidic device according to claim 7, wherein the air exhaust channels extend through the cover layer, the microfluidic device further comprising a membrane layer arranged above the cover layer in such a way to cover the air exhaust channels and configured to be impermeable to said fluid and permeable to said gas.

9. The microfluidic device according to claim 8, wherein the air exhaust channels further extend through the flexible layer, and wherein the membrane layer is arranged above the flexible layer.

10. The microfluidic device according to claim 1, wherein the inlet region is accessible through a pipette or micro pipette for supplying said fluid.

11. The microfluidic device according to claim 5, wherein the body houses one or more grooves extending at the first side, at least partially around one or more of the amplification reaction chambers, the cover layer being sealed to the body by glue within said grooves.

12. The microfluidic device according to claim 11, wherein the glue is a biocompatible, non-fluorescent, glue.

13. The microfluidic device according to claim 5, further comprising a first bi-adhesive layer arranged between the body and the cover layer, configured to couple the cover layer to the body.

14. The microfluidic device according to claim 13, wherein the first bi-adhesive layer is provided with at least two inspection holes, extending through the first bi-adhesive layer for its entire thickness, the at least two inspection holes being at least partially aligned with the at least two amplification reaction chambers, respectively.

15. The microfluidic device according to claim 1, further comprising an integrated heater formed at the second side of the body.

16. The microfluidic device according to claim 1, further comprising an integrated temperature sensor formed at the second side of the body.

17. The microfluidic device according to claim 4, forming a microreactor, wherein each one of the amplification reaction chambers accommodates an array of nucleic acid probes at respective locations configured to hybridize to respective target nucleic acids; and wherein said fluid is a solution containing primers, capable of binding to target nucleic acids, nucleotides, nucleic acid extending enzymes and nucleic acids.

18. The microfluidic device according to claim 4, wherein the flexible layer is transparent to at least a first wavelength and a second wavelength, the first wavelength and the second wavelength different from one another.

19. The microfluidic device according to claim 5, wherein the cover layer is transparent to at least a first wavelength and a second wavelength, the first wavelength and the second wavelength different from one another.

20. The microfluidic device according to claim 1, further comprising an enclosing structure having lateral walls arranged on the first side of the body to completely encircle the amplification reaction chambers, said enclosing structure being further provided with a reservoir fluidically coupled to the inlet region and configured for containing an amount of said liquid greater than an amount of said liquid that can be contained by the inlet region.

21. A microfluidic device, comprising:
a body having a first side and a second side opposite to one another, said first side having:
 a plurality of amplification reaction chambers, the amplification reaction chambers configured to store reagents and samples;
 an inlet region forming an entrance point for a fluid to be supplied to the amplification reaction chambers;
 a main channel fluidically connected to the inlet region; and
 a plurality of secondary channels, each one of the secondary channels fluidically connecting the main channel to a respective one of the, the amplification reaction chambers;
a cover layer, arranged above the first side of the body, configured to seal the amplification reaction chambers and provide at least a first valve hole which extends through the cover layer and overlaps, at least partially, the secondary channels; and
a flexible layer, arranged above the cover layer and provided with at least a protrusion extending through the first valve hole towards the body and overlapping, at least partially, a respective one of the secondary channels, the flexible layer being configured such that, when a pressure is applied on the flexible layer, the protrusion contacts the body and enters within the respective one of the secondary channels, thus fluidically isolating a respective one of the plurality amplification reaction chambers from the main channel.

22. A cartridge comprising:
a microfluidic device including:
 a body having a first side and a second side opposite the first side, said first side having:
  at least two amplification reaction chambers, the amplification reaction chambers configured to store reagents and samples;
  an inlet region forming an entrance for a fluid to be supplied to the amplification reaction chambers;
  a main channel fluidically connected to the inlet region; and
  at least two secondary channels, each one of the secondary channels fluidically connecting the main channel to a respective one of the amplification reaction chambers,
  wherein the amplification reaction chambers extend within the body for a first depth, the main channel extends within the body for a second depth, the secondary channels extend within the body for a third depth, the first depth being greater than the second depth, and the second depth being greater than the third depth; and
 a device holder configured to house said microfluidic device, including a base portion and a cover portion, the cover portion having a protrusion, the base portion and the cover portion configured to be coupled to one another and to exert pressure on the microfluidic device along a direction parallel to a direction of extension of the protrusion, so that the protrusion contacts the body and enters within at least one of the secondary channels, thus fluidically isolating a respective one of the at least two amplification reaction chambers from the main channel.

23. A nucleic acid amplification apparatus, comprising:
a microfluidic device that includes:
a body having a first side and a second side opposite the first side, said first side having:
 at least two amplification reaction chambers, the amplification reaction chambers configured to store reagents and samples;
 an inlet region forming an entrance for a fluid to be supplied to the amplification reaction chambers;
 a main channel fluidically connected to the inlet region; and
 at least two secondary channels, each one of the secondary channels fluidically connecting the main channel to a respective one of the amplification reaction chambers,
 wherein the amplification reaction chambers extend within the body for a first depth, the main channel extends within the body for a second depth, the secondary channels extend within the body for a third depth, the first depth being greater than the second depth, and the second depth being greater than the third depth.

24. The apparatus according to claim 23, comprising a temperature control module for cyclically controlling an operative temperature of the solution in accordance with a temperature profile.

25. The apparatus according to claim 23, further comprising a reader device and wherein the microfluidic device is mounted on a board to form a cartridge loadable into the reader device.

26. The apparatus according to claim 25, wherein the reader device is an optical reader and includes:
a light source for illuminating the microfluidic device with light at a first wavelength; and
an image detector, configured to receive light radiation at a second wavelength emitted by the microfluidic device, in response to the light at the first wavelength.

27. A method of manufacturing a microfluidic device, comprising:
forming at least two amplification reaction chambers for storing reagents and samples in a first side of a body that also includes a second side opposite to the first side, the at least two amplification reaction chambers having a first depth;

forming an inlet region in the first side, the inlet region forming an entrance for a fluid to be supplied to the amplification reaction chambers;

forming a main channel in the first side, the main channel being fluidically connected to the inlet region, and having a second depth; and forming at least two secondary channels in the first side, each one of the at least two secondary channels fluidically connecting the main channel to a respective one of the at least two amplification reaction chambers, respectively, and having a third depth;

wherein the first depth is greater than the second depth, and the second depth is greater than the third depth.

28. The method of manufacturing according to claim 27, further comprising:

arranging a cover layer above the first side of the body, so as to seal the amplification reaction chambers, the cover layer being provided with at least a first valve hole that extends through the cover layer and overlaps, at least partially, the secondary channels; and arranging a flexible layer above the cover layer, the flexible layer being provided with at least a protrusion extending through the first valve hole towards the body and overlapping, at least partially, at least one of the at least two secondary channels.

29. A method of manufacturing a microfluidic device, comprising:

forming, at a first side of a body, at least two amplification reaction chambers for storing reagents and samples, an inlet region that is an entrance for a fluid to be supplied to the amplification reaction chambers; a main channel fluidically connected to the inlet region; and at least two secondary channels each fluidically connecting the main channel to a respective one of the at least two amplification reaction chambers, respectively, the body also having a second side opposite to the first side;

arranging a cover layer above the first side of the body, so as to seal the amplification reaction chambers, the cover layer having at least a first valve hole that extends through the cover layer and overlaps, at least partially, at least one of the at least two secondary channels; and arranging a flexible layer above the cover layer, the flexible layer being provided with at least a protrusion extending through the first valve hole towards the body and overlapping, at least partially, at least one of the at least two secondary channels.

30. A method of operating the microfluidic device of claim 4, comprising:

supplying a liquid solution at the inlet region; and after the step of supplying, applying a pressure on the flexible layer such that the protrusion contacts the body and enters within at least one of the secondary channels, thus fluidically isolating a respective one of the at least two amplification reaction chambers from the main channel.

31. A method of performing a chemical analysis, said method comprising:

applying a sample to the inlet region of the microfluidic device including a body having a first side and a second side opposite the first side, said first side having:

at least two amplification reaction chambers;

an inlet region forming an entrance for a fluid to be supplied to the amplification reaction chambers;

a main channel fluidically connected to the inlet region; and at least two secondary channels, each one of the secondary channels fluidically connecting the main channel to a respective one of the amplification reaction chambers, wherein the amplification reaction chambers extend within the body for a first depth, the main channel extends within the body for a second depth, the secondary channels extend within the body for a third depth, the first depth being greater than the second depth, and the second depth being greater than the third depth;

inserting said microfluidic device into a reader device, activating said reader device and obtaining a result of a chemical analysis.

32. The method of claim 31, wherein said chemical analysis is a DNA amplification and detection of same, and said sample is a biological fluid.

33. The method of claim 31, wherein said chemical analysis is an antibody-antigen binding reaction and detection of same, and said sample is a biological fluid.

34. The method of claim 31, wherein said chemical analysis is an enzymatic reaction and detection of same, and said sample is a biological fluid.

35. The microfluidic device according to claim 22, wherein the main channel and the secondary channels are configured to transport the fluid within the main channel and the secondary channels by capillary action.

36. The microfluidic device according to claim 22, further comprising a flexible layer arranged above the first side of the body and provided with at least a protrusion extending towards the first side of the body and overlapping, at least partially, at least one of the at least two secondary channels, the flexible layer being configured to selectively, fluidically isolate a respective one of the at least two amplification reaction chambers from the main channel, upon application of a pressure to the flexible layer.

37. The microfluidic device according to claim 36, further comprising a cover layer, arranged above the first side of the body and configured for sealing the amplification reaction chambers.

38. The microfluidic device according to claim 37, wherein the flexible layer is arranged above the cover layer, the cover layer being provided with at least a first valve hole which extends through the cover layer and overlaps, at least partially, at least one of the at least two secondary channels, the protrusion extending through the first valve hole.

* * * * *